US012410132B2

(12) United States Patent
Gu et al.

(10) Patent No.: US 12,410,132 B2
(45) Date of Patent: *Sep. 9, 2025

(54) ANTIPLATELET DRUGS AND USES THEREOF

(71) Applicant: SHANGHAI CUREGENE PHARMACEUTICAL CO., LTD., Shanghai (CN)

(72) Inventors: Zi-Qiang Gu, Reston, VA (US); Yuanchao Zhang, Fulton, MD (US); Gongxin He, Shanghai (CN); Kai Hou, Shanghai (CN); Hao Wu, Shanghai (CN)

(73) Assignee: SHANGHAI CUREGENE PHARMACEUTICAL CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/018,576

(22) PCT Filed: Jul. 28, 2021

(86) PCT No.: PCT/CN2021/108875
§ 371 (c)(1),
(2) Date: Jan. 29, 2023

(87) PCT Pub. No.: WO2022/022559
PCT Pub. Date: Feb. 3, 2022

(65) Prior Publication Data
US 2024/0279178 A1    Aug. 22, 2024

(30) Foreign Application Priority Data

Jul. 29, 2020  (WO) ................ PCT/CN2020/105513

(51) Int. Cl.
*C07D 211/72*  (2006.01)
*A61K 31/445*  (2006.01)
*A61K 31/4525*  (2006.01)
*A61P 7/02*  (2006.01)
*C07D 401/12*  (2006.01)

(52) U.S. Cl.
CPC .......... *C07D 211/72* (2013.01); *A61K 31/445* (2013.01); *A61K 31/4525* (2013.01); *A61P 7/02* (2018.01); *C07D 401/12* (2013.01)

(58) Field of Classification Search
CPC ............. A61K 31/445; A61K 31/4525; A61K 9/0019; A61K 9/0053; A61P 7/02; A61P 9/10; A61P 9/00; A61P 25/00; C07D 211/72; C07D 401/12; C07D 405/12; C07D 211/96; C07B 2200/07
See application file for complete search history.

(56) References Cited

FOREIGN PATENT DOCUMENTS

| CN | 106554303 A | * | 4/2017 |
| CN | 106554368 A |   | 4/2017 |
| EP | 0934928 A1  |   | 8/1999 |

OTHER PUBLICATIONS

Bluet, G. et al.,, "Synthesis of the stabilized active metabolite of clopidogrel,", Tetrahedron, vol. 70, Apr. 18, 2014, pp. 3893-3900.
Takahashi, M. et al.,, "Quantitative determination of clopidogrel active metabolite in human plasma by LC-MS/MS,", Journal of Pharmaceutical and Biomedical Analysis, vol. 48, Aug. 23, 2008, pp. 1219-1224.
Liu, C. et al.,, "Development and validation of a sensitive and rapid UHPLC-MS/MS method for the simultaneous quantification of the common active and inactive metabolites of vicagrel and clopidogrel in human plasma,", Journal of Pharmaceutical and Biomedical Analysis, vol. 149, Nov. 6, 2017, pp. 394-402.
Furlong, M. T. et al.,, "A validated HPLC-MS/MS assay for quantifying unstable pharmacologically active metabolites of clopidogrel in human plasma: Application to a clinical pharmacokinetic study,", Journal of Chromatography B, vol. 926, Mar. 1, 2013, pp. 36-41.
Shaw, S. A. et al.,, "Synthesis of Biologically Active Piperidine Metabolites of Clopidogrel: Determination of Structure and Analyte Development,", J. Org. Chem., vol. 80, Jul. 7, 2015, pp. 7019-7032.
Farid, N. A. et al.,, "Determination of the active and inactive metabolites of prasugrel in human plasma by liquid chromatography/ tandem mass spectrometry,", Rapid Commun. Mass Spectrom., vol. 21, Dec. 31, 2007, pp. 169-179.
Hagihara, K. et al.,, "Glutaredoxin Is Involved in the Formation of the Pharmacologically Active Metabolite of Clopidogrel from Its GSH Conjugate,", Drug Metabolism and Disposition, vol. 40, No. 9, Dec. 31, 2012, pp. 1854-1859.
Delavenne, X. et al.,, "Ultra-performance LC MS/MS method for quantification of clopidogrel active metabolite,", J. Sep. Sci., vol. 33, Dec. 31, 2010, pp. 1968-1972.
Dansette, P. M. et al.,, "Metabolic Activation of Prasugrel: Nature of the Two Competitive Pathways Resulting in the Opening of Its Thiophene Ring,", Chem. Res. Toxicol., vol. 25, Apr. 6, 2012, pp. 1058-1065.
Tian, X. et al.,, "Determination of Clopidogrel and Its Active Metabolite in Human Plasma by LC-MS/MS,", Chinese Journal of Pharmaceuticals, vol. 47, No. 2, Dec. 31, 2016, pp. 202-206.
Liu, S. B. et al.,, "Determination of clopidogrel and its metabolites in plasma by UPLC-MS/MS and the application in pharmacokinetic study,", Chin. J. Pharm. Anal., vol. 35, No. 1, Dec. 31, 2015, pp. 56-63.
International Search Report of PCT/CN2021/108875, mailed on Oct. 26, 2021.
Extended European Search Report of European application No. 21851193.9, issued on Jun. 17, 2024.

* cited by examiner

*Primary Examiner* — Jean P Cornet
(74) *Attorney, Agent, or Firm* — Junhe Law Office P.C.; Zhaohui Wang

(57) ABSTRACT

The present disclosure relates to compounds which exhibit activity in the inhibition of platelet aggregation as well as pharmaceutical compositions comprising these compounds and methods of treatment of vascular diseases by administration of these compounds or the pharmaceutical compositions.

14 Claims, 3 Drawing Sheets

ANTIPLATELET DRUGS AND USES THEREOF

CROSS-REFERENCE TO RELATED APPLICATIONS

This application is a national phase application, filed pursuant to 35 U.S.C § 371 of PCT Application No. PCT/CN2021/108875 filed on Jul. 28, 2021, which claims foreign priority of PCT Application No. PCT/CN2020/105513 filed on Jul. 29, 2020, now abandoned. Each of these applications is hereby incorporated by reference herein in its entirety.

FIELD OF THE DISCLOSURE

The present disclosure generally relates to compounds which exhibit activity in the inhibition of platelet aggregation as well as pharmaceutical compositions comprising these compounds and methods of treatment by administration of these compounds or the pharmaceutical compositions.

BACKGROUND OF THE DISCLOSURE

Recently, the number of patients with vascular diseases has risen markedly. Antithrombotic agents that inhibit platelet activation play important roles in preventing the occurrence and recurrence of these diseases as well as in their treatment.

Clopidogrel is a known and widely used antithrombotic drugs worldwide, and is a prodrug that needs biotransformation to become active. After absorption, 85% of clopidogrel is hydrolysed by esterases into an inactive carboxylic acid. The remaining 15% of clopidogrel undergoes a two-step oxidation process via hepatic cytochrome P450 isoenzymes, mainly CYP2C19. The transient active thiol-metabolite specifically and irreversibly binds the platelet P2Y12 receptor.

However, clopidogrel has many shortcomings, including interpatient variability in antithrombotic effects and clopidogrel resistance in certain patients due to different expression levels of CYP2C19 in different individuals, low conversion rate to active metabolite and thus high loading dose (600 mg), slow onset of action (2 h after a loading dose), low solubility in aqueous solution and no injection formulation available for acute treatment, drug-drug interactions, etc.

Accordingly, there is a need in the art to develop improved compounds which exhibit activity in the inhibition of platelet aggregation without the shortcomings listed above.

SUMMARY OF THE DISCLOSURE

The present disclosure provides compounds which are capable of inhibiting platelet aggregation, the pharmaceutical compositions comprising these compounds and methods for the use of such compounds or pharmaceutical compositions for treatment of vascular diseases.

In one aspect, the present disclosure provides a compound having Formula (I):

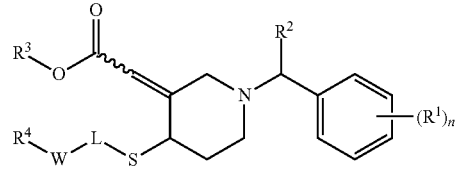

or a pharmaceutically acceptable salt thereof,
wherein

⁓⁓⁓= represents a couple bond in Z or E configuration;

$R^1$ is selected from the group consisting of hydrogen, halogen, nitro, cyano, hydroxyl, amino, alkyl, alkenyl, alkynyl, heteroalkyl, heteroalkenyl, and heteroalknyl, wherein each of alkyl, alkenyl, alkynyl, heteroalkyl, heteroalkenyl, and heteroalknyl is optionally substituted with one or more $R^a$;

$R^2$ is —C(O)$R^b$, $R^3$ is selected from the group consisting of hydrogen, alkyl, alkenyl, alkynyl, heteroalkyl, heteroalkenyl, heteroalknyl, saturated or partially unsaturated cycloalkyl, saturated or partially unsaturated heterocyclyl, aryl, and heteroaryl, wherein each of alkyl, alkenyl, alkynyl, heteroalkyl, heteroalkenyl, heteroalkynyl, cycloalkyl, heterocyclyl, aryl and heteroaryl is optionally substituted with cyano, halogen, hydroxyl, amino, alkyl, alkenyl, alkynyl, heteroalkyl, heteroalkenyl, or heteroalkynyl;

L is selected from the group consisting of a direct bond, alkyl, alkenyl, alkynyl, heteroalkyl, heteroalkenyl, heteroalknyl, saturated or partially unsaturated cycloalkyl, saturated or partially unsaturated heterocyclyl, aryl, and heteraryl, wherein each of alkyl, alkenyl, alkynyl, heteroalkyl, heteroalkenyl, heteroalknyl, cycloalkyl, heterocyclyl, aryl and heteroaryl is optionally substituted with one or more $R^f$;

W is selected from the group consisting of:

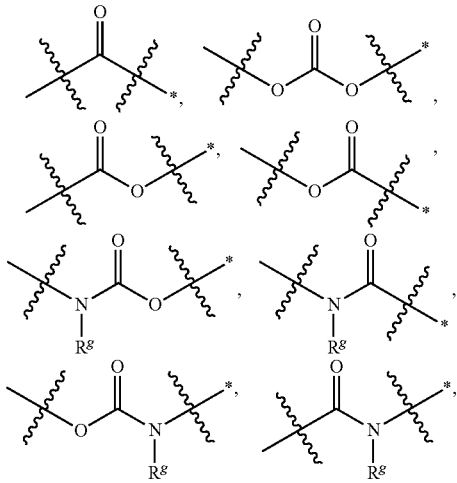

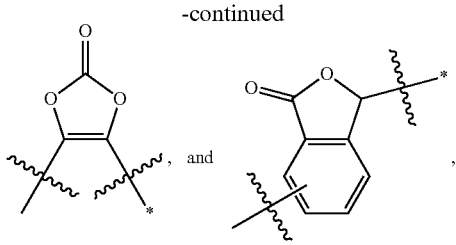

, and wherein the * end of W is connected to L;

$R^4$ is selected from the group consisting of hydrogen, alkyl, alkenyl, alkynyl, heteroalkyl, heteroalkenyl, heteroalknyl, saturated or partially unsaturated cycloalkyl, saturated or partially unsaturated heterocyclyl, aryl, and heteraryl, wherein each of alkyl, alkenyl, alkynyl, heteroalkyl, heteroalkenyl, heteroalkynyl, cycloalkyl, heterocyclyl, aryl and heteroaryl is optionally substituted with cyano, halogen, hydroxyl, amino, alkyl, alkenyl, alkynyl, heteroalkyl, heteroalkenyl, heteroalkynyl;

each of $R^a$ is independently selected from the group consisting of hydrogen, halogen, hydroxyl, amino, cyano, nitro, or $-NR^cR^d$, $R^b$ is selected from the group consisting of hydrogen, hydroxyl, alkyl, alkenyl, alkynyl, heteroalkyl, heteroalkenyl, heteroalknyl, saturated or partially unsaturated cycloalkyl, saturated or partially unsaturated heterocyclyl, aryl, heteroaryl, $-NR^cR^d$ and $-OR^e$;

each of $R^c$ and $R^d$ is independently selected from the group consisting of hydrogen, alkyl, alkenyl, alkynyl, heteroalkyl, heteroalkenyl, heteroalkynyl, aryl, and heteroaryl, wherein each of alkyl, alkenyl, alkynyl, heteroalkyl, heteroalkenyl, heteroalkynyl, aryl and heteroaryl is optionally substituted with cyano, halogen, hydroxyl, or amino;

$R^e$ is selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein each of alkyl, alkenyl, alkynyl, heteroalkyl, heteroalkenyl, heteroalkynyl, cycloalkyl, heterocyclyl, aryl and heteroaryl is optionally substituted with cyano, halogen, hydroxyl, amino, alkyl, alkenyl, alkynyl, heteroalkyl, heteroalkenyl, or heteroalkynyl;

each of $R^f$ is independently selected from the group consisting of hydrogen, cyano, halogen, hydroxyl, amino, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl; or two $R^f$ together with the atom to which they are both attached, form saturated or partially unsaturated cycloalkyl, or saturated or partially unsaturated heterocyclyl, wherein each of cycloalkyl and heterocyclyl is optionally substituted with cyano, halogen, hydroxyl, amino and alkyl;

$R^g$ is selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein each of hydrogen, alkyl, alkenyl, alkynyl, heteroalkyl, heteroalkenyl, heteroalkynyl, cycloalkyl, heterocyclyl, aryl and heteroaryl is optionally substituted with cyano, halogen, hydroxyl, or amino;

n is 0, 1, 2, 3, 4 or 5.

In some embodiments, the present disclosure provides compound having a formula selected from the group consisting of:

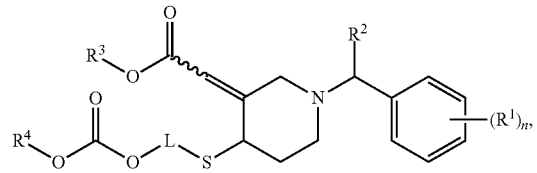

(II)

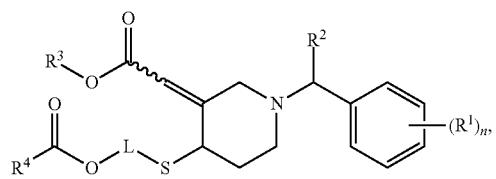

(III)

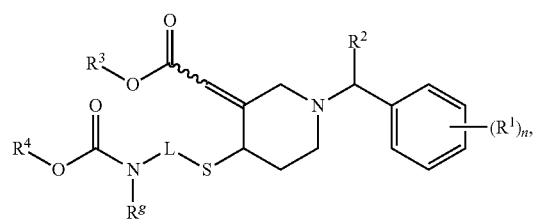

(IV)

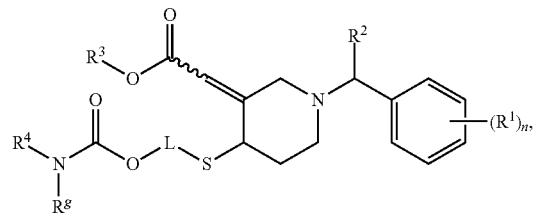

(V)

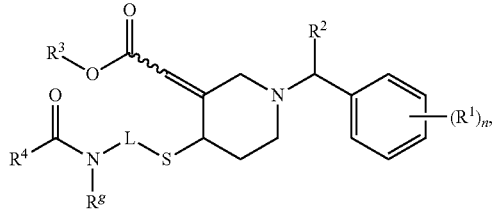

(VI)

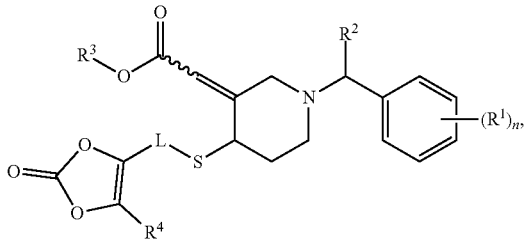

(VII)

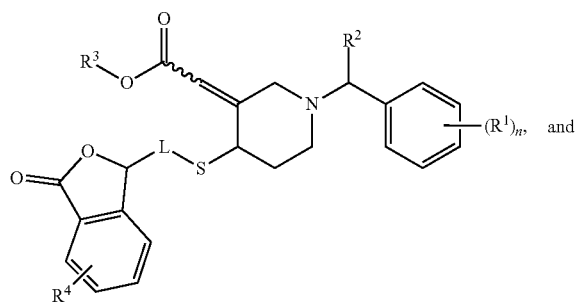

(VIII)

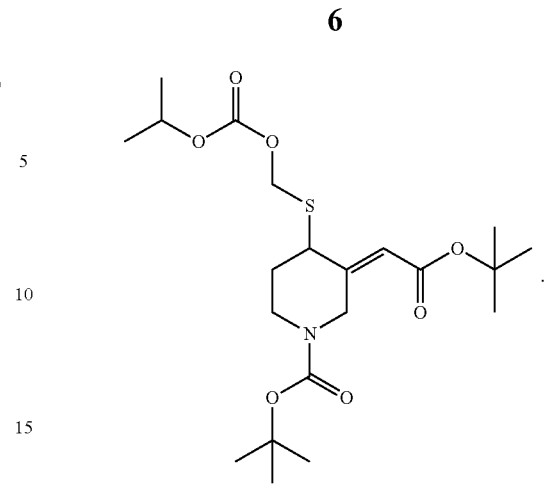

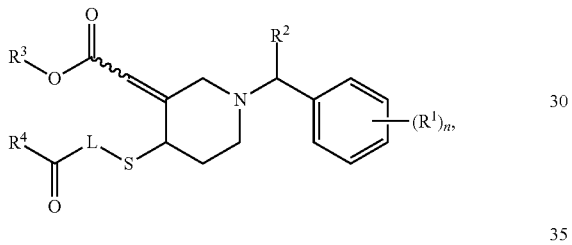

(IX)

or pharmaceutically acceptable salts thereof.

In another aspect, the present disclosure provides a pharmaceutical composition comprising the compound of the present disclosure or a pharmaceutically acceptable salt thereof, and a pharmaceutically acceptable excipient.

In a further aspect, the present disclosure provides a method for treating vascular diseases in a subject in need thereof, comprising administering an effective amount of a compound of the present disclosure or a pharmaceutically acceptable salt thereof or the pharmaceutical composition of the present disclosure to the subject.

In a further aspect, the present disclosure provides a method for inhibiting platelet aggregation in a subject in need thereof, comprising administering an effective amount of a compound of the present disclosure or a pharmaceutically acceptable salt thereof or the pharmaceutical composition of the present disclosure to a subject in need thereof.

In a further aspect, the present disclosure provides use of a compound of the present disclosure or a pharmaceutically acceptable salt thereof or the pharmaceutical composition of the present disclosure, in the manufacture of a medicament for treating vascular diseases.

In a further aspect, the present disclosure provides a compound of the present disclosure or a pharmaceutically acceptable salt thereof or the pharmaceutical composition of the present disclosure, for treating vascular diseases.

In another aspect, the present disclosure provides a compound having a formula of:

In a further aspect, the present disclosure provides a compound having a formula of:

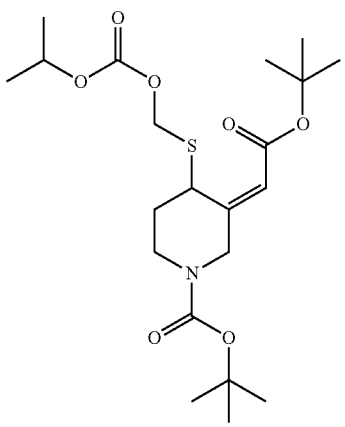

DETAILED DESCRIPTION OF THE DISCLOSURE

Figure 1:
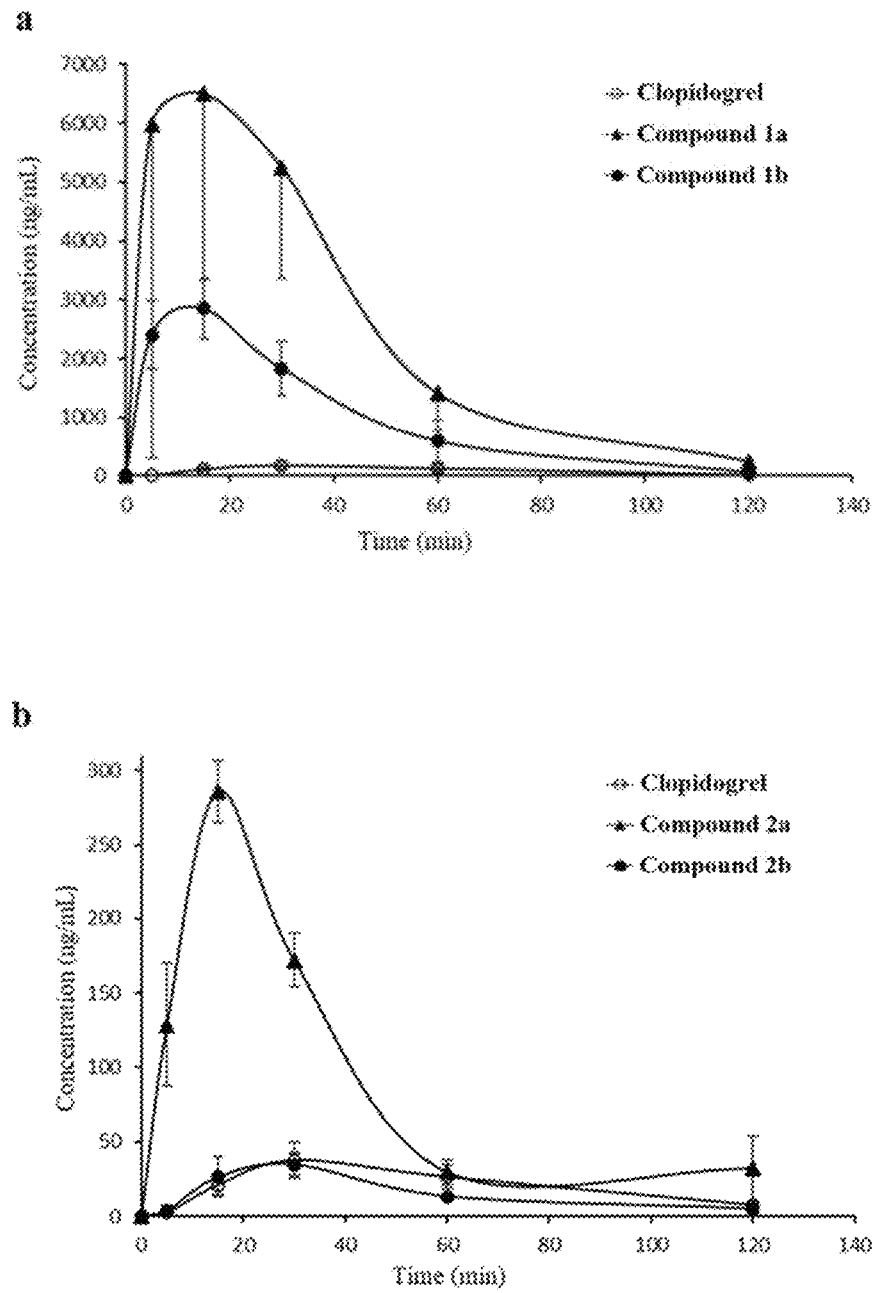
FIG. 1 shows the concentration of the active metabolite in rat plasma after oral administration of (a) clopidogrel, compound 1a and compound 1b, and (b) clopidogrel, compound 2a and compound 2b, at a dose level of 10 mg/kg.

Reference will now be made in detail to certain embodiments of the present disclosure, examples of which are illustrated in the accompanying structures and formulas. While the present disclosure will be described in conjunction with the enumerated embodiments, it will be understood that they are not intended to limit the present disclosure to those embodiments. On the contrary, the present disclosure is intended to cover all alternatives, modifications, and equivalents, which may be included within the scope of the present disclosure as defined by the claims. One skilled in the art will recognize many methods and materials similar or equivalent to those described herein, which could be used in the practice of the present disclosure. The present disclosure is in no way limited to the methods and materials described. In the event that one or more of the incorporated references and similar materials differs from or contradicts this application, including but not limited to defined terms, term usage, described techniques, or the like, the present disclosure controls. All references, patents, patent applications cited in the present disclosure are hereby incorporated by reference in their entireties.

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub-combination. It must be noted that, as used in the specification and the appended claims, the singular forms "a," "an," and "the" include plural forms of the same unless the context clearly dictates otherwise. Thus, for example, reference to "a compound" includes a plurality of compounds.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, 2$^{nd}$ Edition, University Science Books, Sausalito, 2006; Smith and March March's Advanced Organic Chemistry, 6th Edition, John Wiley & Sons, Inc., New York, 2007; Larock, Comprehensive Organic Transformations, 3$^{rd}$ Edition, VCH Publishers, Inc., New York, 2018; Carruthers, Some Modern Methods of Organic Synthesis, 4th Edition, Cambridge University Press, Cambridge, 2004; the entire contents of each of which are incorporated herein by reference.

At various places in the present disclosure, linking substituents are described. It is specifically intended that each linking substituent includes both the forward and backward forms of the linking substituent. For example, —NR(CR'R")— includes both —NR(CR'R")— and —(CR'R")NR—. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When "*" is shown adjacent to an atom of a compound, it indicates that the compound comprises such atom as an asymmetric center that is in either (R) or (S) stereo-configuration.

When any variable (e.g., $R^i$) occurs more than one time in any constituent or formula for a compound, its definition at each occurrence is independent of its definition at every other occurrence. Thus, for example, if a group is shown to be substituted with 0-2 $R^i$ moieties, then the group may optionally be substituted with up to two $R^i$ moieties and $R^i$ at each occurrence is selected independently from the definition of $R^i$. Also, combinations of substituents and/or variables are permissible, but only if such combinations result in stable compounds.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, particularly 1 to 10, particularly 1 to 8, particularly 1 to 6, particularly 1 to 5, particularly 1 to 4, particularly 1 to 3 or particularly 1 to 2 carbon atoms.

As used herein, the term "alkyl", whether as part of another term or used independently, refers to a saturated linear or branched-chain hydrocarbon radical, which may be optionally substituted independently with one or more substituents described below. The term "$C_{i-j}$ alkyl" refers to an alkyl having i to j carbon atoms. In some embodiments, alkyl groups contain 1 to 10 carbon atoms. In some embodiments, alkyl groups contain 1 to 9 carbon atoms. In some embodiments, alkyl groups contain 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of "$C_{1-10}$ alkyl" include, but are not limited to, methyl, ethyl, propyl, butyl, pentyl, hexyl, heptyl, octyl, nonyl, and decyl. Examples of "$C_{1-6}$ alkyl" are methyl, ethyl, n-propyl, isopropyl, n-butyl, i-butyl, s-butyl, t-butyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like.

As used herein, the term "alkenyl", whether as part of another term or used independently, refers to linear or branched-chain hydrocarbon radical having at least one carbon-carbon double bond, which may be optionally substituted independently with one or more substituents described herein, and includes radicals having "cis" and "trans" orientations, or alternatively, "E" and "Z" orientations. In some embodiments, alkenyl groups contain 2 to 12 carbon atoms. In some embodiments, alkenyl groups contain 2 to 11 carbon atoms. In some embodiments, alkenyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkenyl groups contain 2 carbon atoms. Examples of alkenyl group include, but are not limited to, ethylenyl (or vinyl), propenyl (allyl), butenyl, pentenyl, 1-methyl-2 buten-1-yl, 5-hexenyl, and the like.

As used herein, the term "alkynyl", whether as part of another term or used independently, refers to a linear or branched hydrocarbon radical having at least one carbon-carbon triple bond, which may be optionally substituted independently with one or more substituents described herein. In some embodiments, alkenyl groups contain 2 to 12 carbon atoms. In some embodiments, alkynyl groups contain 2 to 11 carbon atoms. In some embodiments, alkynyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkynyl groups contain 2 carbon atoms. Examples of alkynyl group include, but are not limited to, ethynyl, 1-propynyl, 2-propynyl, and the like.

As used herein, the term "amino" refers to —NH$_2$ group. Amino groups may also be substituted with one or more groups such as alkyl, aryl, carbonyl or other amino groups.

As used herein, the term "aryl", whether as part of another term or used independently, refers to monocyclic and polycyclic ring systems having a total of 5 to 20 ring members, wherein at least one ring in the system is aromatic and wherein each ring in the system contains 3 to 12 ring members. Examples of "aryl" include, but are not limited to, phenyl, biphenyl, naphthyl, anthracyl and the like, which may bear one or more substituents. Also included within the scope of the term "aryl", as it is used herein, is a group in which an aromatic ring is fused to one or more additional rings. In the case of polycyclic ring system, only one of the rings needs to be aromatic (e.g., 2,3-dihydroindole), although all of the rings may be aromatic (e.g., quinoline). The second ring can also be fused or bridged. Examples of polycyclic aryl include, but are not limited to, benzofuranyl, indanyl, phthalimidyl, naphthimidyl, phenanthridinyl, or tetrahydronaphthyl, and the like. Aryl groups can be substituted at one or more ring positions with substituents as described above.

As used herein, the term "cycloalkyl", whether as part of another term or used independently, refer to a monovalent non-aromatic, saturated or partially unsaturated monocyclic and polycyclic ring system, in which all the ring atoms are carbon and which contains at least three ring forming carbon atoms. In some embodiments, the cycloalkyl may contain 3 to 12 ring forming carbon atoms, 3 to 10 ring forming carbon atoms, 3 to 9 ring forming carbon atoms, 3 to 8 ring forming carbon atoms, 3 to 7 ring forming carbon atoms, 3 to 6 ring forming carbon atoms, 3 to 5 ring forming carbon atoms, 4 to 12 ring forming carbon atoms, 4 to 10 ring forming carbon atoms, 4 to 9 ring forming carbon atoms, 4 to 8 ring forming carbon atoms, 4 to 7 ring forming carbon atoms, 4 to 6 ring forming carbon atoms, 4 to 5 ring forming carbon atoms. Cycloalkyl groups may be saturated or partially unsaturated. Cycloalkyl groups may be substituted. In some embodiments, the cycloalkyl group may be a saturated cyclic alkyl group. In some embodiments, the cycloalkyl group may be a partially unsaturated cyclic alkyl group that contains at least one double bond or triple bond in its ring system. In some embodiments, the cycloalkyl group may be monocyclic or polycyclic. Examples of monocyclic cycloalkyl group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Examples of polycyclic cycloalkyl group include, but are not limited to, adamantyl, norbornyl, fluorenyl, spiro-pentadienyl, spiro[3.6]-decanyl, bicyclo[1,1,1]pentenyl, bicyclo[2,2,1]heptenyl, and the like.

As used herein, the term "cyano" refers to —CN.

As used herein, the term "halogen" refers to an atom selected from fluorine (or fluoro), chlorine (or chloro), bromine (or bromo) and iodine (or iodo).

As used herein, the term "heteroatom" refers to nitrogen, oxygen, sulfur, or phosphorus, and includes any oxidized form of nitrogen or sulfur, and any quaternized form of a basic nitrogen (including N-oxides).

As used herein, the term "heteroalkenyl" refers to an alkenyl, at least one of the carbon atoms of which is replaced with a heteroatom selected from N, O, or S. The heteroalkenyl may be a carbon radical or heteroatom radical (i.e., the heteroatom may appear in the middle or at the end of the radical), and may be optionally substituted independently with one or more substituents described herein.

As used herein, the term "heteroalkynyl" refers to an alkynyl, at least one of the carbon atoms of which is replaced with a heteroatom selected from N, O, or S. The heteroalkynyl may be a carbon radical or heteroatom radical (i.e., the heteroatom may appear in the middle or at the end of the radical), and may be optionally substituted independently with one or more substituents described herein.

As used herein, the term "heteroaryl", whether as part of another term or used independently, refers to an aryl group having, in addition to carbon atoms, one or more heteroatoms. The heteroaryl group can be monocyclic. Examples of monocyclic heteroaryl include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The heteroaryl group also includes polycyclic groups in which a heteroaromatic ring is fused to one or more aryl, cycloaliphatic, or heterocyclyl rings, where the radical or point of attachment is on the heteroaromatic ring. Examples of polycyclic heteroaryl include, but are not limited to, indolyl, isoindolyl, benzothienyl, benzofuranyl, benzo[1,3]dioxolyl, dibenzofuranyl, indazolyl, benzimidazolyl, benzthiazolyl, quinolyl, isoquinolyl, dihydroquinolinyl, dihydroisoquinolinyl, tetrahydroquinolinyl, tetrahydroisoquinolinyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and the like.

As used herein, the term "heterocyclyl" refers to a saturated or partially unsaturated carbocyclyl group in which one or more ring atoms are heteroatoms independently selected from oxygen, sulfur, nitrogen, phosphorus, and the like, the remaining ring atoms being carbon, wherein one or more ring atoms may be optionally substituted independently with one or more substituents. In some embodiments, the heterocyclyl is a saturated heterocyclyl. In some embodiments, the heterocyclyl is a partially unsaturated heterocyclyl having one or more double bonds in its ring system. In some embodiments, the heterocyclyl may contains any oxidized form of carbon, nitrogen or sulfur, and any quaternized form of a basic nitrogen. "Heterocyclyl" also includes radicals wherein the heterocyclyl radicals are fused with a saturated, partially unsaturated, or fully unsaturated (i.e., aromatic) carbocyclic or heterocyclic ring. The heterocyclyl radical may be carbon linked or nitrogen linked where such is possible. In some embodiments, the heterocycle is carbon linked. In some embodiments, the heterocycle is nitrogen linked. For example, a group derived from pyrrole may be pyrrol-1-yl (nitrogen linked) or pyrrol-3-yl (carbon linked). Further, a group derived from imidazole may be imidazol-1-yl (nitrogen linked) or imidazol-3-yl (carbon linked).

In some embodiments, the term "3- to 12-membered heterocyclyl" refers to a 3- to 12-membered saturated or partially unsaturated monocyclic or polycyclic heterocyclic ring system having 1 to 3 heteroatoms independently selected from nitrogen, oxygen, or sulfur. The fused, spiro and bridged ring systems are also included within the scope of this definition. Examples of monocyclic heterocyclyl include, but are not limited to oxetanyl, 1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperazinyl, piperidinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, pyrrolidinyl, triazinonyl, and the like. Examples of fused heterocyclyl include, but are not limited to, phenyl fused ring or pyridinyl fused ring, such as quinolinyl, isoquinolinyl, tetrahydroquinolinyl, tetrahydroisoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of spiro heterocyclyl include, but are not limited to, spiropyranyl, spirooxazinyl, and the like. Examples of bridged heterocyclyl include, but are not limited to, morphanyl, hexamethylenetetraminyl, 3-aza-bicyclo[3.1.0]hexane, 8-aza-bicyclo[3.2.1]octane, 1-aza-bicyclo[2.2.2]octane, 1,4-diazabicyclo[2.2.2]octane (DABCO), and the like.

As used herein, the term "hydroxyl" refers to —OH.

As used herein, the term "partially unsaturated" refers to a radical that includes at least one double or triple bond. The term "partially unsaturated" is intended to encompass rings having multiple sites of unsaturation, but is not intended to include aromatic (i.e., fully unsaturated) moieties.

As used herein, the term "substituted", whether preceded by the term "optionally" or not, means that one or more hydrogens of the designated moiety are replaced with a suitable substituent. It will be understood that "substitution" or "substituted with" includes the implicit proviso that such substitution is in accordance with permitted valence of the substituted atom and that the substitution results in a stable or chemically feasible compound, e.g., which does not spontaneously undergo transformation such as by rearrangement, cyclization, elimination, etc. Unless otherwise indicated, an "optionally substituted" group may have a suitable substituent at each substitutable position of the group, and when more than one position in any given structure may be substituted with more than one substituent selected from a specified group, the substituent may be either the same or different at every position. It will be understood by those skilled in the art that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

Compounds

The present disclosure provides novel compounds of Formula (I) and pharmaceutically acceptable salts thereof, synthetic methods for making the compounds, pharmaceutical compositions containing them and various uses of the disclosed compounds.

In one aspect, the present disclosure provides a compound having Formula (I):

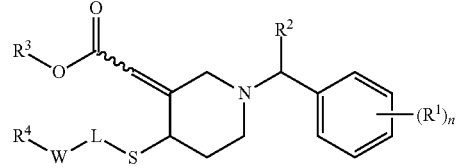

or a pharmaceutically acceptable salt thereof,
wherein represents a double bond in Z or E configuration;

$R^1$ is selected from the group consisting of hydrogen, halogen, nitro, cyano, hydroxyl, amino, alkyl, alkenyl, alkynyl, heteroalkyl, heteroalkenyl, and heteroalknyl, wherein each of alkyl, alkenyl, alkynyl, heteroalkyl, heteroalkenyl, and heteroalknyl is optionally substituted with one or more $R^a$;

$R^2$ is —C(O)$R^b$;

$R^3$ is selected from the group consisting of hydrogen, alkyl, alkenyl, alkynyl, heteroalkyl, heteroalkenyl, heteroalknyl, saturated or partially unsaturated cycloalkyl, saturated or partially unsaturated heterocyclyl, aryl, and heteroaryl, wherein each of alkyl, alkenyl, alkynyl, heteroalkyl, heteroalkenyl, heteroalkynyl, cycloalkyl, heterocyclyl, aryl and heteroaryl is optionally substituted with cyano, halogen, hydroxyl, amino, alkyl, alkenyl, alkynyl, heteroalkyl, heteroalkenyl, or heteroalkynyl;

L is selected from the group consisting of a direct bond, alkyl, alkenyl, alkynyl, heteroalkyl, heteroalkenyl, heteroalknyl, saturated or partially unsaturated cycloalkyl, saturated or partially unsaturated heterocyclyl, aryl, and heteraryl, wherein each of alkyl, alkenyl, alkynyl, heteroalkyl, heteroalkenyl, heteroalknyl, cycloalkyl, heterocyclyl, aryl and heteroaryl is optionally substituted with one or more $R^f$, W is selected from the group consisting of:

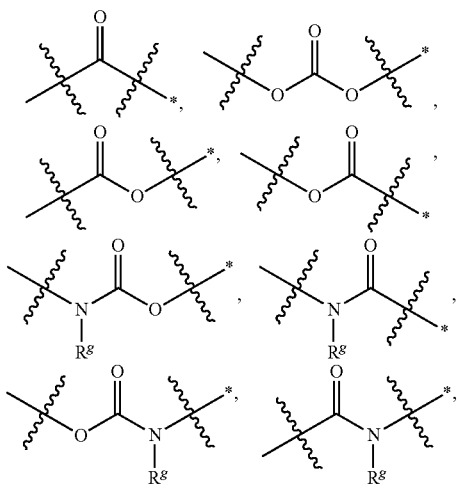

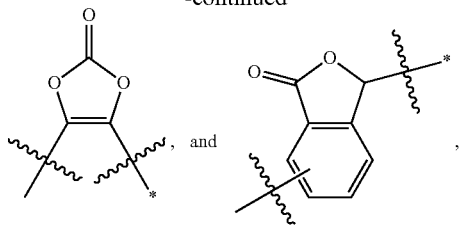

wherein the * end of W is connected to L;

$R^4$ is selected from the group consisting of hydrogen, alkyl, alkenyl, alkynyl, heteroalkyl, heteroalkenyl, heteroalknyl, saturated or partially unsaturated cycloalkyl, saturated or partially unsaturated heterocyclyl, aryl, and hetraryl, wherein each of alkyl, alkenyl, alkynyl, heteroalkyl, heteroalkenyl, heteroalkynyl, cycloalkyl, heterocyclyl, aryl and heteroaryl is optionally substituted with cyano, halogen, hydroxyl, amino, alkyl, alkenyl, alkynyl, heteroalkyl, heteroalkenyl, heteroalkynyl;

each of $R^a$ is independently selected from the group consisting of hydrogen, halogen, hydroxyl, amino, cyano, nitro, or —$NR^cR^d$, $R^b$ is selected from the group consisting of hydrogen, hydroxyl, alkyl, alkenyl, alkynyl, heteroalkyl, heteroalkenyl, heteroalknyl, saturated or partially unsaturated cycloalkyl, saturated or partially unsaturated heterocyclyl, aryl, hetaryl, —$NR^cR^d$ and —$OR^e$;

each of $R^c$ and $R^d$ is independently selected from the group consisting of hydrogen, alkyl, alkenyl, alkynyl, heteroalkyl, heteroalkenyl, heteroalkynyl, aryl, and heteroaryl, wherein each of alkyl, alkenyl, alkynyl, heteroalkyl, heteroalkenyl, heteroalkynyl, aryl and heteroaryl is optionally substituted with cyano, halogen, hydroxyl, or amino;

$R^e$ is selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl, wherein each of alkyl, alkenyl, alkynyl, heteroalkyl, heteroalkenyl, heteroalkynyl, cycloalkyl, heterocyclyl, aryl and heteroaryl is optionally substituted with cyano, halogen, hydroxyl, amino, alkyl, alkenyl, alkynyl, heteroalkyl, heteroalkenyl, or heteroalkynyl;

each of $R^f$ is independently selected from the group consisting of hydrogen, cyano, halogen, hydroxyl, amino, alkyl, alkenyl, alkynyl, heteroalkyl, heteroalkenyl, heteroalkynyl, saturated or partially unsaturated cycloalkyl, saturated or partially unsaturated heterocyclyl, aryl, and heteroaryl; or two $R^f$ together with the atom to which they are both attached, form saturated or partially unsaturated cycloalkyl, or saturated or partially unsaturated heterocyclyl, wherein each of cycloalkyl and heterocyclyl is optionally substituted with cyano, halogen, hydroxyl, amino and alkyl;

$R^g$ is selected from the group consisting of hydrogen, alkyl, alkenyl, alkynyl, heteroalkyl, heteroalkenyl, heteroalkynyl, saturated or partially unsaturated cycloalkyl, or saturated or partially unsaturated heterocyclyl, aryl, and heteroaryl, wherein each of hydrogen, alkyl, alkenyl, alkynyl, heteroalkyl, heteroalkenyl, heteroalkynyl, cycloalkyl, heterocyclyl, aryl and heteroaryl is optionally substituted with cyano, halogen, hydroxy, or amino;

n is 0, 1, 2, 3, 4 or 5.

In some embodiments, $R^1$ is selected from the group consisting of hydrogen, halogen, nitro, cyano, hydroxy, amino, alkyl, and heteroalkyl, wherein each of alkyl and heteroalkyl is optionally substituted with one or more $R^a$.

In certain embodiments, each of $R^a$ is independently selected from the group consisting of halogen, hydroxyl, cyano and nitro.

In some embodiments, $R^1$ is halogen, cyano, hydroxyl, amino, or alkyl optionally substituted with one or more $R^a$.

In certain embodiments, $R^1$ is halogen, cyano, or alkyl optionally substituted with one or more $R^a$.

In certain embodiments, $R^1$ is fluoro, chloro, bromo, cyano, methyl or trifluoromethyl.

In some embodiments, n is 1, 2 or 3. In certain embodiments, n is 1 or 2. In certain embodiments, n is 1.

In some embodiments, $R^2$ is —$C(O)R^b$, wherein $R^b$ is selected from the group consisting of hydrogen, hydroxyl, alkyl, alkenyl, alkynyl, heteroalkyl, heteroalkenyl, heteroalknyl, saturated or partially unsaturated cycloalkyl, saturated or partially unsaturated heterocycloalkyl, —$NR^cR^d$ and —$OR^e$.

In certain embodiments, each of $R^c$ and $R^d$ is independently selected from the group consisting of hydrogen, alkyl, and alkenyl, wherein each of alkyl, and alkenyl is optionally substituted with halogen or hydroxyl.

In certain embodiments, $R^e$ is selected from the group consisting of alkyl, alkenyl, heteroalkyl, heteroalkenyl, aryl, and heteroaryl, wherein each of alkyl, alkenyl, heteroalkyl, heteroalkenyl, aryl and heteroaryl is optionally substituted with cyano, halogen, hydroxy, amino, or alkyl.

In some embodiments, $R^2$ is —$C(O)R^b$, wherein $R^b$ is hydrogen, hydroxyl, alkyl, saturated or partially unsaturated cycloalkyl, or —$OR^e$.

In certain embodiments, $R^2$ is —$C(O)R^b$, wherein $R^b$ is saturated cycloalkyl or —$OR^e$, and $R^e$ is alkyl.

In certain embodiments, $R^2$ is —$C(O)R^b$, wherein $R^b$ is saturated $C_{3-6}$ cycloalkyl or —$OR^e$, and $R^e$ is $C_{1-6}$ alkyl.

In certain embodiments, $R^2$ is —$C(O)R^b$, wherein $R^b$ is cyclopropyl or —$OR^e$, and $R^e$ is methyl, ethyl, n-propyl or isopropyl.

In some embodiments, $R^2$ is —$C(O)$-cyclopropyl or —$C(O)OCH_3$.

In some embodiments, $R^3$ is hydrogen or alkyl optionally substituted with halogen, hydroxyl, cyano or amino.

In some embodiments, $R^3$ is hydrogen.

In some embodiments, $R^3$ is alkyl optionally substituted with halogen, hydroxyl, cyano or amino.

In certain embodiments, $R^3$ is $C_{1-6}$ alkyl optionally substituted with halogen, hydroxyl, cyano or amino.

In certain embodiments, $R^3$ is methyl, ethyl, n-propyl, or isopropyl.

In some embodiments, L is selected from the group consisting of a direct bond, alkyl, heteroalkyl, saturated or partially unsaturated cycloalkyl, and saturated or partially unsaturated heterocyclyl, wherein each of alkyl, heteroalkyl, cycloalkyl and heterocyclyl is optionally substituted with one or more $R^f$.

In certain embodiments, each of $R^f$ is independently selected from the group consisting of hydrogen, halogen, hydroxyl, amino, alkyl, and heteroalkyl.

In certain embodiments, two $R^f$ together with the atom to which they are both attached, form saturated or partially unsaturated cycloalkyl optionally substituted with cyano, halogen, hydroxyl, amino and alkyl.

In some embodiments, L is a direct bond.

In some embodiments, L is alkyl optionally substituted with one or more $R^f$.

In certain embodiments, L is $C_{1-6}$ alkyl optionally substituted with one or more $R^f$.

In certain embodiments, L is $C_{1-6}$ alkyl optionally substituted with one or more $R^f$, wherein each of $R^f$ is independently selected from the group consisting of hydrogen, halogen, hydroxyl, methyl and ethyl.

In some embodiments, L is —$CH_2$—, —$CH(CH_3)$—, or —$C(CH_3)_2$—.

In some embodiments, W is

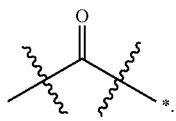 [SMILES: *C(*)=O]

In some embodiments, W is

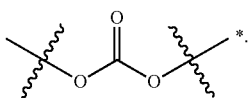 [SMILES: *OC(=O)O*]

In some embodiments, W is

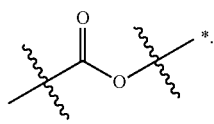 [SMILES: *OC(*)=O]

In some embodiments, W is

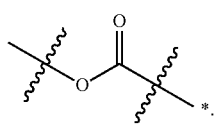 [SMILES: *OC(*)=O]

In some embodiments, W is

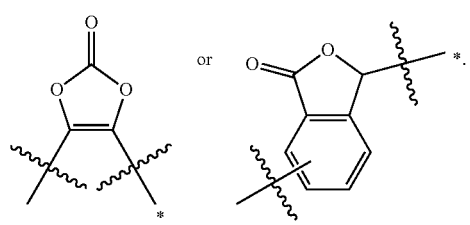

In some embodiments, W is

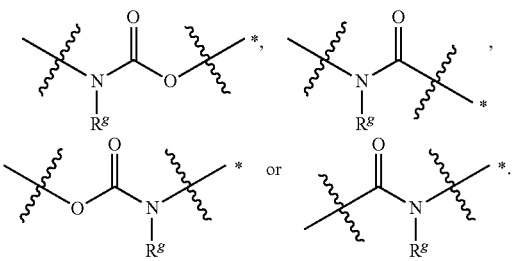

In some embodiments, $R^g$ is selected from the group consisting of hydrogen, alkyl and heteroalkyl, wherein each of alkyl and heteroalkyl is optionally substituted with halogen, hydroxyl, cyano, or amino.

In certain embodiments, W is

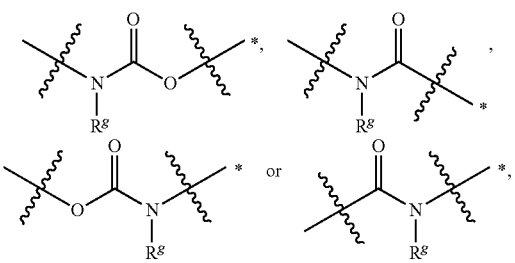

wherein $R^g$ is hydrogen or $C_{1-6}$ alkyl. In certain embodiments, $R^g$ is hydrogen, methyl or ethyl.

In some embodiments, $R^4$ is hydrogen, alkyl, alkenyl, alkynyl, heteroalkyl, heteroalkenyl, heteroalkynyl or aryl, wherein each of alkyl, alkenyl, alkynyl, heteroalkyl, heteroalkenyl, heteroalkynyl and aryl is optionally substituted with cyano, halogen, hydroxyl, amino, or alkyl.

In certain embodiments, $R^4$ is hydrogen, alkyl or aryl optionally substituted with halogen, hydroxyl, cyano or amino.

In certain embodiments, $R^4$ is hydrogen, $C_{1-6}$ alkyl optionally substituted with halogen, hydroxyl, cyano or amino, $C_{6-12}$ aryl optionally substituted with halogen, hydroxyl, cyano or amino.

In certain embodiments, $R^4$ is hydrogen, —$CH_3$, —$CH_2CH_3$, —$CH(CH_3)_2$, —$C(CH_3)_3$, —$CH(CH_3)(NH_2)$, or phenyl.

In some embodiments, is a double bond in E configuration.

In some embodiments, is a double bond in Z configuration.

In a further aspect, the present disclosure provides a compound having a formula selected from the group consisting of:

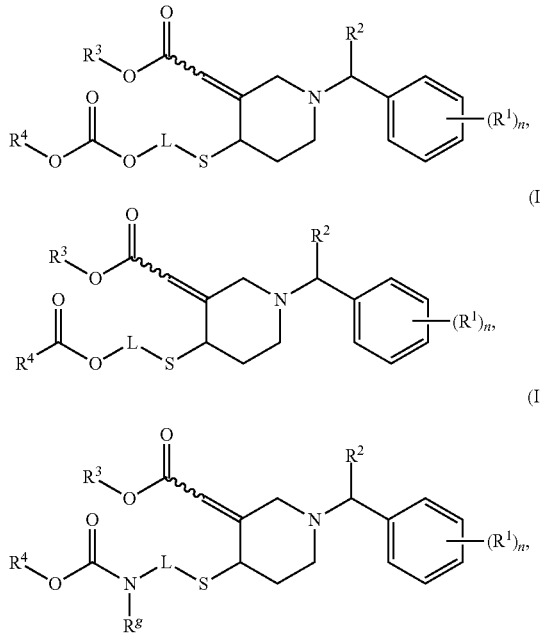

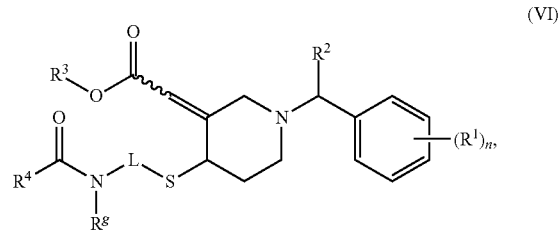

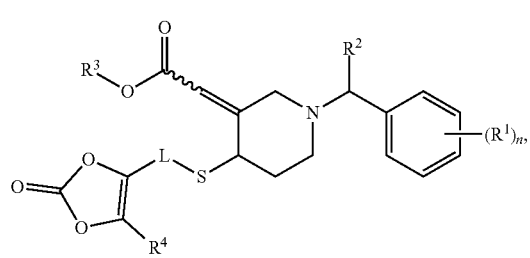

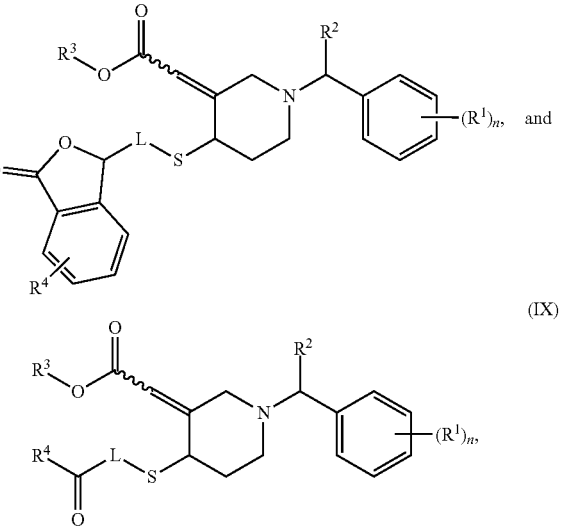

or a pharmaceutically acceptable salt thereof, wherein $R^1$, $R^2$, $R^3$, $R^4$, $R^g$, L and n are defined as supra.

In some embodiments, $R^1$ is halogen. In certain embodiments, $R^1$ is fluoro, chloro or bromo.

In some embodiments, n is 1, 2 or 3. In certain embodiments, n is 1 or 2. In certain embodiments, n is 1.

In some embodiments, $R^2$ is —C(O)$R^b$, wherein $R^b$ is hydrogen, hydroxyl, alkyl, saturated cycloalkyl or —OR$^e$. In certain embodiments, $R^2$ is —C(O)$R^b$, wherein $R^b$ is saturated cycloalkyl or —OR$^e$, and $R^e$ is alkyl. In certain embodiments, $R^2$ is —C(O)$R^b$, wherein $R^b$ is saturated $C_{3-6}$ cycloalkyl or —OR$^e$, and $R^e$ is $C_{1-6}$ alkyl. In certain embodiments, $R^2$ is —C(O)$R^b$, wherein $R^b$ is cyclopropyl or —OR$^e$, and $R^e$ is methyl, ethyl, n-propyl or isopropyl. In certain embodiments, $R^2$ is —C(O)— cyclopropyl or —C(O)OCH$_3$.

In some embodiments, $R^3$ is hydrogen.

In some embodiments, $R^3$ is alkyl. In certain embodiments, $R^3$ is $C_{1-6}$ alkyl. In certain embodiments, $R^3$ is methyl, ethyl, n-propyl, or isopropyl.

In some embodiments, L is a direct bond.

In some embodiments, L is alkyl optionally substituted with one or more $R^f$ independently selected from hydrogen, halogen, hydroxyl, methyl and ethyl. In certain embodiments, L is $C_{1-6}$ alkyl optionally substituted with one or more $R^f$ independently selected from hydrogen, halogen, hydroxyl, methyl and ethyl. In certain embodiments, L is —CH$_2$—, —CH(CH$_3$)—, or —C(CH$_3$)$_2$—.

In some embodiments, $R^4$ is hydrogen or alkyl optionally substituted with halogen, hydroxyl, cyano or amino. In certain embodiments, $R^4$ is hydrogen or $C_{1-6}$ alkyl optionally substituted with halogen, hydroxyl, cyano or amino. In certain embodiments, $R^4$ is hydrogen, —CH$_3$, —CH$_2$CH$_3$, —CH(CH$_3$)$_2$, —C(CH$_3$)$_3$, or —CH(CH$_3$)(NH$_2$).

In some embodiments, $R^g$ is hydrogen or alkyl. In certain embodiments, R& is hydrogen or $C_{1-6}$ alkyl. In certain embodiments, $R^g$ is hydrogen, methyl, or ethyl. In certain embodiments, $R^g$ is hydrogen.

In some embodiments, $$\mathrel{\vcenter{\hbox{$\sim\!\!\!\!\!=$}}}$$

is a double bond in E configuration.

In some embodiments,

is a double bond in Z configuration.

In a further aspect, the present disclosure provides a compound having a formula selected from the group consisting of:

(IIa)

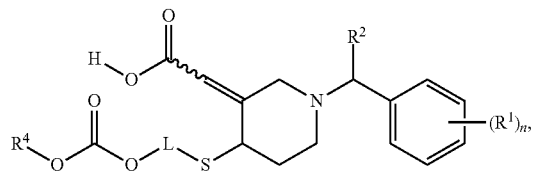

(IIIa)

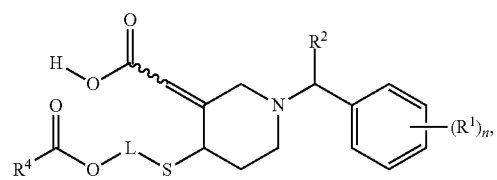

(IVa)

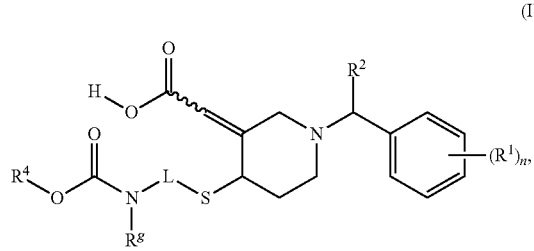

(Va)

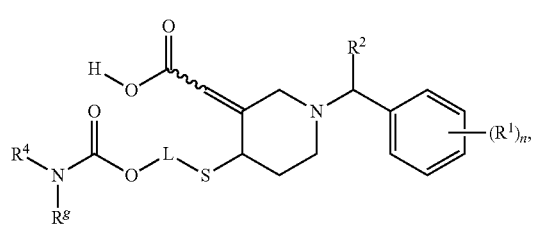

(VIa)

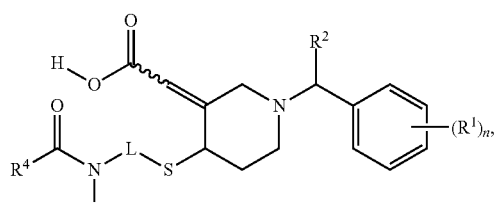

(VIIa)

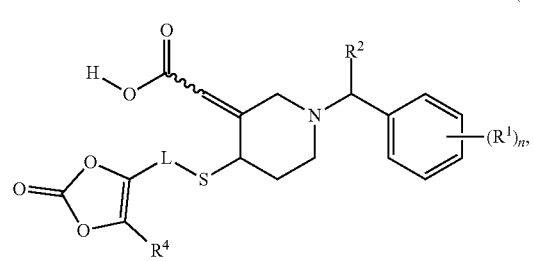

(VIIIa)

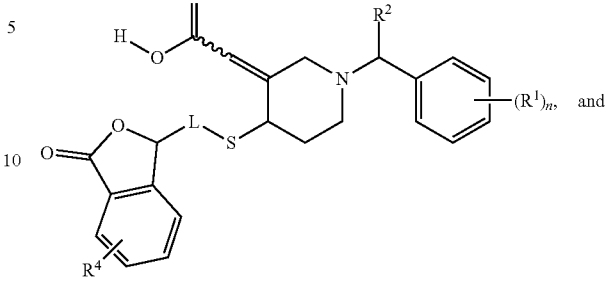 and (IXa)

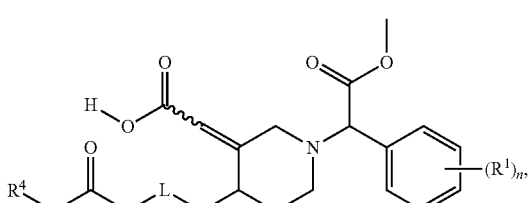

or a pharmaceutically acceptable salt thereof, wherein $R^1$, $R^2$, $R^4$, $R^g$, L and n are defined as supra.

In some embodiments,

is a double bond in E configuration.

In some embodiments,

is a double bond in Z configuration.

In a further aspect, the present disclosure provides a compound having a formula selected from the group consisting of:

(IIb)

-continued
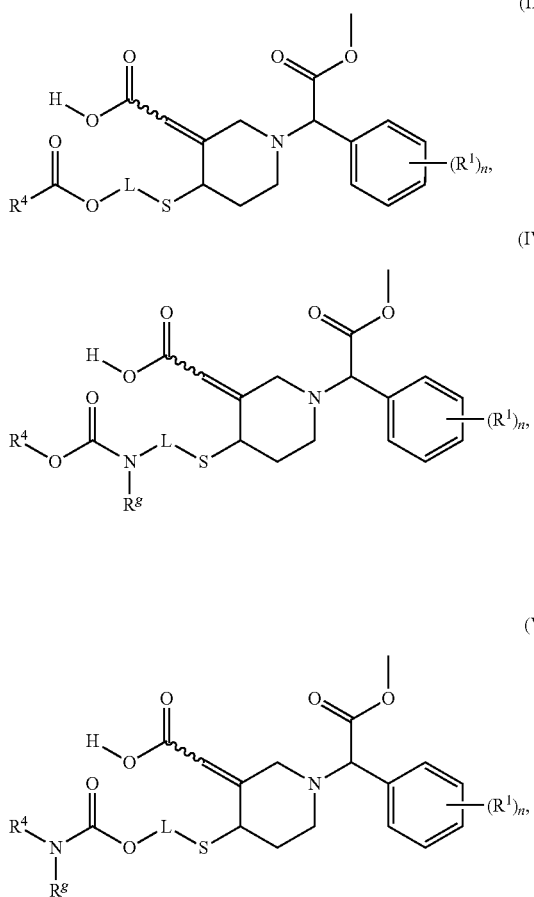
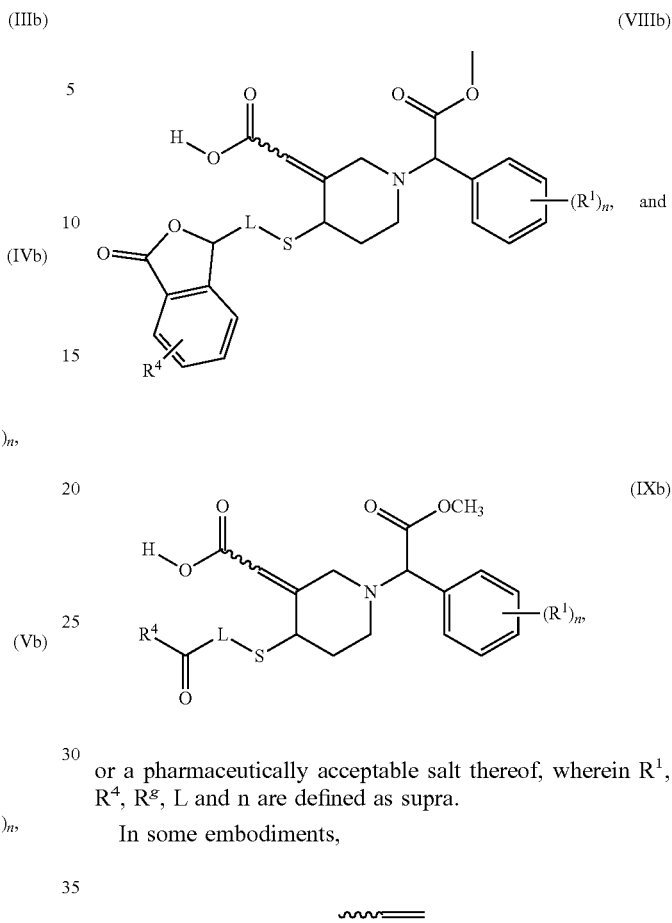
or a pharmaceutically acceptable salt thereof, wherein $R^1$, $R^4$, $R^g$, L and n are defined as supra.
In some embodiments,
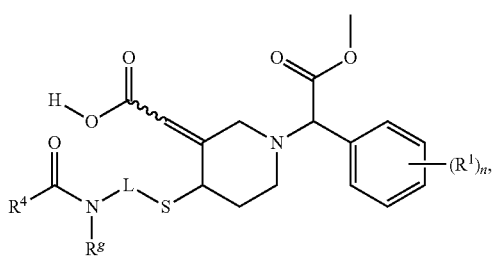
is a double bond in E configuration.
In some embodiments,
is a couple Dona in Z configuration.
In a further aspect, the present disclosure provides a compound having a formula selected from the group consisting of:
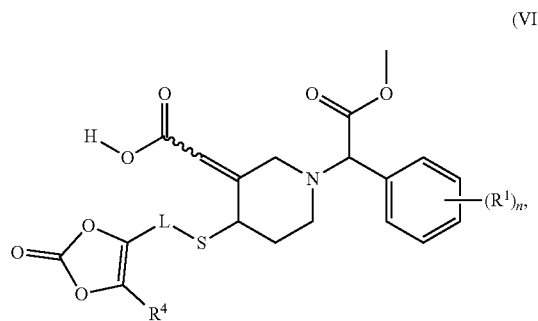
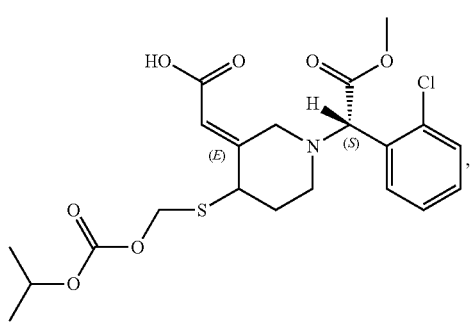

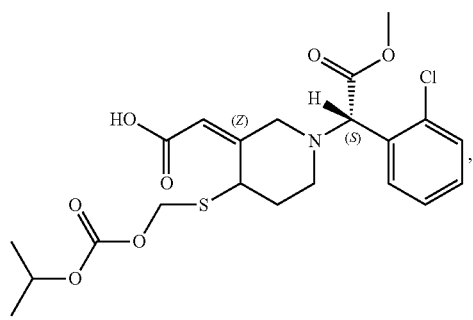
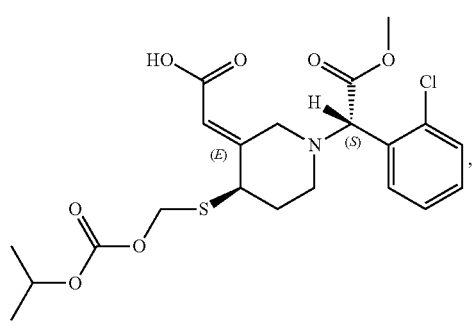
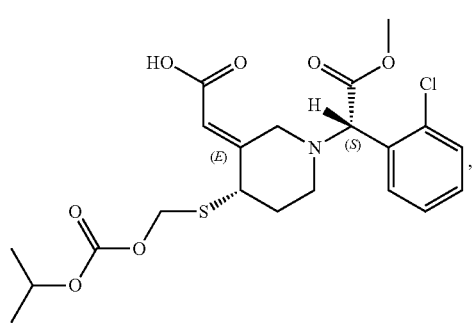
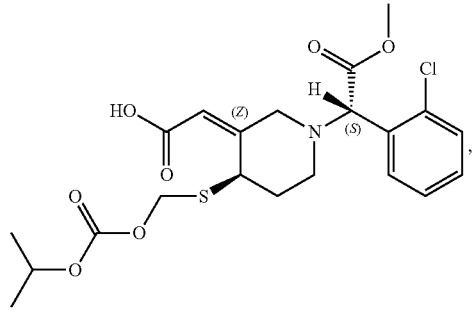
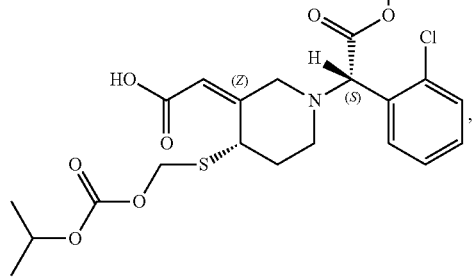
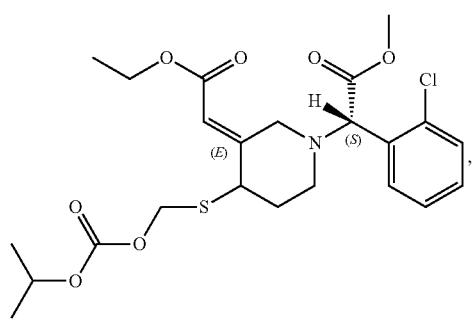
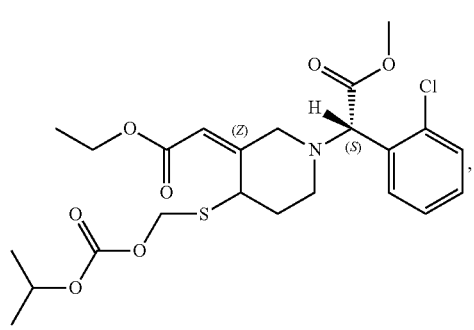
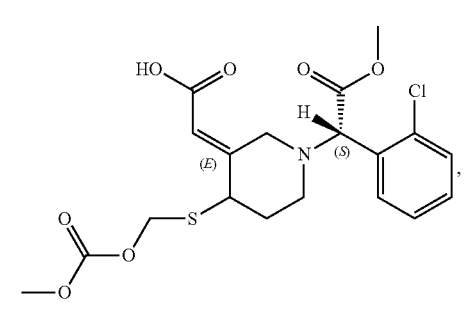
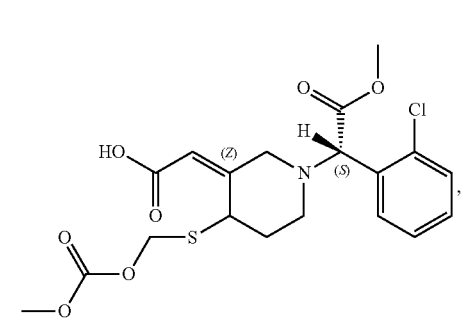
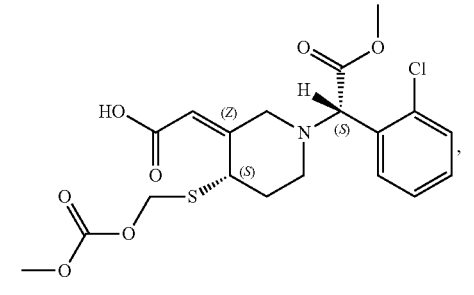

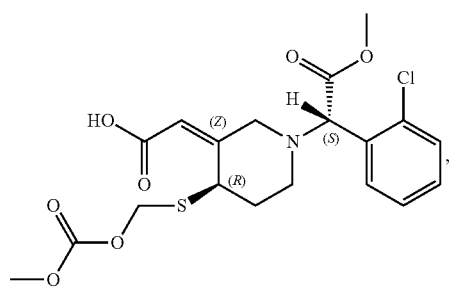
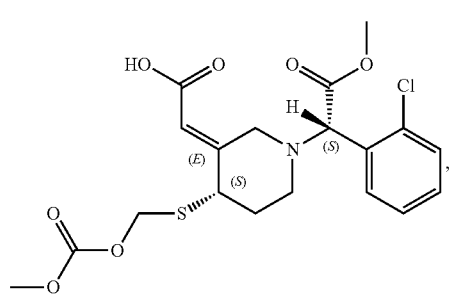
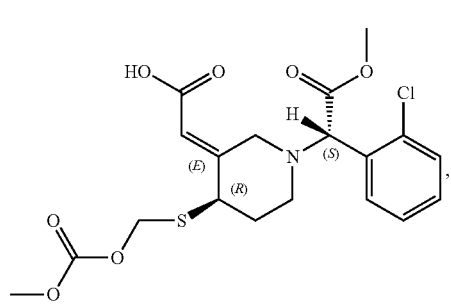
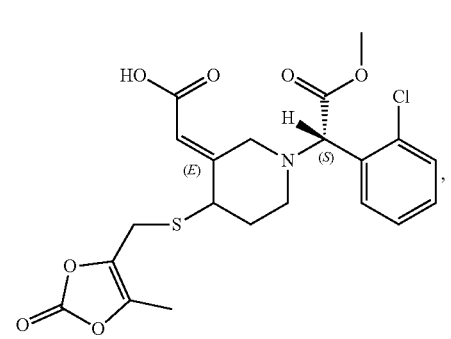
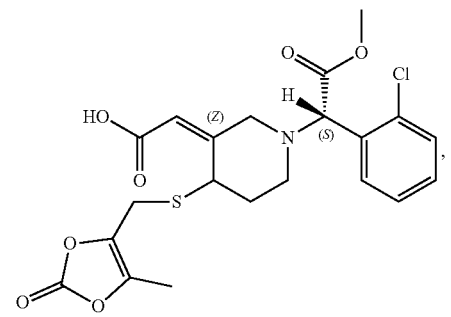
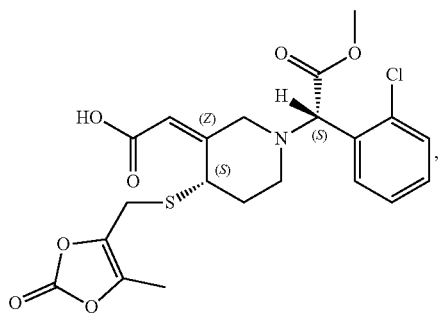
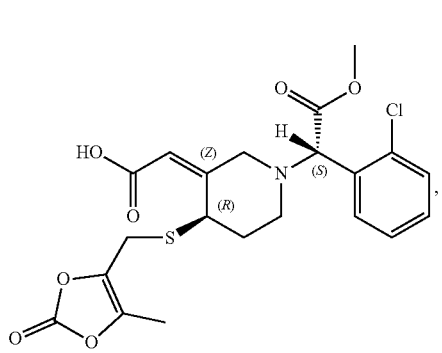
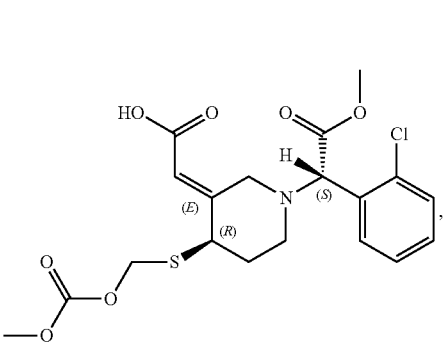
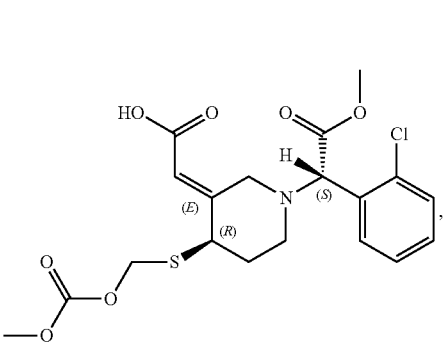
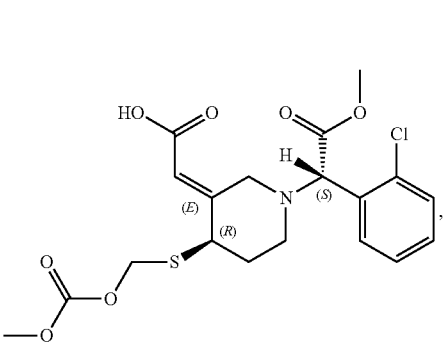

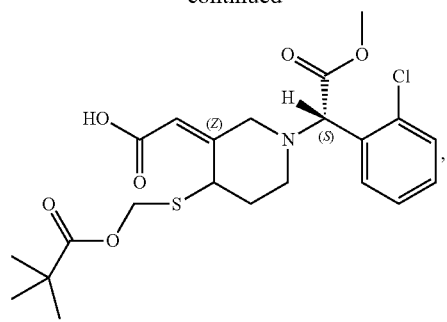
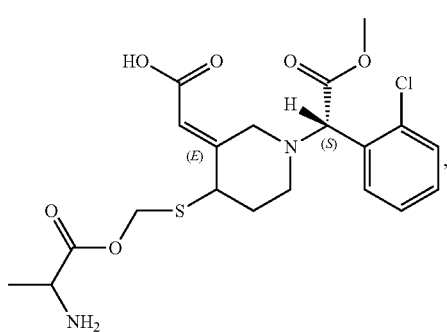
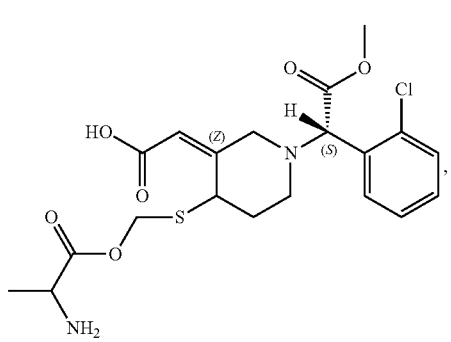
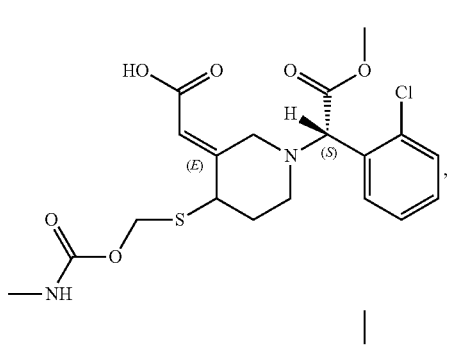
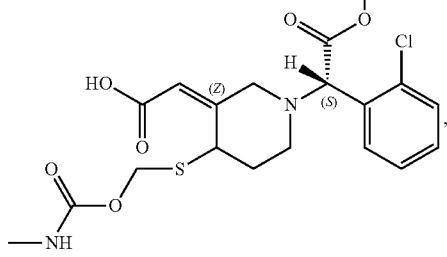
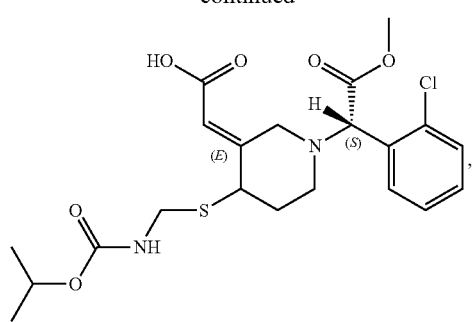
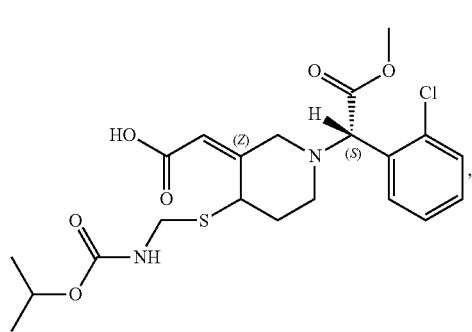
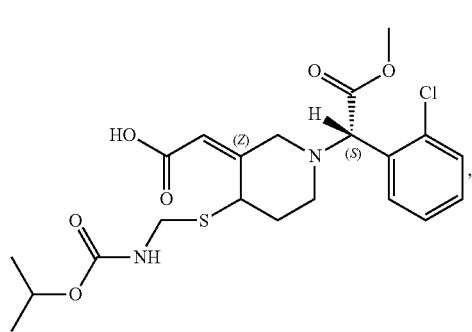
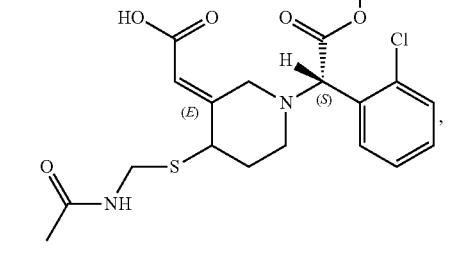
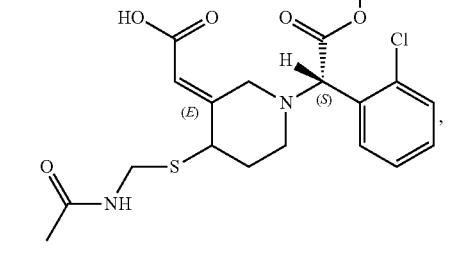

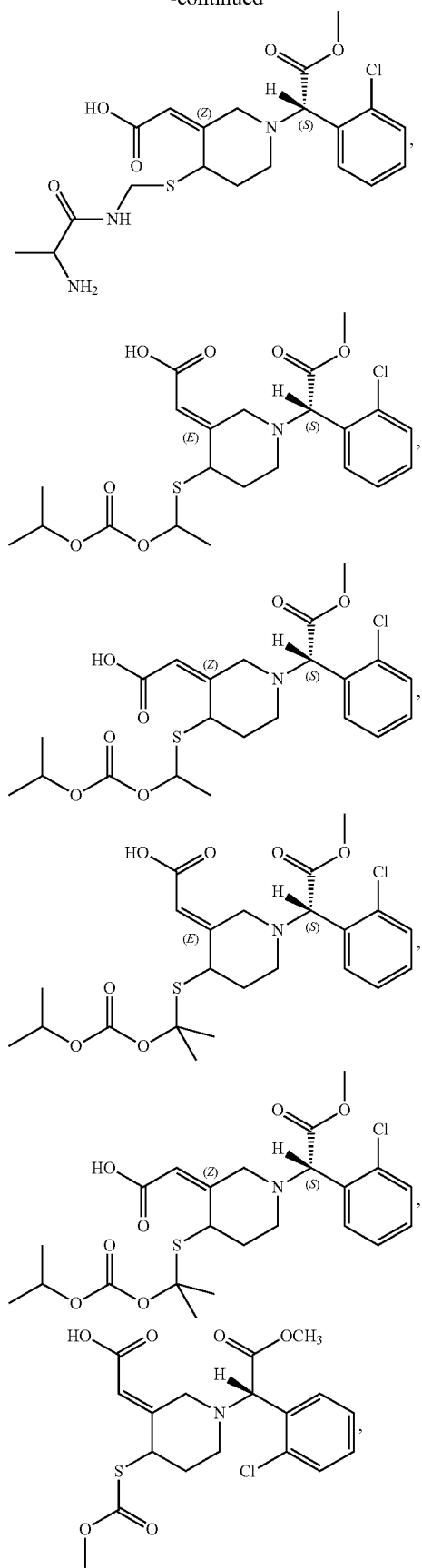
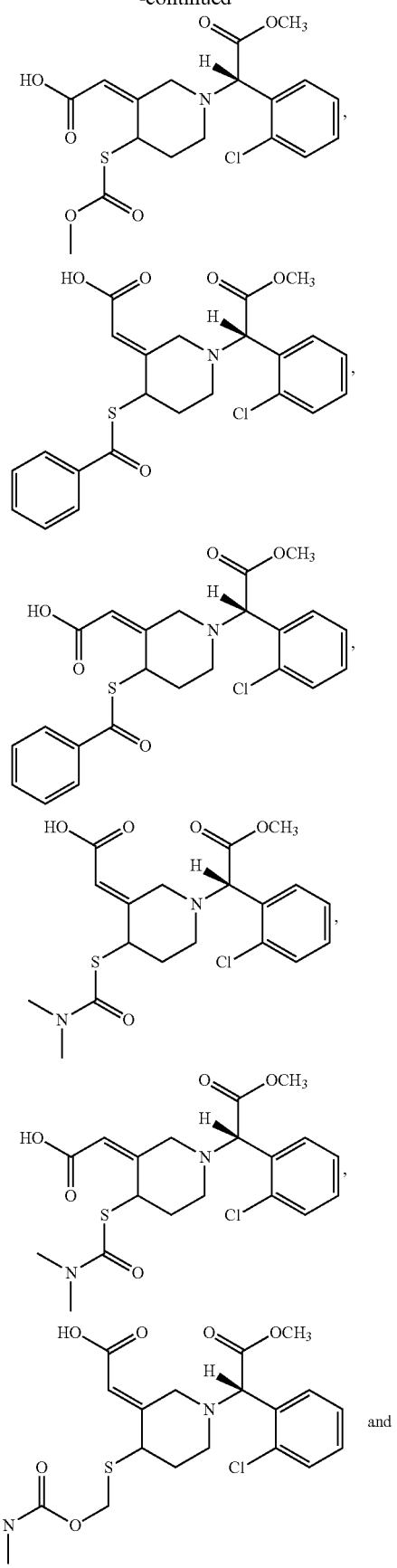

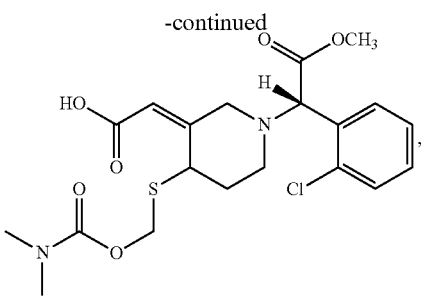

or a pharmaceutically acceptable salt thereof.

Compounds provided herein are described with reference to both generic formulae and specific compounds. In addition, compounds of the present disclosure may exist in a number of different forms or derivatives, all within the scope of the present disclosure. These include, for example, tautomers, stereoisomers, racemic mixtures, regioisomers, salts, solvated forms, amorphous forms, different crystal forms or polymorphs.

The compounds of present disclosure can comprise one or more asymmetric centers depending on substituent selection, and thus can exist in various stereoisomeric forms, e.g., enantiomers and/or diastereomers. For example, the compounds provided herein may have an asymmetric carbon center, and thus compounds provided herein may have either the (R) or (S) stereo-configuration at a carbon asymmetric center. Therefore, compounds of the present disclosure may be in the form of an individual enantiomer, diastereomer or geometric isomer, or may be in the form of a mixture of stereoisomers.

As used herein, the term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

Where a particular enantiomer is preferred, it may, in some embodiments be provided substantially free of the opposite enantiomer, and may also be referred to as "optically enriched". "Optically enriched", as used herein, means that the compound is made up of a significantly greater proportion of one enantiomer. In certain embodiments, the compound is made up of at least about 90% by weight of a preferred enantiomer. In other embodiments, the compound is made up of at least about 95%, 98%, or 99% by weight of a preferred enantiomer. Preferred enantiomers may be isolated from racemic mixtures by any method known to those skilled in the art, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound provided herein or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, IN 1972).

In some embodiments, mixtures of diastereomers, for example mixtures of diastereomers enriched with 51% or more of one of the diastereomers, including for example 60% or more, 70% or more, 80% or more, or 90% or more of one of the diastereomers are provided.

In some embodiments, compounds provided herein may have one or more double bonds that can exist as either the Z or E isomer, unless otherwise indicated. The present disclosure additionally encompasses the compounds as individual isomers substantially free of other isomers and alternatively, as mixtures of various isomers, e.g., racemic mixtures of enantiomers.

The compounds of the present disclosure may also exist in different tautomeric forms, and all such forms are embraced within the scope of the present disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol, amide-imidic acid, lactam-lactim, imine-enamine isomerizations and annular forms where a proton can occupy two or more positions of a heterocyclic system (for example, 1H- and 3H-imidazole, 1H-, 2H- and 4H-1,2,4-triazole, 1H- and 2H-isoindole, and 1H- and 2H-pyrazole). Valence tautomers include interconversions by reorganization of some of the bonding electrons. Tautomers can be in equilibrium or sterically locked into one form by appropriate substitution. Compounds of the present disclosure identified by name or structure as one particular tautomeric form are intended to include other tautomeric forms unless otherwise specified.

The present disclosure is also intended to include all isotopes of atoms in the compounds. Isotopes of an atom include atoms having the same atomic number but different mass numbers. For example, unless otherwise specified, hydrogen, carbon, nitrogen, oxygen, phosphorous, sulfur, fluorine, chlorine, bromide or iodine in the compounds of present disclosure are meant to also include their isotopes, such as but not limited to $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{18}F$, $^{19}F$, $^{35}Cl$, $^{37}Cl$, $^{79}Br$, $^{81}Br$, $^{124}I$, $^{127}I$ and $^{131}I$. In some embodiments, hydrogen includes protium, deuterium and tritium. In some embodiments, carbon includes $^{12}C$ and $^{13}C$. Isotopically-enriched compounds of Formula (I) can be prepared without undue experimentation by conventional techniques well known to those skilled in the art or by processes analogous to those described in the Schemes and Examples herein using appropriate isotopically-enriched reagents and/or intermediates.

Compounds of the present disclosure can be formulated as or be in the form of pharmaceutically acceptable salts. Unless specified to the contrary, a compound provided herein includes pharmaceutically acceptable salts of such compound.

As used herein, the term "pharmaceutically acceptable" indicates that the substance or composition is compatible chemically and/or toxicologically, with the other ingredients comprising a formulation, and/or the subjects being treated therewith.

As used herein, the term "pharmaceutically acceptable salt", unless otherwise indicated, includes salts that retain the biological effectiveness of the free acids and bases of the specified compound and that are not biologically or otherwise undesirable. Contemplated pharmaceutically acceptable salt forms include, but are not limited to, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, PA, Vol. 2, p. 1457, 1995; "Handbook of Pharmaceutical Salts: Properties, Selection, and Use" by Stahl and Wermuth, Wiley-VCH, Weinheim, Germany, 2002. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. Thus, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

It is also to be understood that the compounds of present disclosure can exist in unsolvated forms, solvated forms (e.g., hydrated forms), and solid forms (e.g., crystal or polymorphic forms), and the present disclosure is intended to encompass all such forms.

As used herein, the term "solvate" or "solvated form" refers to solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. Examples of solvents that form solvates include, but are not limited to, water, isopropanol, ethanol, methanol, DMSO, ethyl acetate, acetic acid, and ethanolamine.

As used herein, the terms "crystal form", "crystalline form", "polymorphic forms" and "polymorphs" can be used interchangeably, and mean crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The present disclosure is also intended to include all isotopes of atoms in the compounds. Isotopes of an atom include atoms having the same atomic number but different mass numbers. For example, unless otherwise specified, hydrogen, carbon, nitrogen, oxygen, phosphorous, sulfur, fluorine, chlorine, bromide or iodine in the compounds of present disclosure are meant to also include their isotopes, such as but not limited to $^1H$, $^2H$, $^3H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{18}F$, $^{19}F$, $^{35}Cl$, $^{37}Cl$, $^{79}Br$, $^{81}Br$, $^{124}I$, $^{127}I$ and $^{131}I$. In some embodiments, hydrogen includes protium, deuterium and tritium. In some embodiments, carbon includes $^{12}C$ and $^{13}C$.

Synthesis of Compounds

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by one skilled in the art.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), in P. Kocienski, Protecting Groups, Georg Thieme Verlag, 2003, and in Peter G. M. Wuts, Greene's Protective Groups in Organic Synthesis, 5th Edition, Wiley, 2014, all of which are incorporated herein by reference in its entirety.

Reactions can be monitored according to any suitable method known in the art. For example, product formation can be monitored by spectroscopic means, such as nuclear magnetic resonance spectroscopy (e.g. $^1H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by one skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The known starting materials of the present disclosure can be synthesized by using or according to the known methods in the art, or can be purchased from commercial suppliers. Unless otherwise noted, analytical grade solvents and commercially available reagents were used without further purification.

Unless otherwise specified, the reactions of the present disclosure were all done under a positive pressure of nitrogen or argon or with a drying tube in anhydrous solvents, and the reaction flasks were typically fitted with rubber septa for the introduction of substrates and reagents via syringe. Glassware was oven dried and/or heat dried.

For illustrative purposes, the Examples section below shows synthetic route for preparing the compounds of the present disclosure as well as key intermediates. Those skilled in the art will appreciate that other synthetic routes may be used to synthesize the inventive compounds. Although specific starting materials and reagents are depicted, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In an aspect, the present disclosure provides a compound having a formula of:

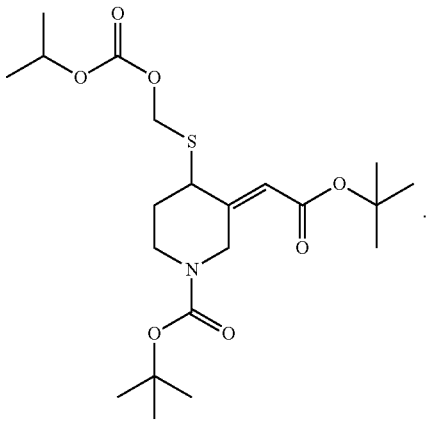 [SMILES: CC(C)OC(=O)OCSC1CCN(C(=O)OC(C)(C)C)C/C1=C\C(=O)OC(C)(C)C]

In some embodiments, the above compound can be used as an intermediate to prepare the compound of the present disclosure.

In another aspect, the present disclosure provides a compound having a formula of:

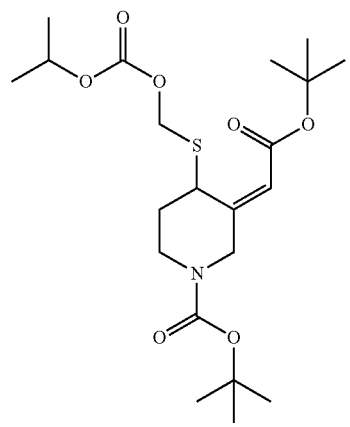

In some embodiments, the above compound can be used as an intermediate to prepare the compound of the present disclosure.

Use of Compounds

In an aspect, the present disclosure provides compounds of Formula (I) or pharmaceutically acceptable salts thereof, which are capable of inhibiting platelet aggregation. Thus, the compounds of the present disclosure or a pharmaceutically acceptable salt thereof are useful as medicinal drugs, and particularly useful as therapeutic or prophylactic agent for various thrombotic diseases.

As used herein, the term "therapy" is intended to have its normal meaning of dealing with a disease in order to entirely or partially relieve one, some or all of its symptoms, or to correct or compensate for the underlying pathology, thereby achieving beneficial or desired clinical results. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Therapy" can also mean prolonging survival as compared to expected survival if not receiving it. Those in need of therapy include those already with the condition or disorder as well as those prone to have the condition or disorder or those in which the condition or disorder is to be prevented. The term "therapy" also encompasses prophylaxis unless there are specific indications to the contrary. The terms "therapeutic" and "therapeutically" should be interpreted in a corresponding manner.

The term "treatment" is used synonymously with "therapy". Similarly the term "treat" can be regarded as "applying therapy" where "therapy" is as defined herein.

As used herein, the term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

In some embodiments, the compounds of the present disclosure can convert to active thiol-metabolite after administration. In some embodiments, the compounds of the present disclosure can convert to active thiol-metabolite after oral administration. In some embodiments, the compounds of the present disclosure can convert to active thiol-metabolite after intravenous injection.

For a prodrug of the active thiol-metabolite, it can be desirable that the prodrug remains stable (resistance to environment), while converts to the active thiol-metabolite in the target tissue with high conversion rate. Further, it can be desirable that the prodrug has a fast onset of action and thus a low loading dose and low side effect, a high solubility in aqueous solution which allows for formulating into injection for first aids and surgeries.

In some embodiments, the compounds provided herein can undergo a hydrolysis process via hydrolase to form the active thiol-metabolite. Due to the high in vivo activity and the wide spread of hydrolase in intestine, liver and plasma, the compounds provided herein can convert to the active thiol-metabolite in vivo at a higher conversion rate and less interpatient variability, thereby providing a fast onset of antiplatelet action without the need to use a high loading dose. In addition, since the metabolism of the compound provided herein is mediated by hydrolase rather than CYP enzymes, use of these compounds is not limited by potential interactions with other CYP-targeted drugs.

In some embodiments, the compounds provided herein show a faster onset of antiplatelet action than clopidogrel at the same dose. In some embodiments, the compounds provided herein show an onset of antiplatelet action less than that of clopidogrel at a dose lower than that of clopidogrel. In some embodiments, at a dose 2-fold lower than that of clopidogrel, the compounds provided herein show an onset of antiplatelet action less than that of clopidogrel. In some embodiments, at a dose 3-fold lower than that of clopidogrel, the compounds provided herein show an onset of antiplatelet action less than that of clopidogrel. In some embodiments, at a dose 4-fold lower than that of clopidogrel, the compounds provided herein shows an onset of antiplatelet action less than that of clopidogrel. In some embodiments, at a dose 5-fold lower than that of clopidogrel, the compounds provided herein shows an onset of antiplatelet action less than that of clopidogrel.

In some embodiments, at a dose 5-fold lower than that of clopidogrel, the compounds provided herein show an onset of antiplatelet action of less than 120 minutes, less than 110 minutes, less than 100 minutes, less than 90 minutes, less than 80 minutes, less than 70 minutes, less than 60 minutes, less than 50 minutes, less than 40 minutes, or even less than 30 minutes.

In some embodiments, the compounds provided herein show an improved aqueous solubility than clopidogrel as measured in phosphate buffer. In some embodiments, the compounds provided herein show an aqueous solubility, as measured in buffered aqueous solutions, of greater than 0.2 mg/ml, greater than 0.3 mg/ml, greater than 0.4 mg/ml, greater than 0.5 mg/ml, greater than 0.6 mg/ml, greater than 0.7 mg/ml, greater than 0.8 mg/ml, greater than 0.9 mg/ml, greater than 1 mg/ml, or even greater.

The improved solubility of the compounds provided herein provides a chance to expand the use of the compounds in inhibiting platelet aggregation. In some embodiments, the compounds provided herein can be formulated for injection administration for use in first aids and surgeries. In some embodiments, the compounds provided herein can be formulated for oral administration for long-term inhibition of platelet aggregation.

In a further aspect, the present disclosure provides use of the compound of the present disclosure or a pharmaceutically acceptable salt thereof for treatment of vascular diseases.

In a further aspect, the present disclosure provides use of the compound of the present disclosure or a pharmaceutically acceptable salt thereof or the pharmaceutical composition of the present disclosure, in the manufacture of a medicament for treating vascular diseases.

Pharmaceutical Compositions

For the purposes of administration, in some embodiments, the compounds provided herein are administered as a raw chemical or are formulated as pharmaceutical compositions.

Therefore, in a further aspect, there is provided pharmaceutical compositions comprising one or more compounds of the present disclosure, or a pharmaceutically acceptable salt thereof.

In some embodiments, the pharmaceutical compositions of the present disclosure comprise a compound selected from any one of Formula (I) to (VII) or a pharmaceutically acceptable salt thereof. In some embodiments, the pharmaceutical compositions of the present disclosure comprise a first compound selected from any one of Formula (I) to (VII) or a pharmaceutically acceptable salt thereof and one or more additional compounds of the same formula but said first compound and additional compounds are not the same molecules.

As used herein, the term "pharmaceutical composition" refers to a formulation containing the molecules or compounds of the present disclosure in a form suitable for administration to a subject.

In some embodiments, the pharmaceutical compositions of the present disclosure comprises a therapeutically effective amount of one or more compounds of Formula (I) to (VII) or a pharmaceutically acceptable salt thereof.

As used herein, the term "therapeutically effective amount" refers to an amount of a molecule, compound, or composition comprising the molecule or compound to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; the rate of administration; the therapeutic or combination of therapeutics selected for administration; and the discretion of the prescribing physician. Therapeutically effective amounts for a given situation can be determined by routine experimentation that is within the skill and judgment of the clinician.

In another aspect, there is provided pharmaceutical composition comprising one or more molecules or compounds of the present disclosure, or a pharmaceutically acceptable salt thereof, and at least one pharmaceutical acceptable excipient.

As used herein, the term "pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used herein includes both one and more than one such excipient. The term "pharmaceutically acceptable excipient" also encompasses "pharmaceutically acceptable carrier" and "pharmaceutically acceptable diluent".

The particular excipient used will depend upon the means and purpose for which the compounds of the present disclosure is being applied. Solvents are generally selected based on solvents recognized by persons skilled in the art as safe to be administered to a mammal including humans. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

In some embodiments, suitable excipients may include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, dextrins, or substituted dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some embodiments, suitable excipients may include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present disclosure or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as the compounds disclosed herein and, optionally, a chemotherapeutic agent) to a mammal including humans. The components of the liposome are commonly arranged in a bilayer formation, similar to the lipid arrangement of biological membranes.

The pharmaceutical compositions provided herein can be in any form that allows for the composition to be administered to a subject, including, but not limited to a human, and formulated to be compatible with an intended route of administration.

A variety of routes are contemplated for the pharmaceutical compositions provided herein, and accordingly the pharmaceutical composition provided herein may be supplied in bulk or in unit dosage form depending on the intended administration route. For example, for oral, buccal, and sublingual administration, powders, suspensions, granules, tablets, pills, capsules, gelcaps, and caplets may be acceptable as solid dosage forms, and emulsions, syrups, elixirs, suspensions, and solutions may be acceptable as liquid dosage forms. For injection administration, emulsions and suspensions may be acceptable as liquid dosage forms, and a powder suitable for reconstitution with an appropriate solution as solid dosage forms. For inhalation administration, solutions, sprays, dry powders, and aerosols may be acceptable dosage form. For topical (including buccal and sublingual) or transdermal administration, powders, sprays, ointments, pastes, creams, lotions, gels, solutions, and patches may be acceptable dosage form. For vaginal administration, pessaries, tampons, creams, gels, pastes, foams and spray may be acceptable dosage form.

The quantity of active ingredient in a unit dosage form of composition is a therapeutically effective amount and is varied according to the particular treatment involved. As used herein, the term "therapeutically effective amount" refers to an amount of a molecule, compound, or composition comprising the molecule or compound to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; the rate of administration; the therapeutic or combination of therapeutics selected for administration; and the discretion of the prescribing physician. Therapeutically effective amounts for a given situation can be determined by routine experimentation that is within the skill and judgment of the clinician.

In some embodiments, the pharmaceutical compositions of the present disclosure may be in a form of formulation for oral administration.

In certain embodiments, the pharmaceutical compositions of the present disclosure may be in the form of tablet formulations. Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case using conventional coating agents and procedures well known in the art.

In certain embodiments, the pharmaceutical compositions of the present disclosure may be in a form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

In certain embodiments, the pharmaceutical compositions of the present disclosure may be in the form of aqueous suspensions, which generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

In certain embodiments, the pharmaceutical compositions of the present disclosure may be in the form of oily suspensions, which generally contain suspended active ingredient in a vegetable oil (such as *arachis* oil, castor oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

In certain embodiments, the pharmaceutical compositions of the present disclosure may be in the form of oil-in-water emulsions. The oily phase may be a vegetable oil, such as olive oil or *arachis* oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

In certain embodiments, the pharmaceutical compositions provided herein may be in the form of syrups and elixirs, which may contain sweetening agents such as glycerol, propylene glycol, sorbitol, aspartame or sucrose, a demulcent, a preservative, a flavoring and/or coloring agent.

In some embodiments, the pharmaceutical compositions of the present disclosure may be in a form of formulation for injection administration.

In certain embodiments, the pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments, the pharmaceutical compositions of the present disclosure may be in a form of formulation for inhalation administration.

In certain embodiments, the pharmaceutical compositions of the present disclosure may be in the form of aqueous and nonaqueous (e.g., in a fluorocarbon propellant) aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols.

In some embodiments, the pharmaceutical compositions of the present disclosure may be in a form of formulation for topical or transdermal administration.

In certain embodiments, the pharmaceutical compositions provided herein may be in the form of creams, ointments, gels and aqueous or oily solutions or suspensions, which may generally be obtained by formulating an active ingredient with a conventional, topically acceptable excipients such as animal and vegetable fats, oils, waxes, paraffins, starch, tragacanth, cellulose derivatives, polyethylene glycols, silicones, bentonites, silicic acid, talc and zinc oxide, or mixtures thereof.

In certain embodiments, the pharmaceutical compositions provided herein may be formulated in the form of transdermal skin patches that are well known to those of ordinary skill in the art.

Besides those representative dosage forms described above, pharmaceutically acceptable excipients and carriers are generally known to those skilled in the art and are thus included in the present disclosure. Such excipients and carriers are described, for example, in "Remingtons Pharmaceutical Sciences" Mack Pub. Co., New Jersey (1991), in "Remington: The Science and Practice of Pharmacy", Ed. University of the Sciences in Philadelphia, 21$^{st}$ Edition, LWW (2005), which are incorporated herein by reference.

In some embodiments, the pharmaceutical compositions of the present disclosure can be formulated as a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. The amount of the compounds provided herein in the unit dosage form will vary depending on the condition to be treated, the subject to be treated (e.g., the age, weight, and response of the individual subject), the particular route of administration, the actual compound administered and its relative activity, and the severity of the subject's symptoms.

In some embodiments, dosage levels of the pharmaceutical compositions of the present disclosure can be between 0.001-1000 mg/kg body weight/day, for example, 0.001-1000 mg/kg body weight/day, 0.001-900 mg/kg body weight/day, 0.001-800 mg/kg body weight/day, 0.001-700 mg/kg body weight/day, 0.001-600 mg/kg body weight/day, 0.001-500 mg/kg body weight/day, 0.001-400 mg/kg body weight/day, 0.001-300 mg/kg body weight/day, 0.001-200 mg/kg body weight/day, 0.001-100 mg/kg body weight/day, 0.001-50 mg/kg body weight/day, 0.001-40 mg/kg body weight/day, 0.001-30 mg/kg body weight/day, 0.001-20 mg/kg body weight/day, 0.001-10 mg/kg body weight/day, 0.001-5 mg/kg body weight/day, 0.001-1 mg/kg body weight/day, 0.001-0.5 mg/kg body weight/day, 0.001-0.4 mg/kg body weight/day, 0.001-0.3 mg/kg body weight/day, 0.001-0.2 mg/kg body weight/day, 0.001-0.1 mg/kg body weight/day, 0.005-0.1 mg/kg body weight/day, 0.01-0.1 mg/kg body weight/day, 0.02-0.1 mg/kg body weight/day, 0.03-0.1 mg/kg body weight/day, 0.04-0.1 mg/kg body weight/day, 0.05-0.1 mg/kg body weight/day, 0.06-0.1 mg/kg body weight/day, 0.07-0.1 mg/kg body weight/day, 0.08-0.1 mg/kg body weight/day, or 0.09-0.1 mg/kg body weight/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of Comprehensive Medicinal Chemistry (Corwin Hansch; Chairman of Editorial Board), Pergamon Press 1990, which is specifically incorporated herein by reference.

In some embodiments, the pharmaceutical compositions of the present disclosure are formulated for oral administration. In some embodiments, the unit dosage for oral administration contains one or more compounds provided herein in an amount from about 1 mg to about 1000 mg, for example from about 5 mg to about 1000 mg, from about 10 mg to about 1000 mg, from about 15 mg to about 1000 mg, from about 20 mg to about 1000 mg, from about 25 mg to about 1000 mg, from about 30 mg to about 1000 mg, from about 40 mg to about 1000 mg, from about 50 mg to about 1000 mg, from about 60 mg to about 1000 mg, from about 70 mg to about 1000 mg, from about 80 mg to about 1000 mg, from about 90 mg to about 1000 mg, from about 100 mg to about 1000 mg, from about 200 mg to 1000 mg, from about 300 mg to about 1000 mg, from about 400 mg to about 1000 mg, from about 500 mg to about 1000 mg, from about 1 mg to 500 mg, from about 10 mg to about 500 mg, from about 50 mg to about 500 mg, from about 100 mg to about 500 mg, from about 200 mg to about 500 mg, from about 300 mg to about 500 mg, from about 400 mg to about 500 mg, for example about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 75 mg, about 100 mg, about 150 mg, about 200 mg, about 225 mg, about 250 mg, about 275 mg, about 300 mg and the like. In some embodiments, the dosage unit may be administered to a subject from 1 to 6 times per day depending on the severity of the subject's symptoms.

In some embodiments, the pharmaceutical compositions of the present disclosure are formulated for oral administration in a treatment having a duration of more than 1 week, more than 2 weeks, more than 3 weeks, more than 1 month, more than 2 months, more than 3 months, more than 4 months, more than 5 months, more than 6 months, more than 7 months, more than 8 months, more than 9 months, more than 10 months, more than 11 months, more than 1 year or even longer.

In some embodiments, the pharmaceutical compositions of the present disclosure are formulated for parenteral administration, e.g., administered intravenously, subcutaneously or intramuscularly via injection. In some embodiments, the unit dosage for parenteral administration contains one or more compounds provided herein in an amount from about 0.1 mg to about 500 mg of one or more compounds provided herein, for example from about 0.2 mg to about 500 mg, from about 0.3 mg to about 500 mg, from about 0.4 mg to about 500 mg, from about 0.5 mg to about 500 mg, from about 1 mg to about 500 mg, from about 5 mg to about 500 mg, from about 10 mg to about 500 mg, from about 20 mg to about 500 mg, from about 30 mg to about 500 mg, from about 40 mg to about 500 mg, from about 50 mg to about 500 mg, from about 0.5 mg to about 400 mg, from about 0.5 mg to about 300 mg, from about 0.5 mg to about 200 mg, from about 0.5 mg to about 100 mg, from about 0.5 mg to about 90 mg, from about 0.5 mg to about 80 mg, from about 0.5 mg to about 70 mg, from about 0.5 mg to about 60 mg, from about 0.5 mg to about 50 mg, from about 0.5 mg to about 40 mg, from about 1 mg to about 90 mg, from about 5 mg to about 90 mg, from about 10 mg to about 80 mg, from about 20 mg to about 70 mg, from about 30 mg to about 60 mg, or from about 40 mg to about 50 mg, for example about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg and the like.

In some embodiments, the pharmaceutical composition intended to be administered by injection can be prepared by combining one or more compounds of the present disclosure with sterile, distilled water, sesame or peanut oil, aqueous propylene glycol, so as to form a solution. In some embodiments, the pharmaceutical composition may comprise a surfactant or other solubilizing excipient that is added to facilitate the formation of a homogeneous solution or suspension. In some embodiments, the pharmaceutical composition may further comprise one or more additional agents selected from the group consisting of a wetting agent, a suspending agent, a preservative, a buffer, and an isotonizing agent.

In some embodiments, the pharmaceutical composition intended to be administered by injection can be administered with a syringe. In some embodiments, the syringe is disposable. In some embodiments, the syringe is reusable. In some embodiments, the syringe is pre-filled with the pharmaceutical composition provided herein.

In a further aspect, there is also provided veterinary compositions comprising one or more molecules or compounds of the present disclosure or pharmaceutically acceptable salts thereof and a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The pharmaceutical compositions or veterinary compositions may be packaged in a variety of ways depending upon the method used for administering the drug. For example, an article for distribution can include a container having deposited therein the compositions in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The compositions may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

In a further aspect, there is also provided pharmaceutical compositions comprise one or more compounds of the present disclosure, or a pharmaceutically acceptable salt thereof, as a first active ingredient, and a second active ingredient.

In some embodiments, the second active ingredient has complementary activities to the compound provided herein such that they do not adversely affect each other. Such ingredients are suitably present in combination in amounts that are effective for the purpose intended.

Method of Treatment of Disease

In a further aspect, the present disclosure provides a method for treating vascular disease, comprising administering an effective amount of the compound or a pharmaceutically acceptable salt thereof or the pharmaceutical composition provided herein to a subject in need thereof.

In some embodiments, the vascular disease is selected from atherothrombosis, ischemia, stroke, cerebral thrombosis, arterial thrombosis, thrombotic cerebrovascular, cardiovascular diseases and blood clots.

In a further aspect, the present disclosure provides a method for inhibiting platelet aggregation in a subject in need thereof, comprising administering an effective amount of the compound or a pharmaceutically acceptable salt thereof or the pharmaceutical composition provided herein to the subject.

EXAMPLES

For the purpose of illustration, the following examples are included. However, it is to be understood that these examples do not limit the present disclosure and are only meant to suggest a method of practicing the present disclosure. Persons skilled in the art will recognize that the chemical reactions described may be readily adapted to prepare a number of other compounds of the present disclosure, and alternative methods for preparing the compounds of the present disclosure are deemed to be within the scope of the present disclosure. For example, the synthesis of non-exemplified compounds according to the present disclosure may be successfully performed by modifications apparent to those skilled in the art, e.g., by appropriately protecting interfering groups, by utilizing other suitable reagents and building blocks known in the art other than those described, and/or by making routine modifications of reaction conditions. Alternatively, other reactions disclosed herein or known in the art will be recognized as having applicability for preparing other compounds of the present disclosure.

Example 1

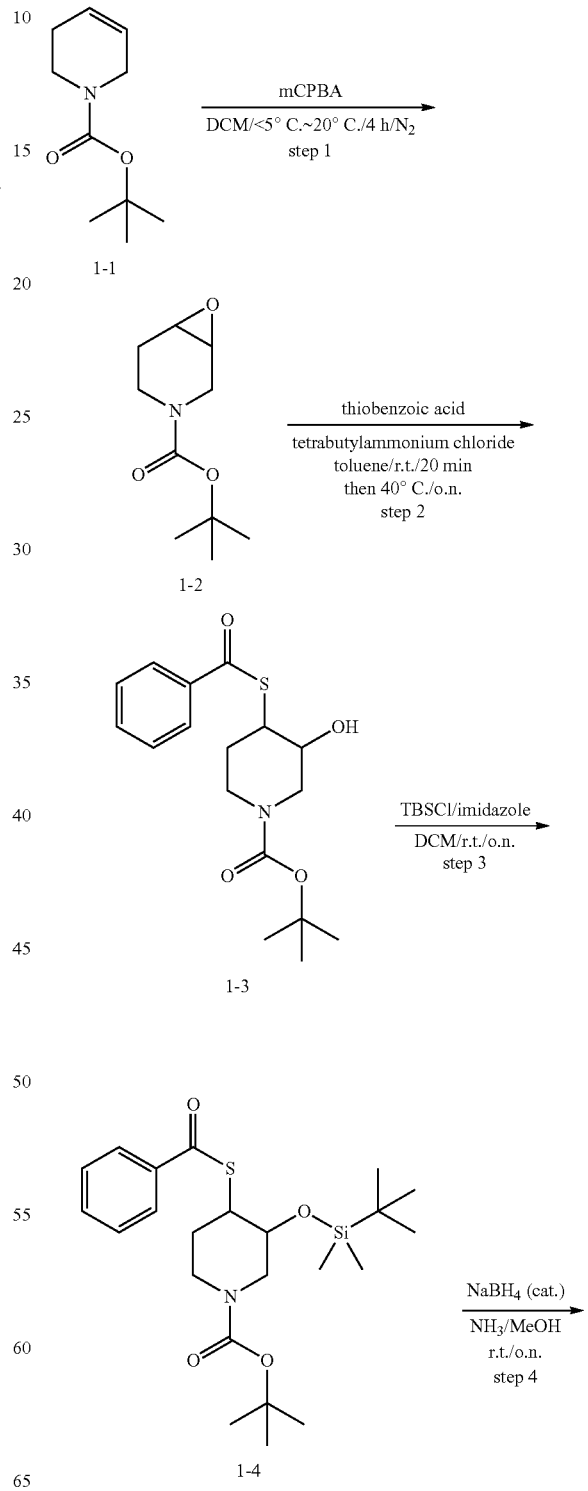

-continued
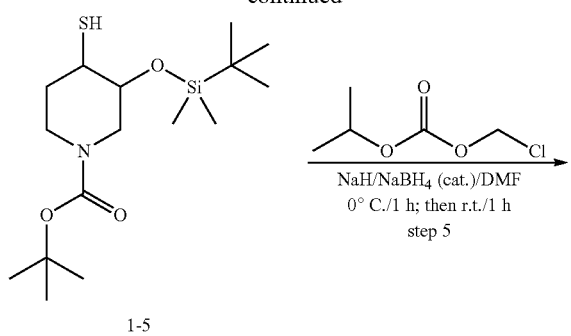
1-5
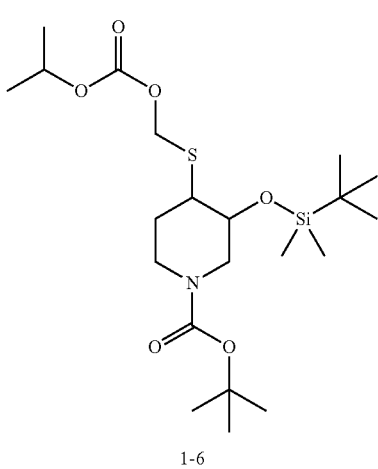
1-6
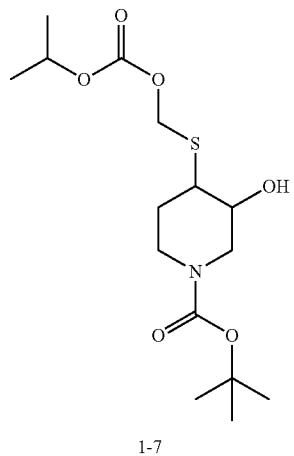
1-7
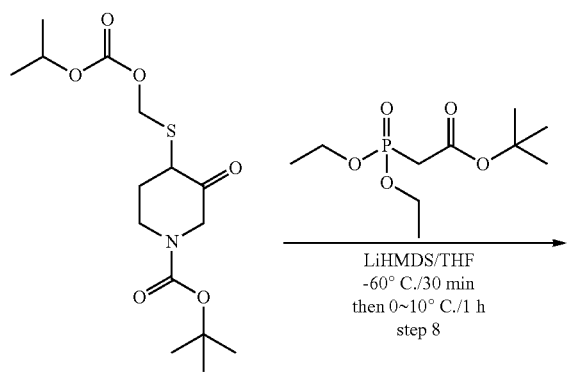
1-8
-continued
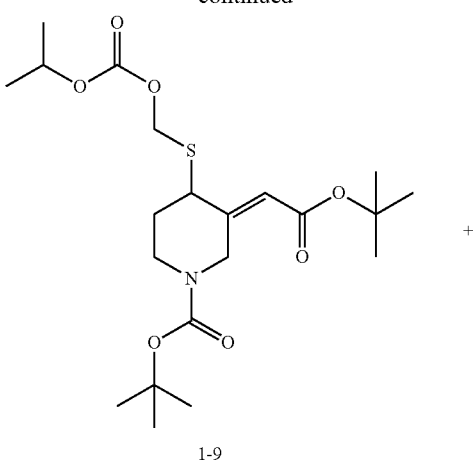
1-9
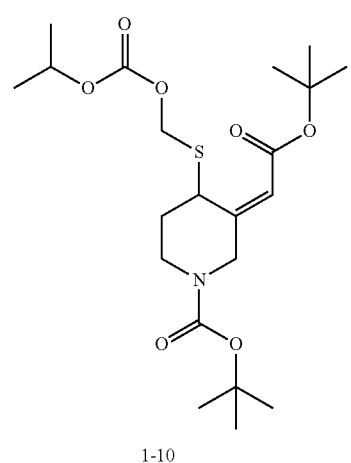
1-10
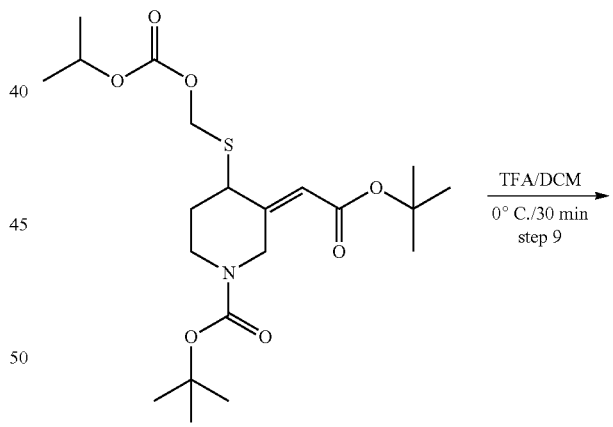
1-9
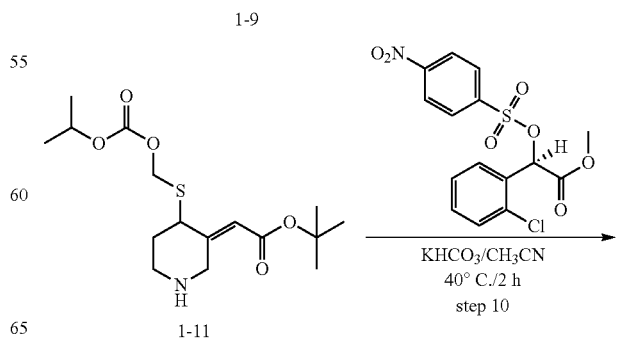
1-11

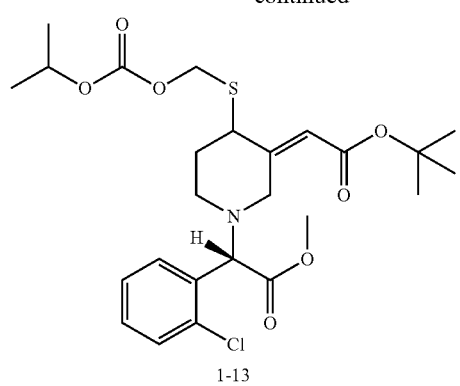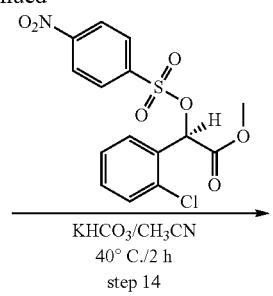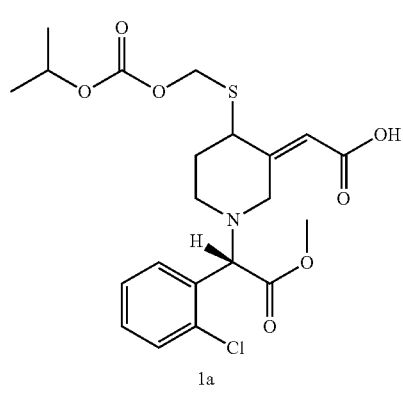

Step 1. Synthesis of 1-2

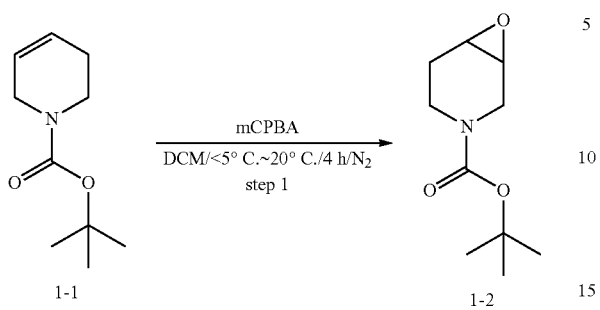

A solution of 1-1 (56.7 g, 310 mmol) in DCM (500 mL) was stirred in an ice-bath (T<5° C.) under $N_2$ protection. mCPBA (107.0 g, 620 mmol) was added in portions to the above solution. After addition, the resulting mixture was stirred at 20° C. for 4 h. The mixture was poured into a solution of $Na_2S_2O_3$ (90.0 g) and $NaHCO_3$ (45.0 g) in water (300 mL) with stirring. The resulting mixture was extracted with DCM (300 mL*2). The combined organic layer was dried over $Na_2SO_4$, and filtered. The filtrate was concentrated and the residue was purified by silica gel chromatography (Petroleum Ether/EtOAc=100/1 to 5/1) to give 1-2 (67.0 g, 98% yield) as yellow oil.

Step 2. Synthesis of 1-3

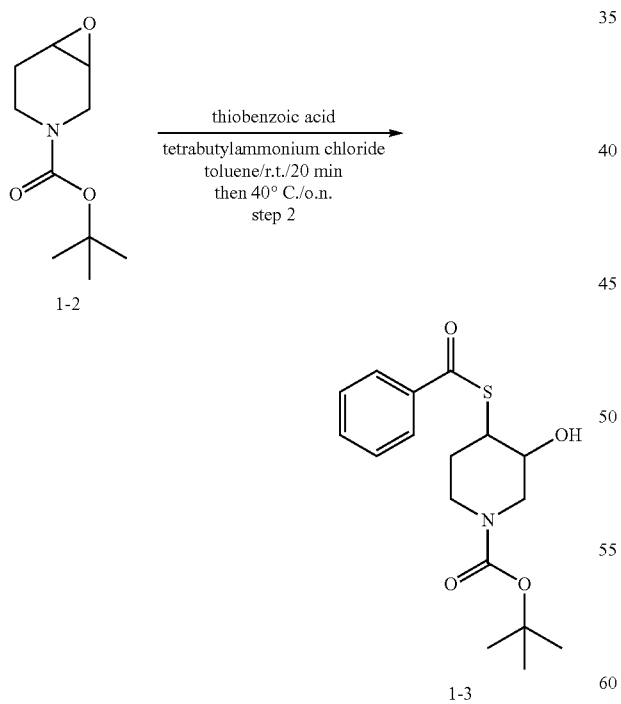

A mixture of 1-2 (67.0 g, 337 mmol), thiobenzoic acid (56.7 g, 370 mmol) and tetrabutylammonium chloride (4.67 g, 17 mmol) in toluene (300 mL) was stirred at r.t. for 20 min and then at 40° C. overnight. Then the reaction mixture was concentrated under vacuum. To the residue was added sat. $Na_2CO_3$ (400 mL) with stirring, which was then extracted with EtOAc (400 mL*2). The organic layer was dried over $Na_2SO_4$, and filtered. The filtrate was concentrated and the residue was purified by silica gel chromatography (Petroleum Ether/EtOAc=10/1 to 5/1) to give 1-3 (87.5 g, 77% yield) as a white solid.

LC-MS $[M+1-100]^+=238.1$ $^1$H NMR (400 MHZ, Chloroform-d) δ 7.97 (d, J=7.2 Hz, 2H), 7.59 (s, 1H), 7.46 (t, J=7.7 Hz, 2H), 4.24 (d, J=16.3 Hz, 1H), 4.17-3.81 (m, 1H), 3.73 (s, 1H), 3.60 (s, 1H), 2.92 (t, J=24.3 Hz, 2H), 2.72 (s, 1H), 2.12 (d, J=16.8 Hz, 1H), 1.71 (d, J=11.6 Hz, 1H), 1.46 (s, 9H).

Step 3. Synthesis of 1-4

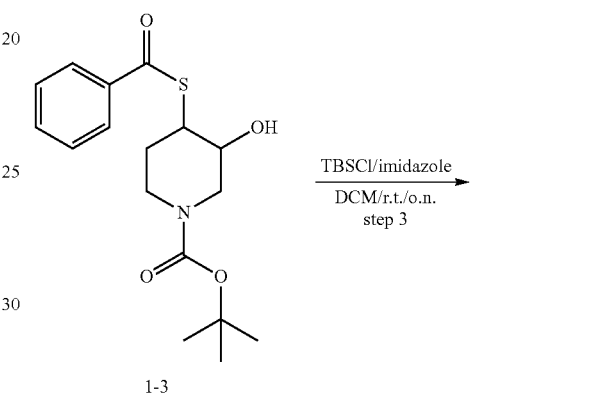

To a solution of 1-3 (157.0 g, 467.3 mmol) in DCM (1.5 L) were added TBSCl (141.2 g, 935 mmol), and imidazole (159.0 g, 2.34 mol). The resulting mixture was stirred at r.t. for overnight and then concentrated under reduce pressure. The residue was purified by silica gel chromatography (Petroleum ether/EtOAc=10/1) to give 1-4 (273.0 g, 94% yield) as a white solid. LC-MS $[M+1-100]^+=352.1$.

Step 4. Synthesis of 1-5

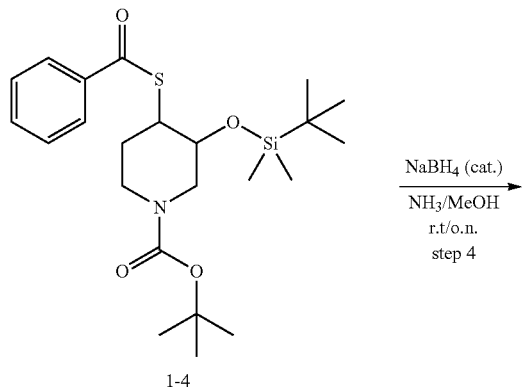

1-4

To a solution of 1-4 (263.0 g, 583.1 mmol) in NH₃/MeOH (7M, 2.0 L) was added NaBH₄ (222 mg, 5.8 mmol). The resulting mixture was stirred at r.t. for overnight and then concentrated under reduce pressure. The residue was purified by silica gel chromatography (Petroleum ether/EtOAc=20/1) to give 1-5 (210.0 g, 100% yield) as light yellow oil.

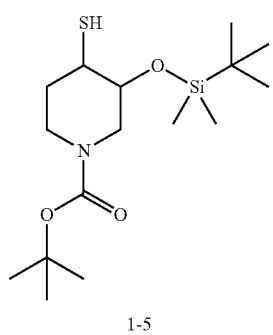

1-5

Step 5. Synthesis of 1-6

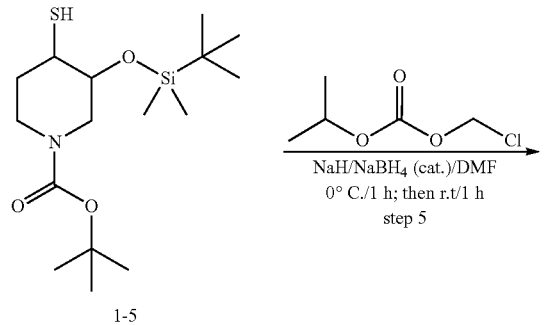

1-5

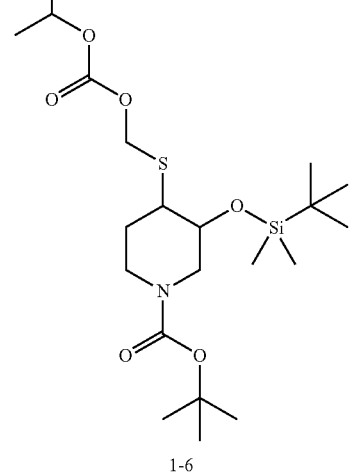

1-6

To a solution of NaBH₄ (1.1 g, 28.8 mmol) in DMF (1.0 L) was added NaH (20.7 g, 864.6 mmol) at 0° C. under N₂ with stirring. 1-5 (200.0 g, 576.4 mmol) was added dropwise at 0° C., which was then stirred at 0° C. for 1 h. Then, chloromethyl isopropyl carbonate (100.7 g, 662.8 mmol) was added at 0° C. and the resulting mixture was stirred at r.t. for 1 h. H₂O (1.0 L) was added to the mixture, which was then extracted with EtOAc (1.0 L*3). The organic layer was washed with brine, dried over Na₂SO₄, and filtered. The filtrate was concentrated under vacuum and the residue was purified by silica gel chromatography (Petroleum/EtOAc=20/1) to give 1-6 (135.0 g, 50% yield) as colorless oil.

$^1$H NMR (400 MHZ, Chloroform-d) δ 5.25 (q, J=12.0 Hz, 2H), 4.92-4.79 (m, 1H), 3.85 (d, J=58.8 Hz, 2H), 3.45 (s, 1H), 2.97-2.74 (m, 3H), 2.13-2.02 (m, 1H), 1.59-1.47 (m, 1H), 1.41 (s, 9H), 1.25 (dd, J=15.5, 4.6 Hz, 6H), 0.89 (s, 9H), 0.19-0.01 (m, 6H).

Step 6. Synthesis of 1-7

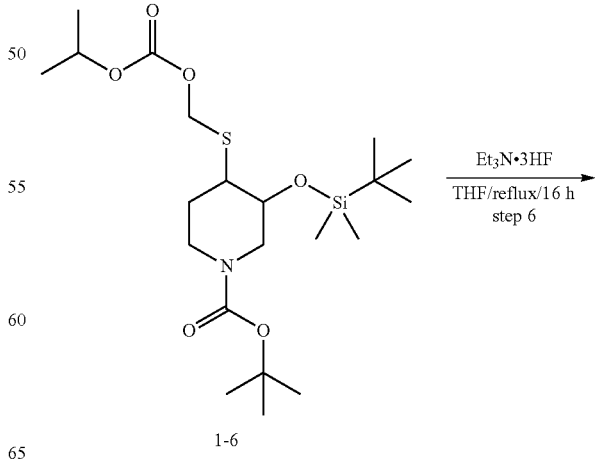

1-6

-continued

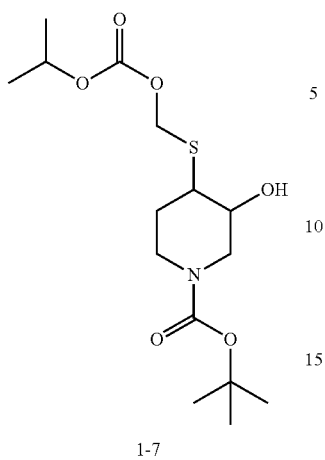

1-7

To a solution of 1-6 (129.0 g, 278.6 mmol) in THF (1.1 L) was added Et$_3$N·3HF (135.0 g, 835.9 mmol), which was stirred under reflux for 16 h. After completion, the reaction mixture was concentrated under reduce pressure, and the residue was purified by silica gel chromatography (Petroleum ether/EtOAc=3/1) to give 1-7 (80.0 g, 82% yield) as light yellow oil.

Step 7. Synthesis of 1-8

-continued 1-8

To a solution of 1-7 (30.0 g, 86.9 mmol) in DCM (300 mL) was added Dess-Martin Periodinane (72.9 g, 171.9 mmol), and the resulting mixture was stirred at 25° C. for 4 h. After completion, the above reaction mixture was added to a mixed solution of sat. Na$_2$S$_2$O$_3$/sat. NaHCO$_3$ (600 mL/600 mL), which was then extracted with EtOAc (400 mL*2). The combined organic layers was washed with sat. NaHCO$_3$, dried over Na$_2$SO$_4$, and filtered. The filtrate was concentrated under reduce pressure and the residue was purified by silica gel chromatography (Petroleum ether/EtOAc=20/1 to 8/1) to give 1-8 (22.0 g, 73% yield) as colorless oil.

Step 8. Synthesis of 1-9 and 1-10

1-7 
Dess-Martin Periodinane
DCM/25° C./4 h
step 7
→
1-8
LiHMDS/THF
−60° C./30 min
then 0~10° C./1 h
step 8
→

58

Step 9. Synthesis of 1-11

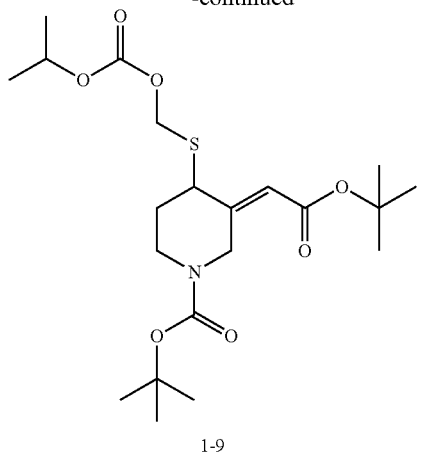

1-9

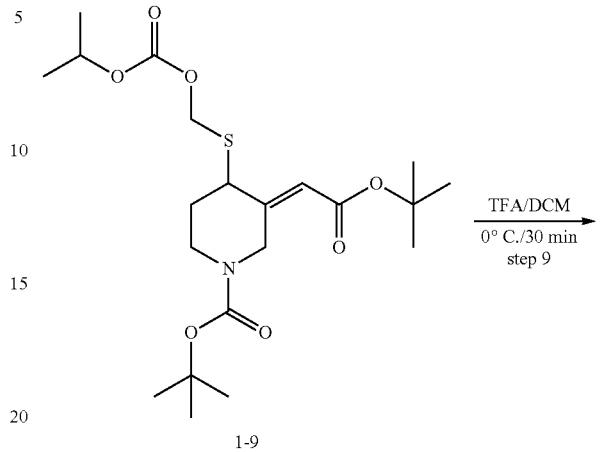

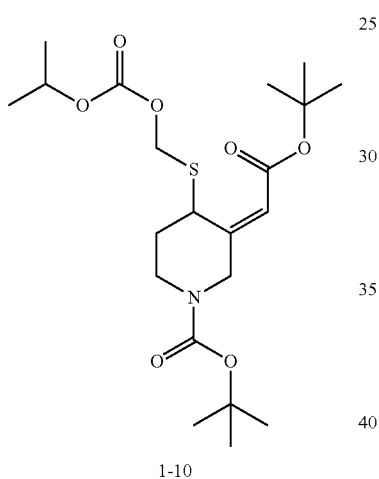

1-10

To a solution of tert-butyl 2-(diethoxyphosphoryl)acetate (11.4 g, 43.2 mmol) in THF (100 mL) was added LiHMDS (37.4 mL, 37.4 mmol) at −60° C. under $N_2$, which was stirred at −60° C. for 30 min. 1-8 (10.0 g, 28.8 mmol) was then added dropwise at −60° C., and the resulting mixture was stirred at 0~10° C. for 1 h. Then the reaction mixture was added to sat. $NH_4Cl$ (300 mL), which was then extracted with EtOAc (150 mL*2). The combined organic layer was washed with brine, dried over $Na_2SO_4$ and filtered. The filtrate was concentrated under vacuum and the residue was purified silica gel chromatography (Petroleum ether/ EtOAc=60/1) to give 1-9 (2.5 g, 19% yield) as light yellow oil and 1-10 (1.3 g, 10% yield) as light yellow oil.

1-9: $^1$H NMR (400 MHz, chloroform-d) δ 5.68 (s, 1H), 5.47 (d, J=15.2 Hz, 1H), 5.24 (s, 1H), 4.89-4.94 (m, 2H), 3.95 (s, 1H), 3.87-3.92 (m, 1H), 3.79 (s, 1H), 3.17-3.19 (m, 1H), 2.15-2.16 (m, 1H), 1.87-1.90 (m, 1H), 1.48 (s, 9H), 1.43 (s, 9H), 1.29 (d, J=4 Hz, 6H).

1-10: $^1$HNMR (400 MHZ, chloroform-d) δ 5.74 (s, 1H), 5.48 (s, 1H), 5.27 (d, J=12 Hz, 1H), 5.14 (d, J=12 Hz, 1H), 4.85-4.89 (m, 1H), 4.25-4.26 (m, 1H), 3.93-3.94 (m, 2H), 3.15 (s, 1H), 2.01-2.04 (m, 1H), 1.85-1.88 (m, 1H), 1.46 (s, 9H), 1.44 (s, 9H), 1.28 (d, J=4 Hz, 6H).

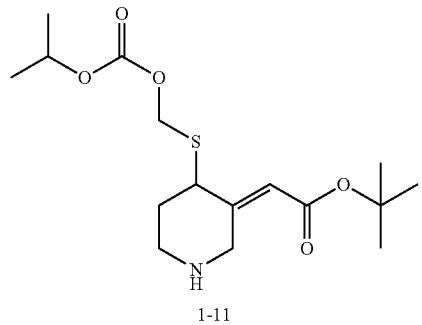

1-11

To a solution of 1-9 (3.0 g, 6.7 mmol) in DCM (20 mL) was added TFA (10 mL) at 0° C., then the reaction was stirred at 0° C. for 30 min. After completion, the reaction mixture was added to a solution of sat. $NaHCO_3$ (100 mL), which was then extracted with DCM (100 mL). The organic layer was dried over $Na_2SO_4$, and filtered. The filtrate was concentrated by reduce pressure to give crude 1-11 (3.0 g, >100% yield) as yellow oil, which was used in the in the next step without further purification. LC-MS $[M+1]^+$= 346.1

Step 10. Synthesis of 1-13

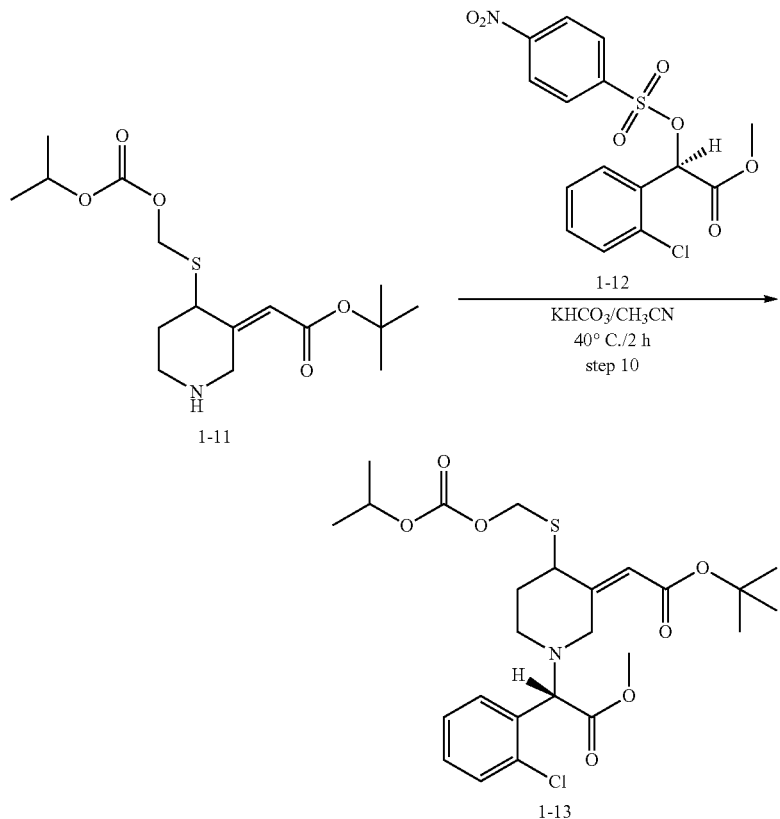

To a solution of 1-11 (3.0 g, crude) in CH₃CN (15 mL) were added 1-12 (2.6 g, 6.7 mmol), and KHCO₃ (1.35 g, 13.5 mmol). The resulting mixture was stirred at 40° C. for 2 h. After completion, the reaction mixture was concentrated under reduce pressure and the residue was purified by reversed-phase column chromatography (C18, CH₃CN/H₂O=80/20) to give 1-13 (1.8 g, 51% yield) as a white solid. LC-MS [M+1]⁺=528.2.

Steps 11 and 12. Synthesis of 1a-1 and 1a-2

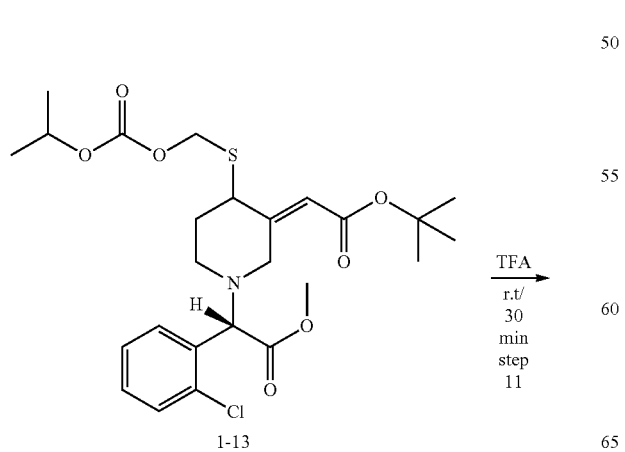

-continued

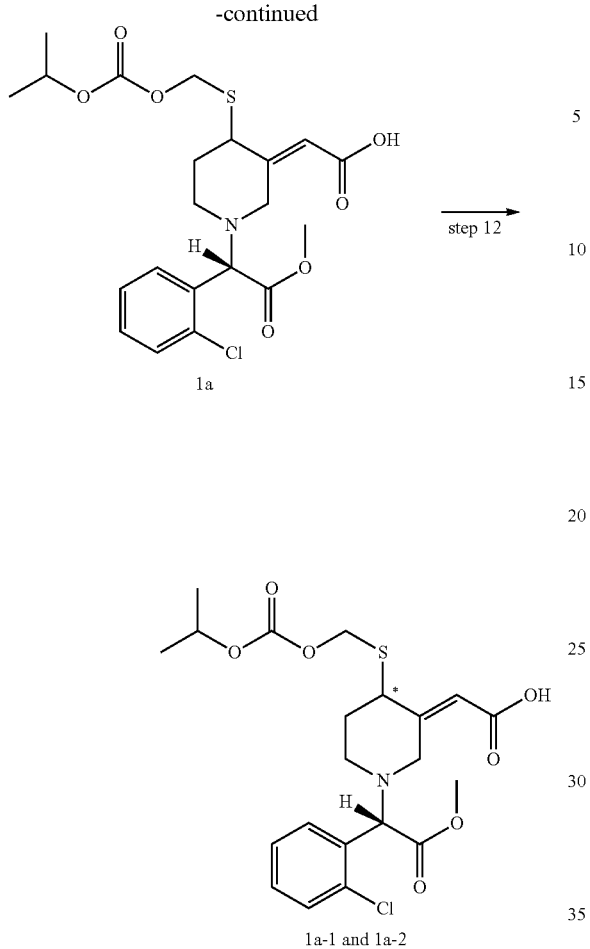

1a 1a-1 and 1a-2

A solution of 1-13 (1.8 g, 3.4 mmol) in TFA (10 mL) was stirred at r.t. for 30 min. After completion, the reaction mixture was added to a solution of sat. NaHCO$_3$ (100 mL), which was then extracted with EtOAc (100 mL*3). The combined organic layer was washed with sat. NaHCO$_3$, dried over Na$_2$SO$_4$ and filtered. The filtrate was concentrated under reduce pressure and the residue was purified by reversed-phase column chromatography (C18, CH$_3$CN/H$_2$O=80/20) to give 1a (550 mg, 34% yield). 1a was purified by chiral column chromatography to give 1a-1 and 1a-2.

1a:
LC-MS [M+1]$^+$=472.1
$^1$H NMR (400 MHZ, Chloroform-d) δ 7.59 (s, 1H), 7.38 (d, J=4 Hz, 1H), 7.32-7.26 (m, 2H), 5.86 (s, 1H), 5.22 (dd, J=12.2, 2.6 Hz, 1H), 5.00-4.83 (m, 3H), 4.50 (dd, J=66.2, 11.9 Hz, 1H), 3.82 (s, 1H), 3.70 (d, J=4.9 Hz, 3H), 3.52 (dd, J=37.9, 12.9 Hz, 1H), 2.92-2.64 (m, 2H), 2.45-2.30 (m, 1H), 1.95-1.84 (m, 1H), 1.30 (d, J=6.2 Hz, 6H).

1a-1:
$^1$H NMR (400 MHZ, CDCl$_3$) δ 7.65 (s, 1H), 7.46-7.43 (m, 1H), 7.33 (dd, J=6.3, 2.7 Hz, 2H), 5.91 (s, 1H), 5.27 (d, J=12.3 Hz, 1H), 5.04-4.87 (m, 3H), 4.49 (d, J=13.7 Hz, 1H), 3.88 (s, 1H), 3.75 (s, 3H), 3.58 (d, J=14.0 Hz, 1H), 2.87 (s, 2H), 2.44 (s, 1H), 1.95 (dd, J=14.2, 3.3 Hz, 1H), 1.35 (d, J=6.2 Hz, 6H).

1a-2:
$^1$H NMR (400 MHZ, CDCl$_3$) δ 7.63 (s, 1H), 7.44 (dt, J=8.2, 3.1 Hz, 1H), 7.35-7.31 (m, 2H), 5.92 (s, 1H), 5.25 (d, J=12.3 Hz, 1H), 5.07 (s, 1H), 4.94 (td, J=12.5, 6.5 Hz, 2H), 4.68 (d, J=13.4 Hz, 1H), 3.87 (s, 1H), 3.76 (s, 3H), 3.50 (d, J=13.4 Hz, 1H), 2.90 (s, 1H), 2.75 (d, J=12.3 Hz, 1H), 2.44 (s, 1H), 1.96 (d, J=13.2 Hz, 1H), 1.34 (d, J=6.3 Hz, 6H).

Step 13. Synthesis of 1-14

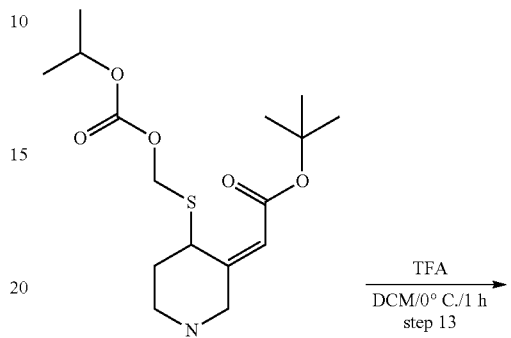

1-10

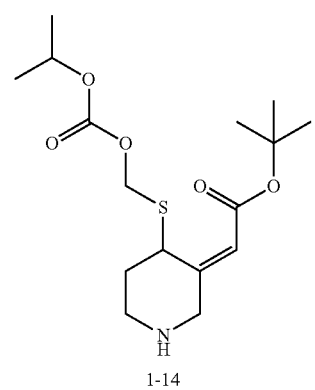

1-14

To a solution of 1-10 (1.8 g, 4.0 mmol) in DCM (10 mL) was added TFA (5 mL) at 0° C., which was stirred at 0° C. for 1 h. After completion, the reaction mixture was added to a solution of sat. NaHCO$_3$ (100 mL), which was then extracted with DCM (100 mL*3). The combined organic layer was dried over Na$_2$SO$_4$, and filtered. The filtrate was concentrated under reduce pressure to give crude 1-14 (2.0 g, >100% yield) as yellow oil, which was used in the next step without further purification. LC-MS [M+1]$^+$=346.1

Step 14. Synthesis of 1-15

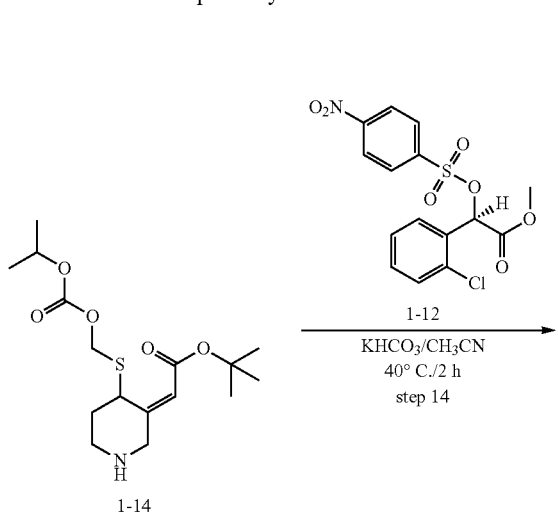

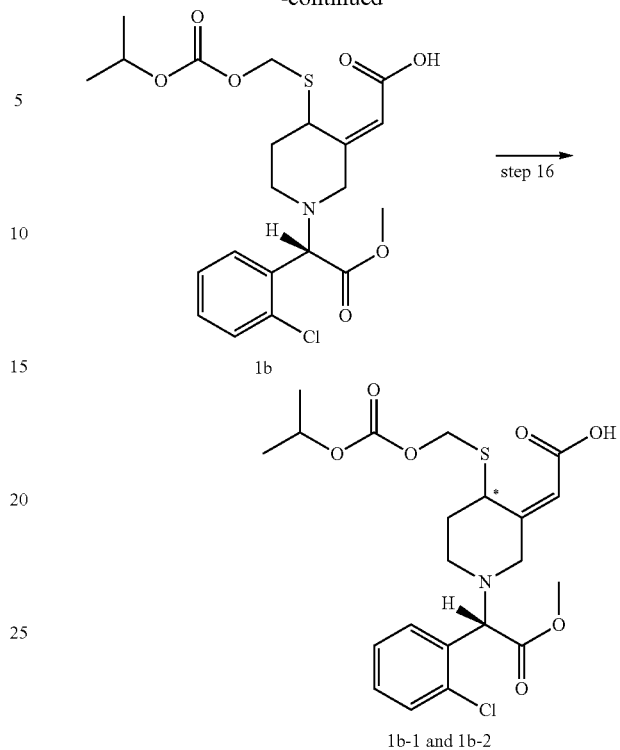

To a solution of 1-14 (2.0 g, crude) in CH₃CN (20 mL) were added 1-12 (1.5 g, 4.0 mmol), and KHCO₃ (800 mg, 8.0 mmol). The resulting mixture was stirred at 40° C. for 2 h and then concentrated under reduce pressure. The residue was purified by reversed-phase column chromatography (C18, CH₃CN/H₂O=80/20) to give 1-15 (500 mg, 24% yield) as a white solid. LC-MS [M+1]$^+$=528.2

Steps 15 and 16. Synthesis of 1b-1 and 1b-2

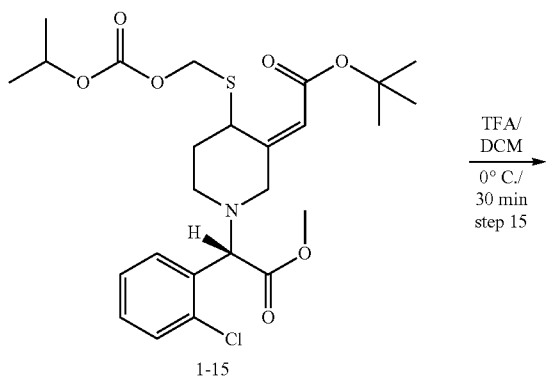

To a solution of 1-15 (500 mg, 0.95 mmol) in DCM (2 mL) at 0° C. was added TFA (3 mL), which was stirred at 0° C. for 30 min. After completion, the reaction was added to a solution of sat. NaHCO₃ (30 mL) which was then extracted with EtOAc (30 mL*3). The combined organic layer was washed with sat. NaHCO₃, dried over Na₂SO₄, and filtered. The filtrate was concentrated under reduce pressure and the residue was purified by reversed-phase column chromatography (C18, CH₃CN/H₂O=80/20), followed by prep-HPLC (Mobile Phase: A (H₂O)/B (MeCN); Range of ratio: A/B (80%/20%) to A/B (55%/45%) 10 min and to A/B (20%/80%) 35 min; Rt of Peak: (67% of B); V=80 mL/min, wavelength 214 nm), and prep-TLC (DCM/MeOH=10/1) to give 1b (50 mg, 11% yield). 1b was purified by chiral column chromatography to give 1b-1 and 1b-2.

1b:
LC-MS [M+1]$^+$=472.1
$^1$H NMR (400 MHz, CDCl₃) δ 7.58 (d, J=5.6 Hz, 1H), 7.44-7.36 (m, 1H), 7.27 (s, 2H), 5.77-5.65 (m, 1H), 5.41 (s, 1H), 5.25 (dd, J=12.0, 6.3 Hz, 1H), 5.19-5.11 (m, 1H), 4.92-4.83 (m, 1H), 4.80 (s, 1H), 3.70 (d, J=4.6 Hz, 3H), 3.52 (dd, J=34.3, 12.2 Hz, 1H), 3.19 (d, J=12.9 Hz, 0.5H), 2.98 (d, J=12.5 Hz, 0.5H), 2.90-2.84 (m, 0.5H), 2.78-2.61 (m, 1.5H), 2.31-2.16 (m, 1H), 1.97-1.82 (m, 1H), 1.28 (d, J=5.4 Hz, 6H).

1b-1:
$^1$H NMR (400 MHZ, CDCl₃) δ 7.60-7.57 (m, 1H), 7.41-7.39 (m, 1H), 7.33-7.26 (m, 2H), 5.64 (s, 1H), 5.41 (s, 1H), 5.25 (d, J=12.1 Hz, 1H), 5.14 (d, J=12.0 Hz, 1H), 4.91-4.81 (m, 1H), 4.79 (s, 1H), 3.69 (s, 3H), 3.47 (d, J=12.4 Hz, 1H), 2.97 (d, J=12.5 Hz, 1H), 2.86 (d, J=10.6 Hz, 1H), 2.72 (dd, J=22.5, 10.6 Hz, 1H), 2.29-2.20 (m, 1H), 1.92 (d, J=14.3 Hz, 1H), 1.27 (d, J=6.2 Hz, 6H).

1b-2:
$^1$H NMR (400 MHZ, CDCl₃) δ 7.62-7.56 (m, 1H), 7.41-7.38 (m, 1H), 7.30-7.26 (m, 2H), 5.77 (s, 1H), 5.43 (s, 1H), δ 5.27 (d, J=12.1 Hz, 1H), 5.17 (d, J=12.0 Hz, 1H), 4.91-4.86 (m, 1H), 4.80 (s, 1H), 3.71 (s, 3H), 3.56 (d, J=12.4 Hz, 1H), 3.17 (d, J=12.4 Hz, 1H), 2.66 (d, J=8.0 Hz, 2H), 2.20-2.17 (m, 1H), 1.87 (d, J=14.4 Hz, 1H), 1.29 (dd, J=6.2, 2.5 Hz, 6H).

Example 2
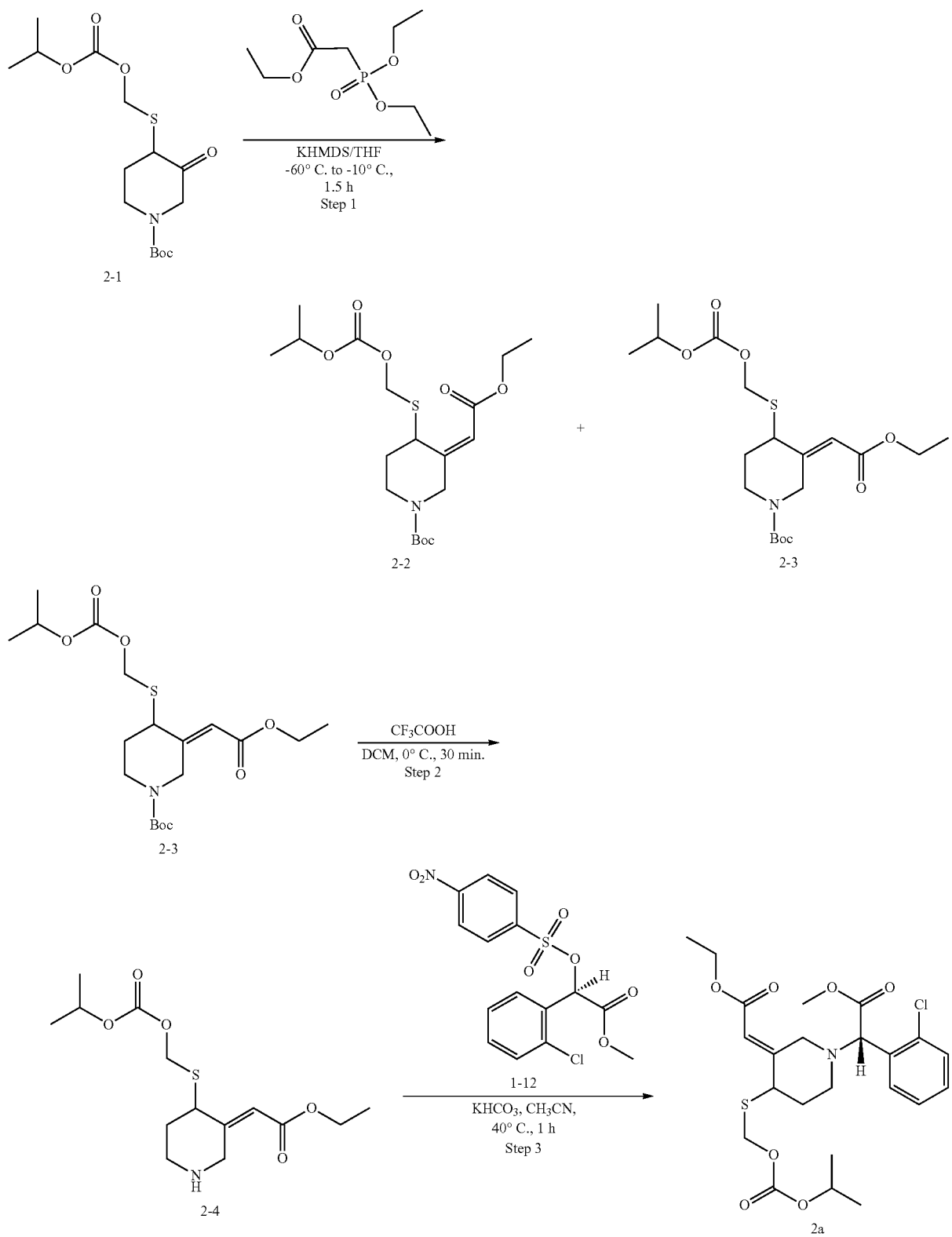

-continued
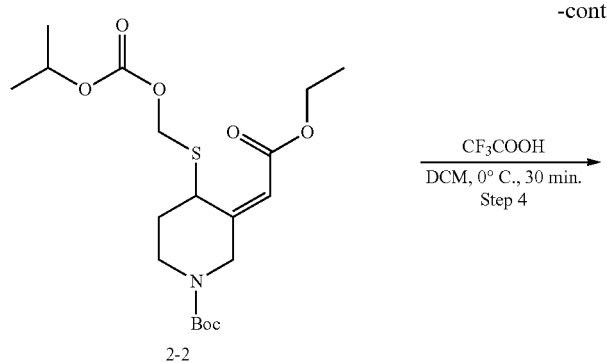
2-2
CF₃COOH
DCM, 0° C., 30 min.
Step 4
→
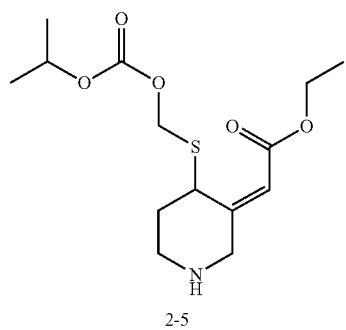
2-5
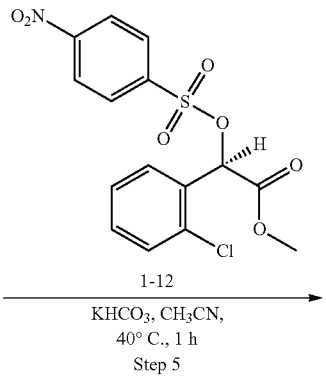
1-12
KHCO₃, CH₃CN,
40° C., 1 h
Step 5
→
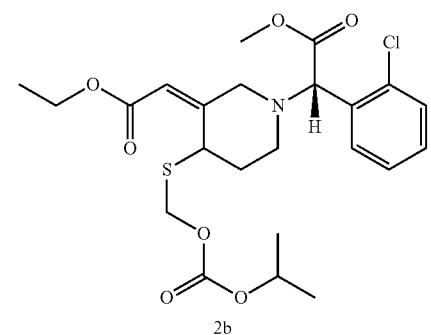
2b
Step 1. Synthesis of 2-2 and 2-3
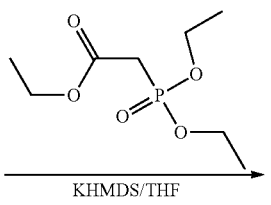
2-1
KHMDS/THF
-60° C. to -10° C.,
1.5 h
Step 1
→
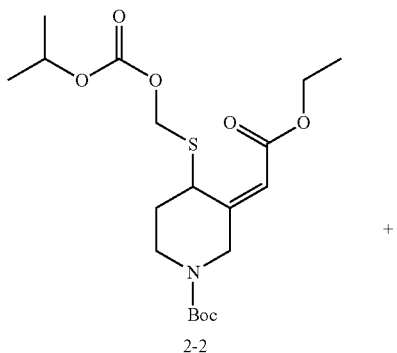
2-2
+
-continued

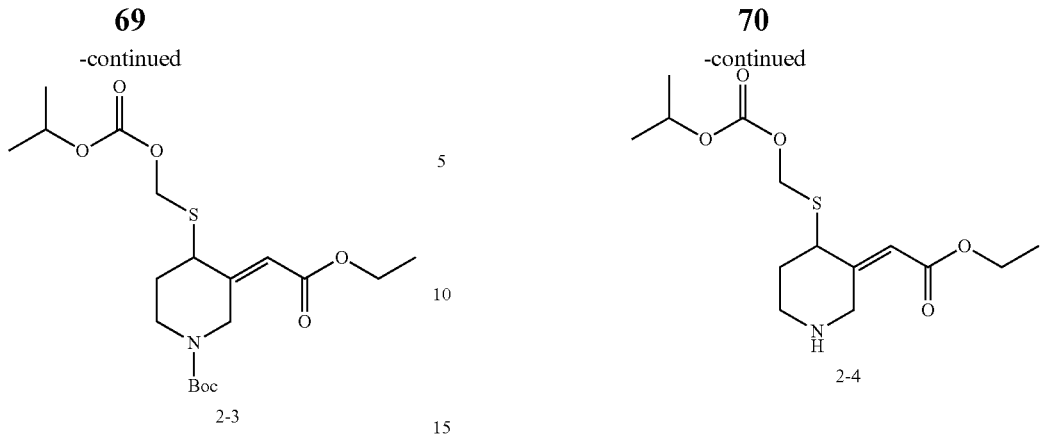

2-3

To a solution of ethyl 2-(diethoxyphosphoryl) acetate (20.6 g, 86.5 mmol) in THF (300 mL) was added KHMDS (75 mL, 74.9 mmol) at −60° C. under $N_2$, which was stirred at −60° C. for 1 h. 2-1 (20.0 g, 57.6 mmol) was then added dropwise at −60° C., and the resulting mixture was stirred at −10° C. for 0.5 h. Then the reaction mixture was added to sat. $NH_4$+Cl (1000 mL). The resulting mixture was extracted with EtOAc (500 mL*2). The combined organic layers were washed with brine, dried over $Na_2SO_4$ and filtered. The filtrate was concentrated under vacuum and the residue was purified by silica gel chromatography (Petroleum ether/EtOAc=60/1) to give 2-3 (7.5 g, 30% yield) as light yellow oil and 2-2 (4.5 g, 18% yield) as light yellow oil.

2-2: $^1$H NMR (400 MHZ, $CDCl_3$) δ 5.76 (s, 1H), 5.50 (d, J=15.8 Hz, 1H), 5.23 (d, J=12.1 Hz, 1H), 4.97-4.83 (m, 2H), 4.23-4.06 (m, 3H), 4.01-3.91 (m, 1H), 3.91-3.77 (m, 2H), 3.28-3.12 (m, H), 2.23-2.10 (m, 1H), 1.88 (dd, J=23.1, 11.5 Hz, 1H), 1.42 (s, 9H), 1.31-1.24 (m, 9H).

2-3: $^1$H NMR (400 MHZ, $CDCl_3$) δ 5.83 (s, 1H), 5.48 (s, 1H), 5.28 (d, J=12.1 Hz, 1H), 5.16 (d, J=12.1 Hz, 1H), 4.94-4.82 (m, 1H), 4.32-4.09 (m, 3H), 4.03-3.85 (m, 2H), 3.23-3.05 (m, 1H), 2.08-1.98 (m, 1H), 1.89 (dd, J=14.2, 1.9 Hz, 1H), 1.44 (s, 10H), 1.31-1.23 (m, 10H).

Step 2. Synthesis of 2-4

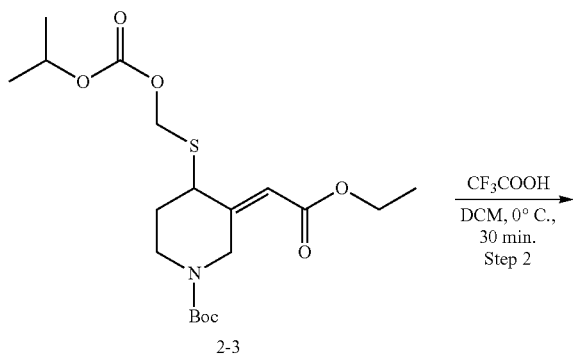

To a solution of 2-3 (3.0 g, 7.2 mmol) in DCM (20 mL) was added TFA (9 mL) at 0° C., the reaction mixture was stirred at 0° C. for 30 min. After completion, the resulting mixture was added to a solution of sat. $NaHCO_3$ (200 mL). The resulting mixture was then extracted with DCM (200 mL). The organic layer was dried over $Na_2SO_4$ and filtered. The filtrate was concentrated under reduce pressure to give crude 2-4 (3.0 g, >100% yield) as yellow oil, which was used in next step without further purification.

LC-MS $[M+1-100]^+$=318.1

Step 3. Synthesis of 2a

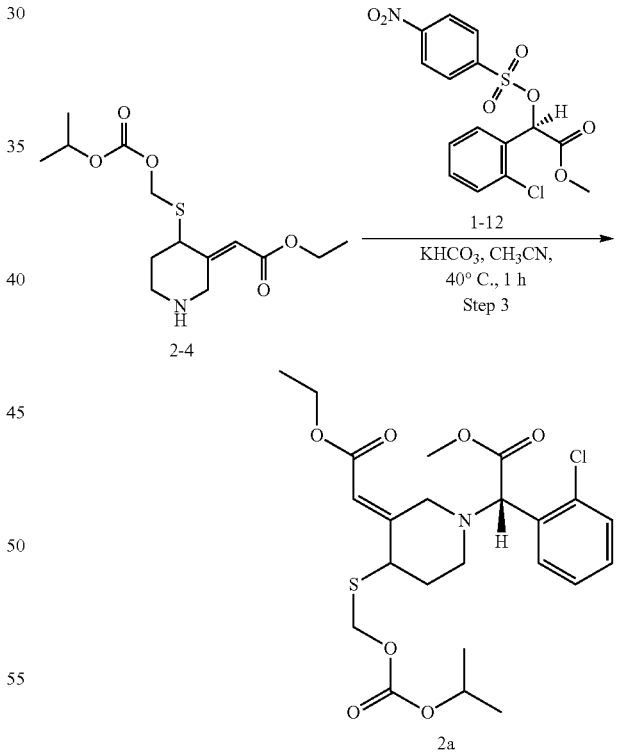

To a solution of 2-4 (3.0 g, crude) in $CH_3CN$ (15 mL) were added 1-12 (2.8 g, 7.2 mmol) and $KHCO_3$ (1.4 g, 14.4 mmol). The resulting mixture was stirred at 40° C. for 1 h. After completion, the reaction mixture was concentrated under reduce pressure and the residue was purified by reversed-phase column chromatography (C18, $CH_3CN$/$H_2O$-80/20) to give 2a (1.7 g, 47% yield).

LC-MS $[M+1]^+$=500.1

¹H NMR (400 MHZ, CDCl₃) δ 7.66-7.52 (m, 1H), 7.43-7.32 (m, 1H), 7.25 (s, 2H), 5.80 (s, 1H), 5.22 (d, J=12.2 Hz, 1H), 4.97-4.79 (m, 3H), 4.49 (dd, J=63.7, 12.8 Hz, 1H), 4.18-3.99 (m, 2H), 3.78 (s, 1H), 3.71 (d, J=7.6 Hz, 3H), 3.47 (dd, J=38.1, 13.2 Hz, 1H), 2.72 (dd, J=45.3, 17.4 Hz, 2H), 2.32 (s, 1H), 1.87 (d, J=13.7 Hz, 1H), 1.30 (d, J=6.1 Hz, 6H), 1.24 (t, J=7.2 Hz, 3H).

Step 4. Synthesis of 2-5

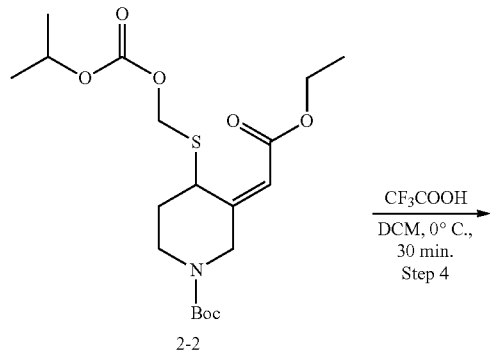

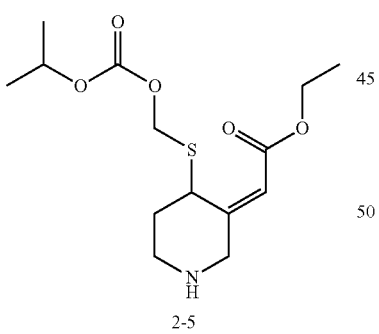

To a solution of 2-2 (100 mg, 0.26 mmol) in DCM (3 mL) was added TFA (0.6 mL) at 0° C., the reaction mixture was stirred at 0° C. for 30 min. After completion, the reaction mixture was added to a solution of sat. NaHCO₃ (20 mL). The resulting mixture was then extracted with DCM (20 mL). The organic layer was dried over Na₂SO₄, and filtered. The filtrate was concentrated under reduce pressure to give crude 2-5 (120.0 mg, >100% yield) as yellow oil, which was used in the in the next step without further purification.

LC-MS [M+1-100]⁺=318.1

Step 5. Synthesis of 2b

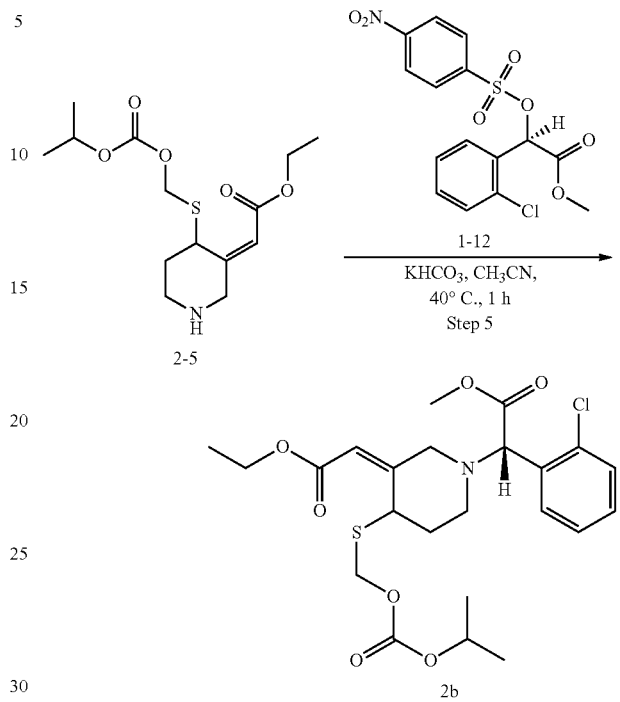

To a solution of 2-5 (120.0 mg, crude) in CH₃CN (3 mL) were added 1-12 (88 mg, 0.23 mmol), and KHCO₃ (92 mg, 0.92 mmol). The resulting mixture was stirred at 40° C. for 1 h. After completion, the reaction mixture was concentrated under reduce pressure and the residue was purified by reversed-phase column chromatography (C18, CH₃CN/H₂O=80/20) to give 2b (23 mg, 20% yield).

LC-MS [M+1]⁺=500.1.

¹H NMR (400 MHZ, CDCl₃) δ 7.59 (d, J=5.1 Hz, 1H), 7.38 (d, J=6.4 Hz, 1H), 7.32-7.25 (m, 2H), 5.74 (s, 0.5H), 5.61 (s, 0.5H), 5.43 (s, 1H), 5.25 (dd, J=11.9, 5.4 Hz, 1H), 5.15 (dd, J=11.9, 4.6 Hz, 1H), 4.93-4.81 (m, 1H), 4.77 (s, 1H), 4.23-4.06 (m, 2H), 3.69 (d, J=3.9 Hz, 3H), 3.51 (d, J=11.9 Hz, 0.5H), 3.42 (d, J=12.1 Hz, 0.5H), 3.14 (d, J=12.3 Hz, 0.5H), 2.97-2.80 (m, 1H), 2.77-2.67 (m, 0.5H), 2.63 (d, J=7.5 Hz, 1H), 2.31-2.10 (m, 1H), 1.88 (dd, J=21.5, 15.1 Hz, 1H), 1.26 (s, 9H).

Example 3

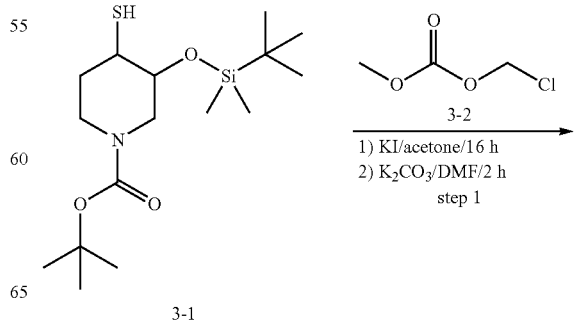

73
-continued
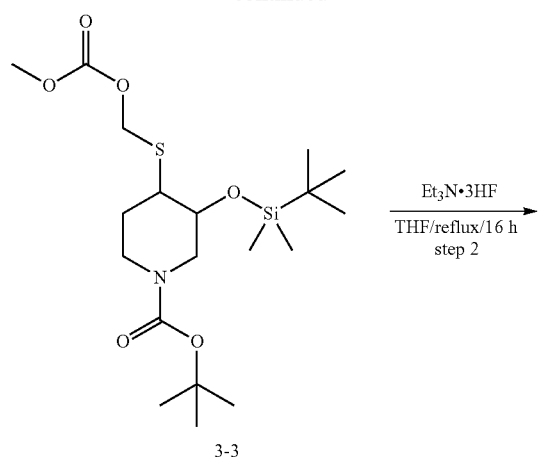
3-3
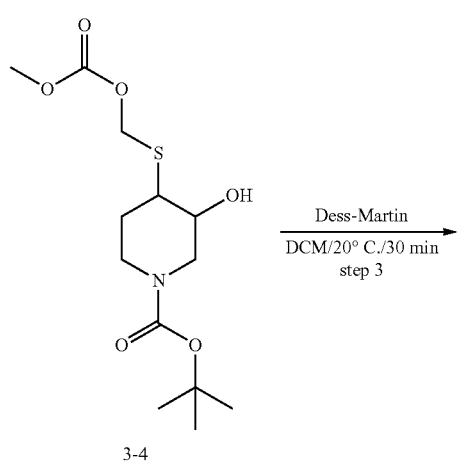
3-4
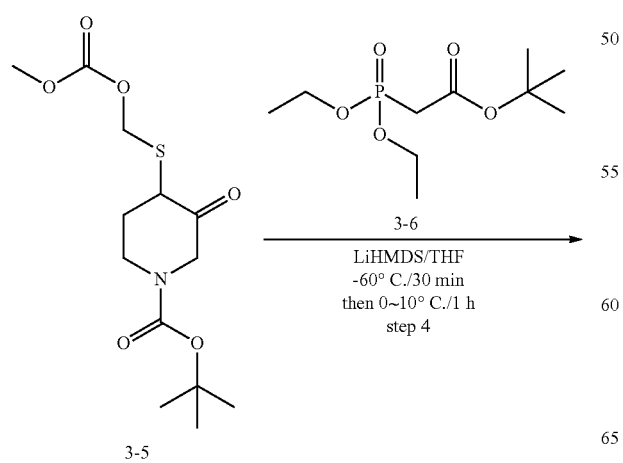
3-5
74
-continued
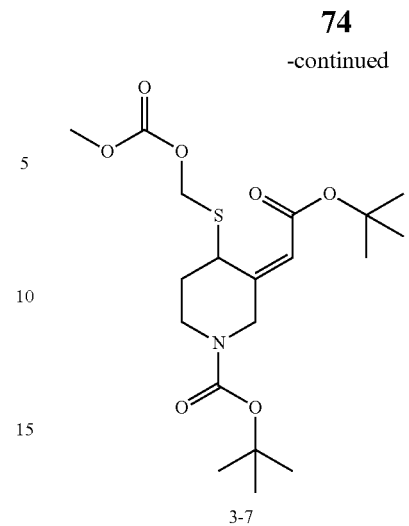
3-7
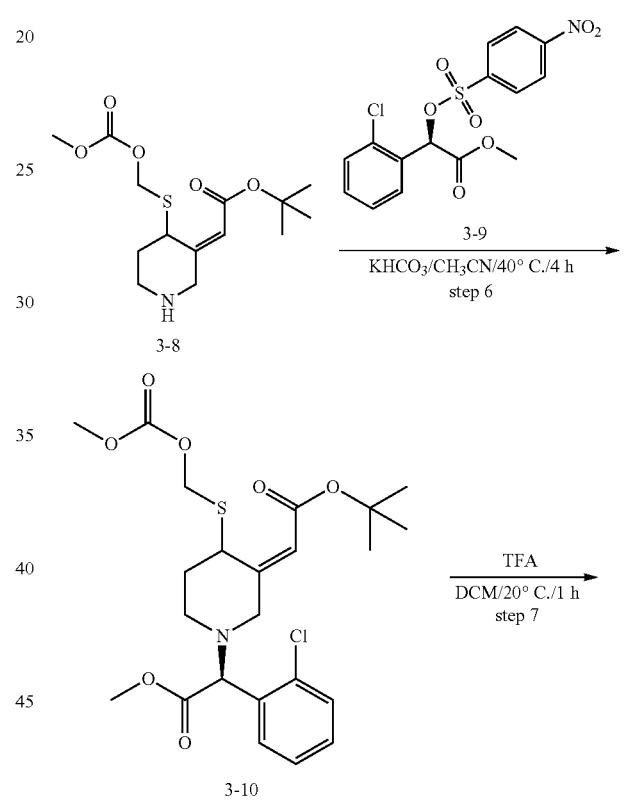
3-8, 3-9, 3-10
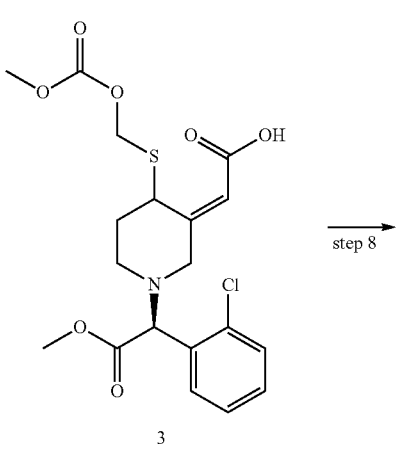
3

-continued

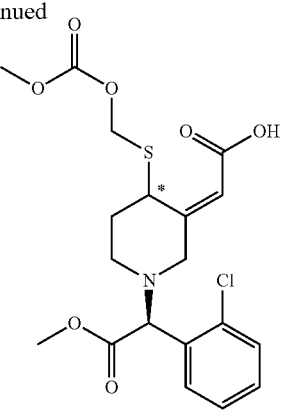

3b-1 and 3b-2

Step 1. Synthesis of 3-3

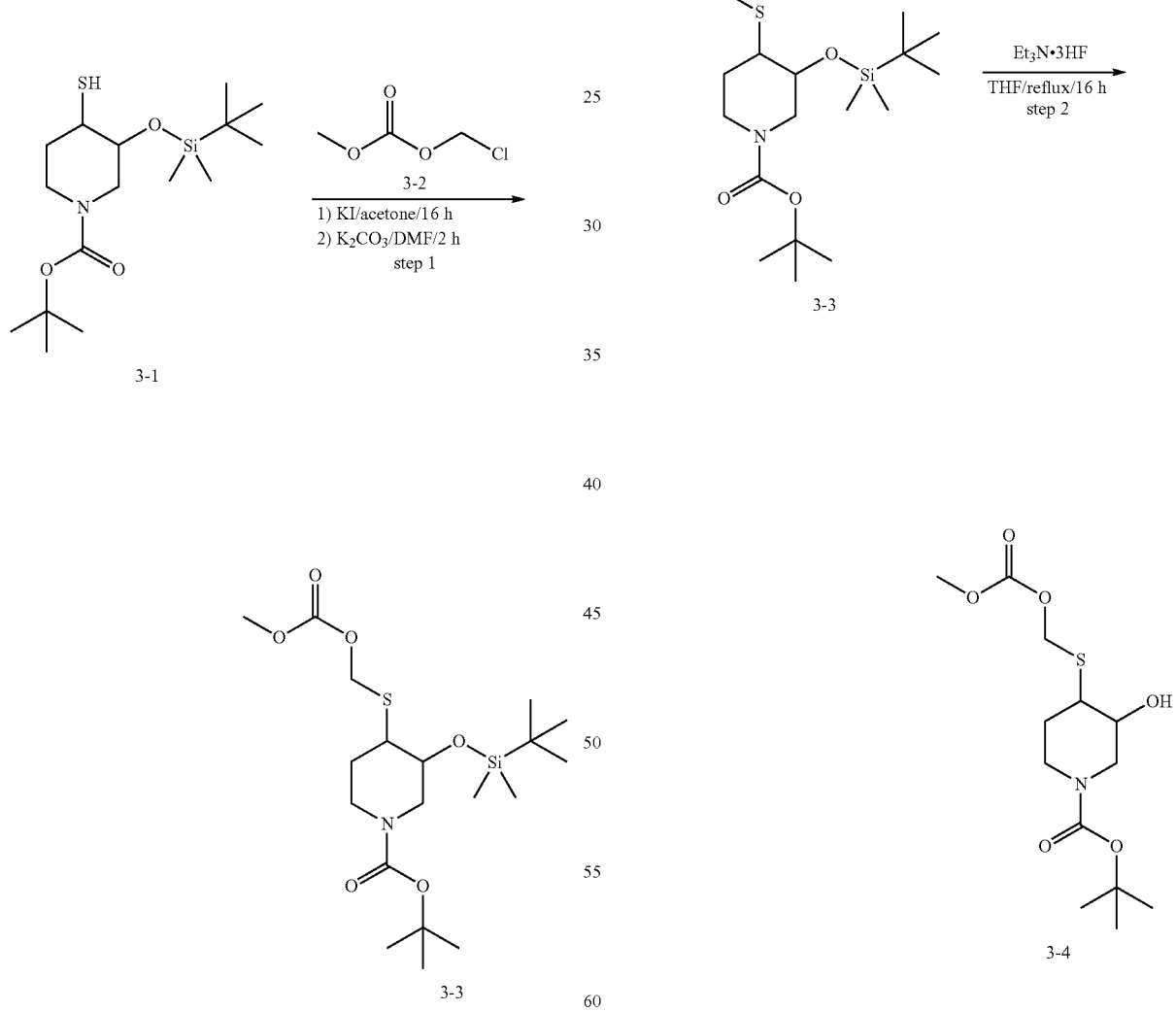

A solution of 3-2 (79.98 g, 0.64 mol) and KI (142.76 g, 0.86 mol) in acetone (1.5 L) was stirred at 16° C. for 16 h. After that, the reaction mixture was concentrated under reduced pressure. The residue was dissolved in DMF (1.5 L) and to the solution above was added 3-1 (150.0 g, 0.43 mol) and K₂CO₃ (88.32 g, 0.64 mol). After addition, the mixture was stirred at 16° C. for 2 h. The reaction was diluted with water (3 L) and extracted by EtOAc (1 L*3). The combined organic layers were dried over anhydrous sodium sulfate and concentrated under reduced pressure. The residue was purified by silica gel chromatography (Petroleum Ether/EtOAc=20/1) to give 3-3 (79.0 g, 28% yield) as colorless oil.

¹H NMR (400 MHZ, Chloroform-d) δ 5.36-5.25 (m, 2H), 4.02-3.91 (m, 1H), 3.88-3.83 (m, 1H), 3.80 (s, 3H), 3.52-3.41 (m, 1H), 2.98-2.84 (m, 2H), 2.84-2.74 (m, 1H), 2.14-2.06 (m, 1H), 1.44 (s, 9H), 0.89 (s, 9H), 0.12 (s, 6H).

Step 2. Synthesis of 3-4

A solution of 3-3 (79.0 g, 0.18 mol) and Et₃N·3HF (90.4 g, 0.54 mol) in THF (800 mL) was refluxed for 16 h under stirred. After cooled down to room temperature, the reaction mixture was concentrated under reduced pressure. The residue was purified by silica gel chromatography (Petroleum Ether/EtOAc=3/1) to give 3-4 (41.0 g, 68% yield) as colorless oil.

Step 3. Synthesis of 3-5

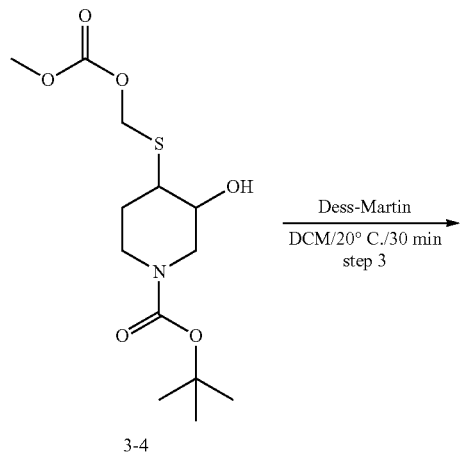

Step 4. Synthesis of 3-7-Z and 3-7-E

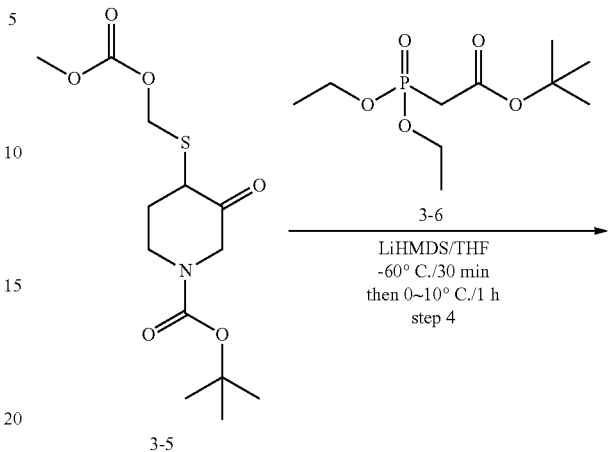

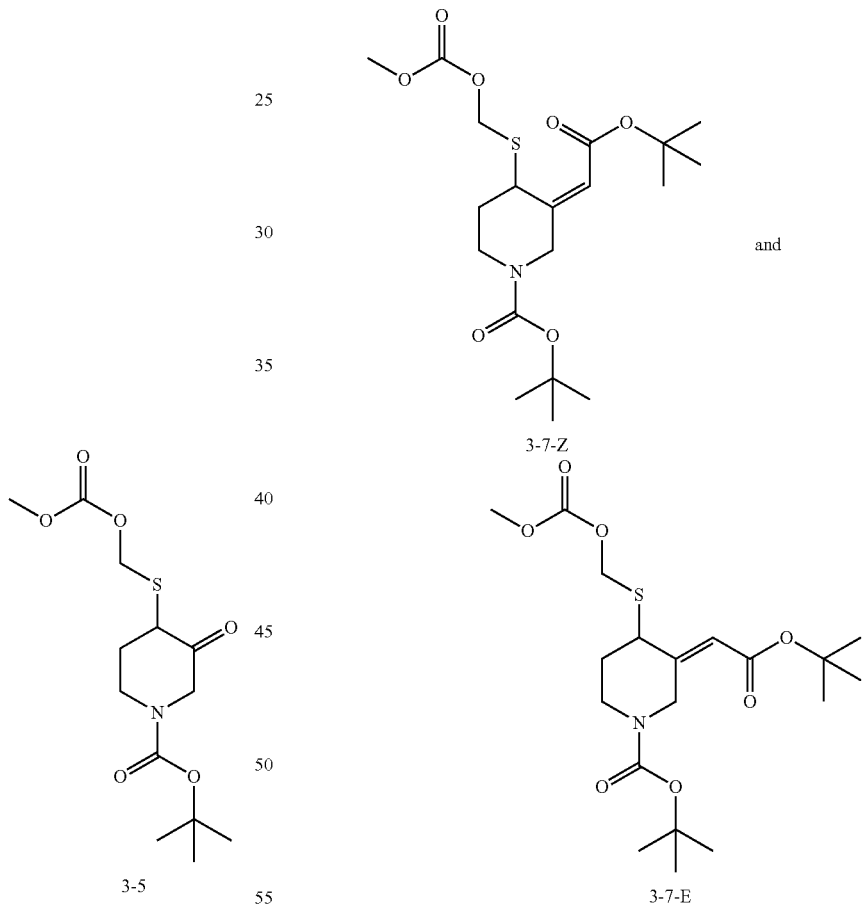

To a solution of 3-4 (41.0 g, 0.12 mol) in DCM (500 mL) was added Dess-Martin (64.9 g, 0.15 mol) at 20° C. After addition, the mixture was stirred at 20° C. for 30 min. The resulting mixture was washed with saturated $Na_2SO_3$ aqueous solution (500 mL), saturated $NaHCO_3$ aqueous solution (500 mL*2) and brine. The organic layer was separated, dried over $Na_2SO_4$, and filtered. The filtrate was concentrated under vacuum and the residue was purified by silica gel chromatography (Petroleum/EtOAc=3/1) to give 3-5 (37.0 g, 92% yield) as yellow oil.

To a solution of 3-6 (37.9 g, 0.15 mol) in dry THF (500 mL) was added LiHMDS (151 mL, 0.15 mol) at −60° C. under $N_2$. The resulting mixture was stirred at −60° C. for 30 min before 3-5 (37.0 g, 0.11 mol) was added dropwise at −60° C. The reaction mixture was warmed up to 0° C. and stirred at 0~10° C. for 1 h. Then the resulting mixture was added to sat. $NH_4Cl$ (100 mL, aq.) and the resulting mixture was extracted with EtOAc (500 mL*2). The combined organic layers were washed with brine, dried over $Na_2SO_4$ and filtered. The filtrate was concentrated under vacuum and the residue was purified silica gel chromatography (Petroleum ether/EtOAc=50/1) to give 3-7-Z (7.0 g, 14% yield) and 3-7-E (14 g, 28% yield).

3-7-Z $^1$H NMR (400 MHZ, Chloroform-d) δ 5.76 (s, 1H), 5.50 (s, 1H), 5.32 (d, J=12 Hz, 1H), 5.17 (d, J=12 Hz, 1H), 4.32-3.87 (m, 3H), 3.79 (s, 3H), 3.24-3.03 (m, 1H), 2.13-2.00 (m, 1H), 1.93-1.85 (m, 1H), 1.47 (s, 9H), 1.45 (s, 9H).

3-7-E $^1$H NMR (400 MHZ, Chloroform-d) δ 5.68 (s, 1H), 5.52-5.43 (s, 1H), 5.26 (d, J=12.4 Hz, 1H), 4.96 (d, J=12.4 Hz, 1H), 3.97-3.85 (m, 2H), 3.80 (s, 3H), 3.79-3.75 (m, 1H), 3.27-3.13 (m, 1H), 2.21-2.09 (m, 1H), 1.93-1.83 (m, 1H), 1.48 (s, 9H), 1.43 (s, 9H).

Step 5. Synthesis of 3-8

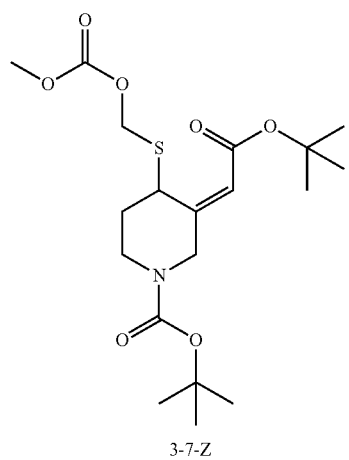

A solution of 3-7-Z (5.5 g, 13.2 mmol) and TsOH·H$_2$O (5.0 g, 26.4 mmol) in DCM (60 mL) was stirred at 20° C. for 16 h. After that, the reaction mixture was diluted with saturated NaHCO$_3$ aqueous solution (100 mL) and extracted by DCM (50 mL*2). The combined organic layers were washed with brine, dried over Na$_2$SO$_4$ and filtered. The filtrate was concentrated under vacuum to give 3-8 (3 g, 71% yield) as yellow oil, which was used to next step without further purification. LC-MS [M+1]$^+$=318.1

Step 6: Synthesis of 3-10

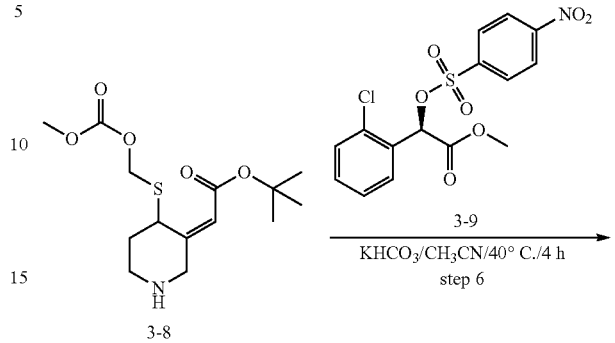

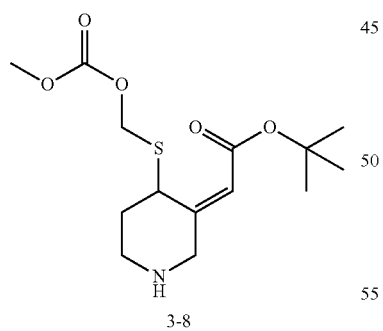

To a solution of 3-8 (3.0 g, 9.4 mmol) in CH$_3$CN (10 mL) were added 3-9 (3.6 g, 9.4 mmol) and KHCO$_3$ (2.8 g, 28.2 mmol). The resulting mixture was stirred at 40° C. for 4 h. After completion, the reaction mixture was concentrated under reduce pressure and the residue was purified by reversed-phase column chromatography (C18, CH$_3$CN/H$_2$O=90/10) to give 3-10 (2.5 g, 53% yield) as yellow oil. LC-MS [M+1]$^+$=500.2

Steps 7 and 8. Synthesis of 3b-1 and 3b-2

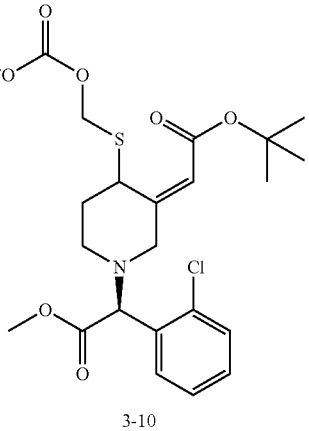

-continued

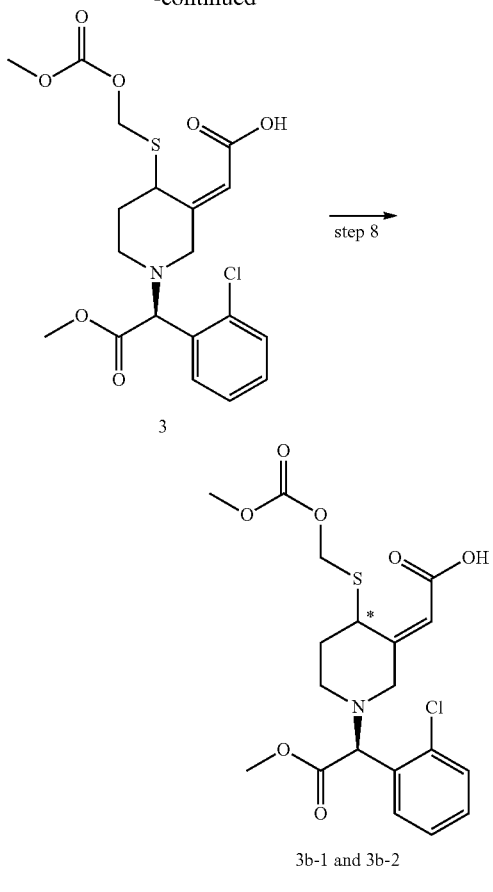

3

3b-1 and 3b-2

To a solution of 3-10 (2.5 g, 5.0 mmol) in DCM (20 mL) was added TFA (5 mL), which was stirred at 20° C. for 1 h. After completion, the reaction was added to a solution of saturated aqueous NaHCO$_3$ solution (50 mL) and extracted with DCM (50 mL*3). The combined organic layers were washed with brine, dried over Na$_2$SO$_4$ and filtered. The filtrate was concentrated under reduce pressure and the residue was purified by Prep-TLC (DCM/MeOH=10/1) to give 3 (800 mg yield 36%). 3 was purified by chiral column chromatography to give 3b-1 and 3b-2.

3:

LC-MS [M+1]$^+$=444.1.

$^1$H NMR (400 MHZ, Chloroform-d) δ 7.60-7.54 (m, 1H), 7.41-7.36 (m, 1H), 7.31-7.22 (m, 2H), 5.77 (s, 0.5H), 5.65 (s, 0.5H), 5.43-5.37 (m, 1H), 5.30-5.23 (m, 1H), 5.19-5.12 (m, 1H), 4.81-4.77 (m, 1H), 3.76 (s, 3H), 3.69 (d, J=4.4 Hz, 3H), 3.54 (d, J=12.4 Hz, 0.5H), 3.45 (d, J=12.4 Hz, 0.5H), 3.17 (d, J=12.4 Hz, 0.5H), 2.96 (d, J=12.4 Hz, 0.5H), 2.85 (d, J=12.0 Hz, 0.5H), 2.73 (d, J=12.0 Hz, 0.5H), 2.70-2.62 (m, 1H), 2.30-2.13 (m, 1H), 2.02-1.82 (m, 1H).

3b-1:

$^1$H NMR (400 MHZ, CDCl$_3$) δ 7.61 (d, J=7.5 Hz, 2H), 7.56-7.41 (m, 2H), 6.10 (s, 1H), 5.71 (s, 1H), 5.52 (s, 1H), 5.27 (q, J=12.2 Hz, 2H), 3.98 (s, 2H), 3.83 (s, 3H), 3.80 (s, 3H), 3.71-3.56 (m, 1H), 3.35-3.14 (m, 1H), 3.01-2.71 (m, 1H), 2.06 (d, J=15.0 Hz, 1H).

3b-2:

$^1$H NMR (400 MHZ, CDCl$_3$) δ 7.64 (s, 1H), 7.56 (d, J=7.6 Hz, 1H), 7.45 (s, 2H), 6.06 (s, 1H), 5.50 (s, 1H), 5.44 (s, 1H), 5.33 (d, J=12.0 Hz, 1H), 5.22 (d, J=11.9 Hz, 1H), 4.02-3.97 (m, 1H), 3.86 (d, J=10.8 Hz, 1H), 3.81 (s, 6H), 3.49 (d, J=13.6 Hz, 1H), 3.12-3.07 (m, 1H), 2.71-2.66 (m, 1H), 2.03 (d, J=14.8 Hz, 1H).

Example 4

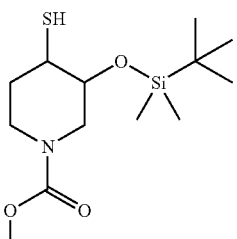
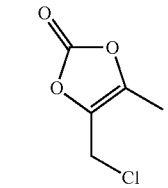

1-5    4-1

1) KI/acetone/3 h/20° C.
2) DMF/20° C./K$_2$CO$_3$/2 h
step 1

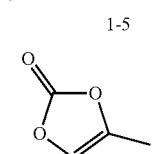

4-2

Et$_3$N·3HF
THF/20° C./16 h
step 2

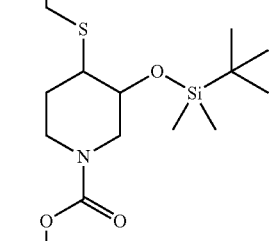

4-3

Dess-martin
DCM/0.5 h/20° C.
step 3

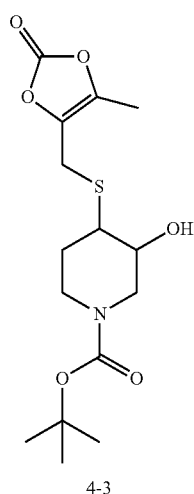

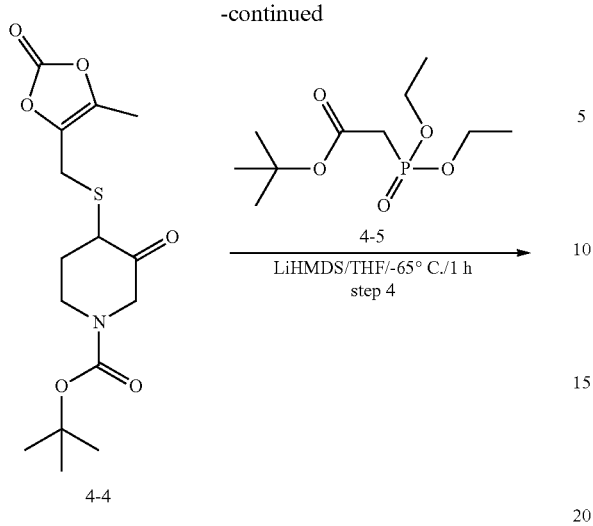
4-4
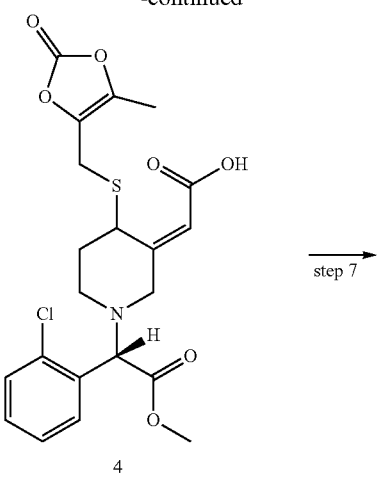
4
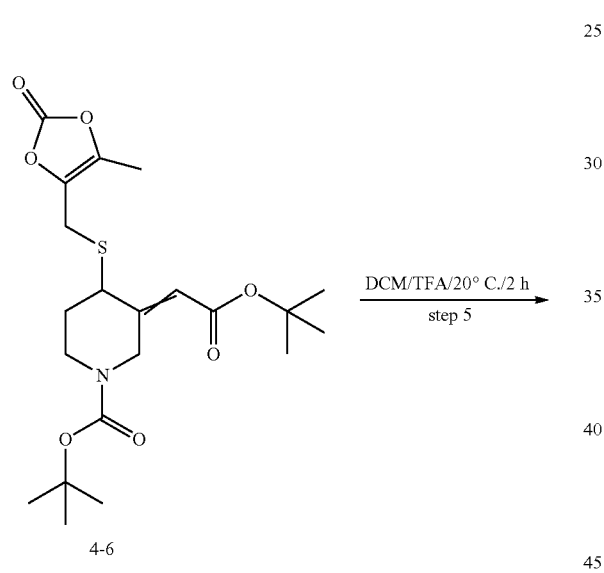
4-6
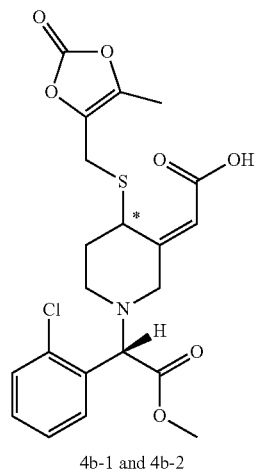
4b-1 and 4b-2
Step 1. Synthesis of 4-2
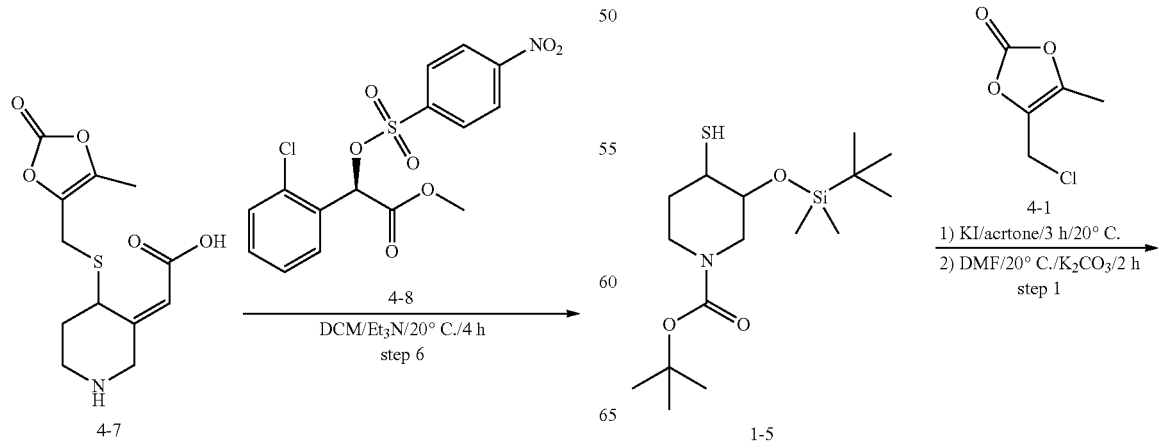

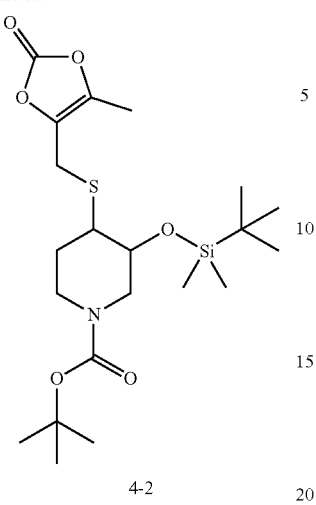

4-2

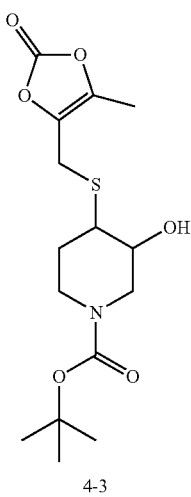

4-3

A solution of 4-1 (64 g, 0.43 mol) and KI (96.3 g, 0.86 mol) in acetone (0.8 L) was stirred at 20° C. for 3 h. The reaction mixture was concentrated under reduced pressure. The residue was dissolved in DMF (1 L). To the solution above was added 1-5 (150.0 g, 0.43 mol) and $K_2CO_3$ (120 g, 0.864 mol). After addition, the resulting mixture was stirred at 20° C. for 2 h. The reaction was diluted with water (2 L) and extracted by EtOAc (600 L*2). The combined organic layers were dried over anhydrous sodium sulfate and concentrated under reduced pressure to give the 4-2 (250 g, 100% yield) as dark oil, which was used to next step without further purification.

A solution of 4-2 (250 g, 0.43 mol) and $Et_3N·3HF$ (210 g, 1.296 mol) in THF (1 L) was stirred at 40° C. for 16 h. The resulting mixture was concentrated under reduced pressure and the residue was diluted with EA (1.5 L). The solution formed was washed with brine (500 ml*2) and the organic layer was separated, dried over $Na_2SO_4$ and concentrated under reduced pressure. The residue was purified by silica gel chromatography (Petroleum Ether/EtOAc=3/1) to give 4-3 (108 g, 73% yield) as white solid. LC-MS $[M+1]^+$-100=246.2.

$^1$H NMR (400 MHZ, $CDCl_3$) δ 4.19 (d, J=12.1 Hz, 1H), 3.98 (s, 1H), 3.72 (s, 1H), 3.52 (d, J=15.2 Hz, 2H), 2.90-2.78 (m, 1H), 2.77-2.67 (m, 1H), 2.66-2.56 (m, 1H), 2.11 (s, 3H), 2.02 (d, J=12.0 Hz, 1H), 1.63-1.49 (m, 1H), 1.45 (s, 9H).

Step 3. Synthesis of 4-4

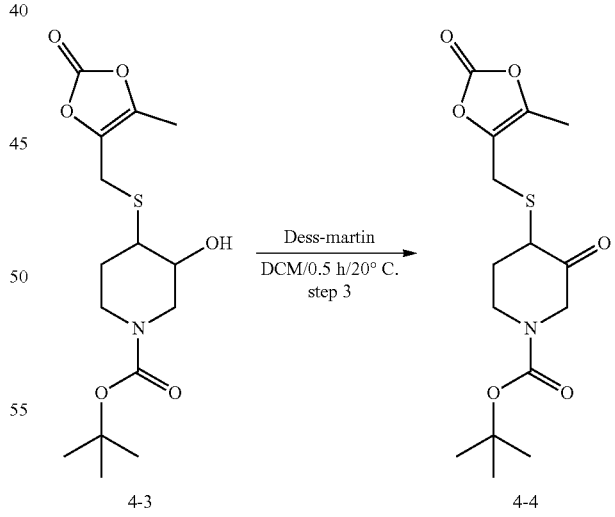

Step 2. Synthesis of 4-3

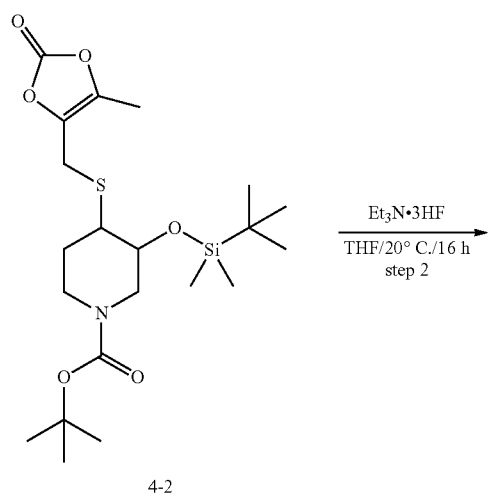

To a solution of 4-3 (108 g, 0.313 mol) in DCM (1 L) was added Dess-Martin (159 g, 0.375 mol) at 20° C. After addition, the resulting mixture was stirred at 20° C. for 30 min. The reaction mixture was washed with saturated $Na_2S_2O_3$ solution (1 L), saturated $NaHCO_3$ solution (1 L*2), brine, dried over $Na_2SO_4$ and concentrated under vacuum. The residue was purified by silica gel chromatography (Petroleum/EtOAc=3/1) to give 4-4 (80.0 g, 74.5% yield) as an orange oil. LC-MS [M+1]$^+$+Na=366.1.

$^1$H NMR (400 MHZ, CDCl$_3$) δ 4.29 (d, J=17.9 Hz, 1H), 4.16 (d, J=18.4 Hz, 1H), 3.82 (s, 1H), 3.48 (d, J=15.6 Hz, 1H), 3.44-3.32 (m, 2H), 3.27 (s, 1H), 2.43-2.29 (m, 1H), 2.16 (s, 3H), 2.09-2.04 (m, 1H), 1.46 (s, 9H).

Step 4. Synthesis of 4-6-Z and 4-6-E

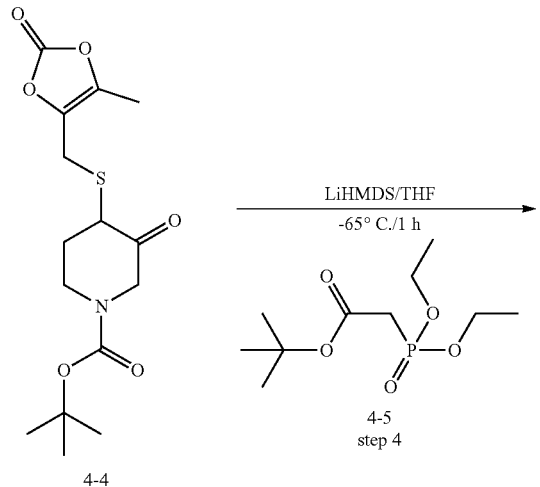

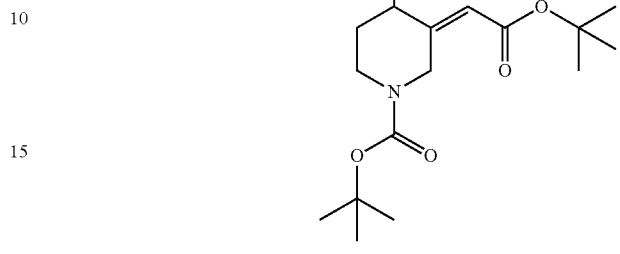

To a solution of 4-5 (77 g, 0.302 mol) in dry THF (800 mL) was added LiHMDS (303 mL, 0.303 mol) at −60° C. under N$_2$. The reaction mixture was stirred at −60° C. for 30 min before 4-4 (80 g, 0.233 mol) was added dropwise at −60° C. The resulting mixture was stirred at 0~10° C. for 1 h. Then the reaction mixture was added to saturated NH$_4$Cl solution (800 mL) and extracted with EtOAc (700 mL*2). The combined organic layers were washed with brine, dried over Na$_2$SO$_4$ and filtered. The filtrate was concentrated under vacuum and the residue was purified by silica gel chromatography (Petroleum ether/EtOAc=20/1) to give 4-6-Z (12 g, 9% yield) as a light orange oil and 4-6-E (15 g, 11% yield) as an off-white solid. LC-MS [M+1]$^+$+23=464.2.

4-6-Z $^1$H NMR (400 MHZ, CDCl$_3$) δ 5.74 (s, 1H), 4.27 (s, 1H), 4.07-3.83 (s, 2H), 3.68 (d, J=15.1 Hz, 1H), 3.44 (d, J=15.2 Hz, 1H), 3.25-3.10 (m, 1H), 2.09 (s, 3H), 2.02 (d, J=14.6 Hz, 1H), 1.85 (d, J=13.7 Hz, 1H), 1.54-1.32 (m, 18H).

4-6-E $^1$H NMR (400 MHZ, CDCl$_3$) δ 5.59 (s, 1H), 5.49 (d, J=15.6 Hz, 1H), 4.00 (d, J=15.7 Hz, 1H), 3.95-3.80 (m, 1H), 3.61 (s, 1H), 3.40-3.14 (m, 3H), 2.21-2.11 (m, 1H), 2.08 (s, 3H), 1.89 (d, J=11.4 Hz, 1H), 1.52-1.42 (m, 18H).

Step 5: Synthesis of 4-7

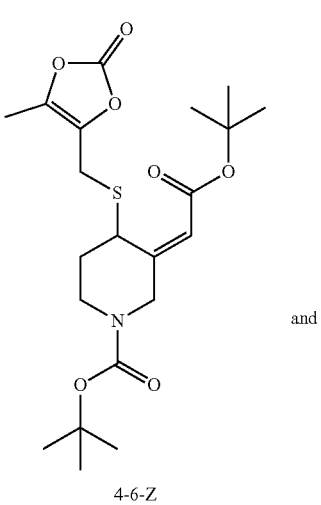

and

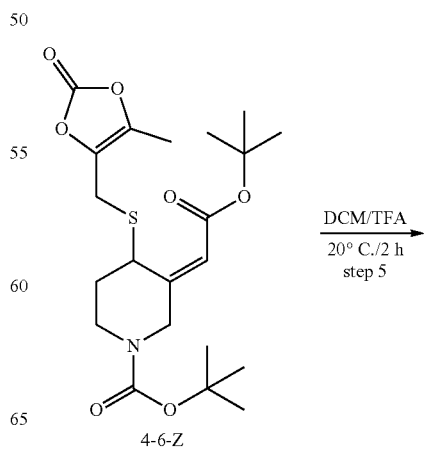

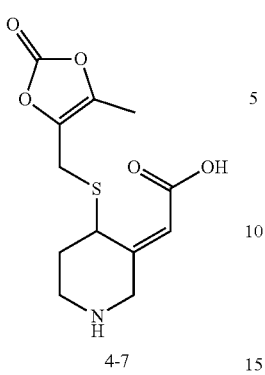

4-7

A solution of 4-6-Z (10 g, 0.023 mol) and TFA (20 ml) in DCM (80 mL) was stirred at 20° C. for 2 h. The resulting mixture was concentrated under vacuum to give 4-7 (15 g, 100% yield) as dark oil, which was used to next step without further purification. LC-MS [M+1]$^+$=286.2.

Steps 6 and 7. Synthesis of 4b-1 and 4b-2

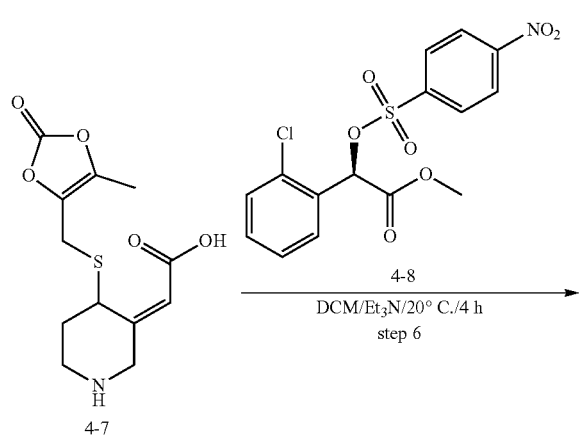

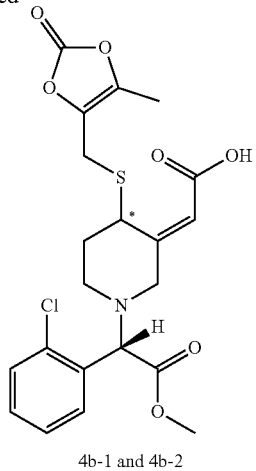

4b-1 and 4b-2

A solution of 4-7 (15 g, crude, 0.023 mol) and 4-8 (5 mL) in DCM was added Et$_3$N dropwise at 20° C. After addition, the mixture was stirred at 20° C. for 4 h. The resulting mixture was concentrated under reduce pressure. The residue was diluted with EA (200 mL) and water (300 ml). The pH value was adjusted to 3 with HCl (1M, aq.). The organic layer was separated, washed with brine, dried over Na$_2$SO$_4$ and concentrated under reduced pressure. The residue was purified by reverse phase column (C18, ACN/H$_2$O=70/30) to give 4 (1.8 g, 16.7% yield). 4 was purified by chiral column chromatography to give 4b-1 and 4b-2.

4:
LC-MS [M+1]$^+$=468.1.
$^1$H NMR (400 MHZ, CDCl$_3$) δ 7.57 (d, J=6.7 Hz, 1H), 7.40 (d, J=6.2 Hz, 1H), 7.32-7.23 (m, 2H), 5.79 (s, 0.5H), 5.67 (s, 0.5H), 5.23 (s, 1H), 4.77-4.67 (m, 1H), 3.71 (d, J=4.5 Hz, 3H), 3.60-3.52 (m, 1.5H), 3.50-3.36 (m, 1.5H), 3.17 (d, J=12.3 Hz, 0.5H), 2.97 (d, J=12.4 Hz, 0.5H), 2.90-2.82 (m, 0.5H), 2.80-2.70 (m, 0.5H), 2.66 (d, J=8.6 Hz, 1H), 2.30-2.13 (m, 1H), 2.06 (s, 3H), 1.93-1.81 (m, 1H).

4b-1:
$^1$H NMR (400 MHZ, CDCl$_3$) δ 7.71-7.63 (m, 1H), 7.50-7.43 (m, 1H), 7.38-7.32 (m, 2H), 5.89 (s, 1H), 5.29 (d, J=4.0 Hz, 1H), 4.94 (s, 1H), 3.77 (s, 3H), 3.67 (dd, J=21.5, 13.7 Hz, 2H), 3.48 (d, J=15.2 Hz, 1H), 3.35 (d, J=12.4 Hz, 1H), 2.79 (t, J=13.1 Hz, 2H), 2.37-2.32 (m, 1H), 2.12 (s, 3H), 1.90 (d, J=14.3 Hz, 1H).

4b-2:
$^1$H NMR (400 MHZ, CDCl$_3$) δ 7.69-7.62 (m, 1H), 7.52-7.44 (m, 1H), 7.41-7.31 (m, 2H), 5.78 (s, 1H), 5.28 (d, J=4.3 Hz, 1H), 4.95 (s, 1H), 3.76 (s, 3H), 3.62 (t, J=15.4 Hz, 2H), 3.46 (d, J=15.3 Hz, 1H), 3.17 (d, J=12.4 Hz, 1H), 3.05-3.00 (m, 1H), 2.87 (t, J=12.4 Hz, 1H), 2.45-2.40 (m, 1H), 2.11 (s, 3H), 1.95 (d, J=14.3 Hz, 1H).

Example 5

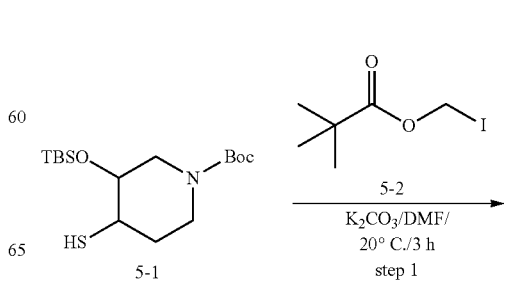

step 1

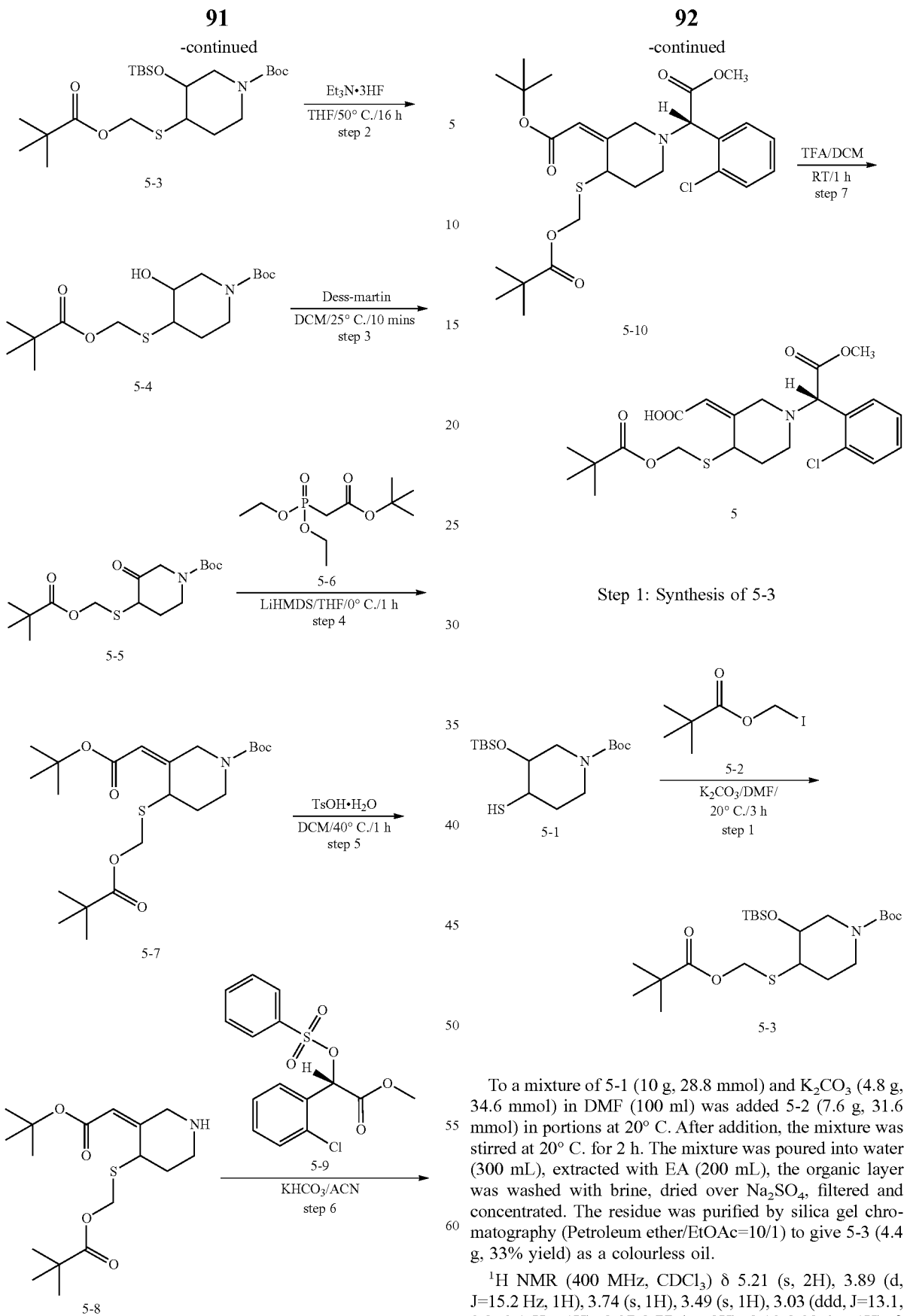

Step 1: Synthesis of 5-3

To a mixture of 5-1 (10 g, 28.8 mmol) and K₂CO₃ (4.8 g, 34.6 mmol) in DMF (100 ml) was added 5-2 (7.6 g, 31.6 mmol) in portions at 20° C. After addition, the mixture was stirred at 20° C. for 2 h. The mixture was poured into water (300 mL), extracted with EA (200 mL), the organic layer was washed with brine, dried over Na₂SO₄, filtered and concentrated. The residue was purified by silica gel chromatography (Petroleum ether/EtOAc=10/1) to give 5-3 (4.4 g, 33% yield) as a colourless oil.

¹H NMR (400 MHz, CDCl₃) δ 5.21 (s, 2H), 3.89 (d, J=15.2 Hz, 1H), 3.74 (s, 1H), 3.49 (s, 1H), 3.03 (ddd, J=13.1, 9.8, 3.1 Hz, 1H), 2.97-2.77 (m, 2H), 2.19-2.02 (m, 1H), δ 1.60-1.49 (m, 1H), 1.44 (s, 9H), 1.20 (s, 9H), 0.89 (s, 9H), 0.11 (s, 6H).

Step 2. Synthesis of 5-4

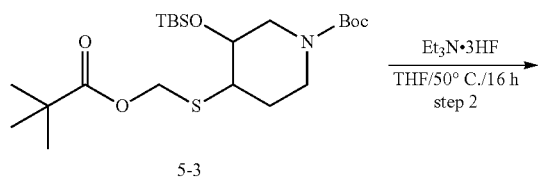

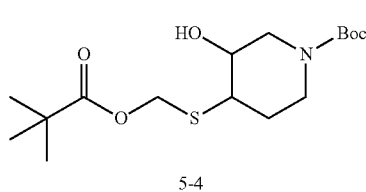

To a solution of 5-3 (4.4 g, 9.5 mmol) in THF (40 mL) was added Et₃N·3HF (4.6 g, 28.6 mmol) and the resulting mixture was stirred at 50° C. for 16 h. After completion, the reaction mixture was concentrated under reduce pressure. The residues purified by silica gel chromatography (Petroleum ether/EtOAc=5/1) to give 5-4 (2.5 g, 76% yield) as a colourless oil.

Step 3. Synthesis of 5-5

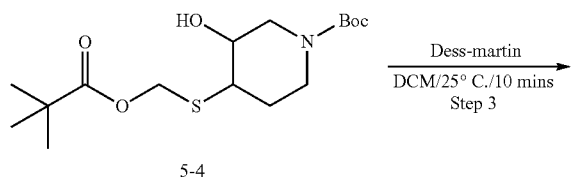

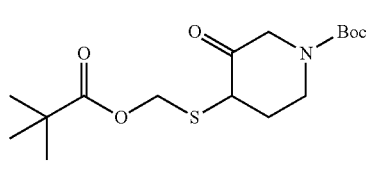

To a solution of 5-4 (2.5 g, 7.2 mmol) in DCM (25 mL) was added Dess-Martin Periodinane (3.9 g, 9.4 mmol), and the resulting mixture was stirred at 25° C. for 30 mins. After completion, the reaction mixture was poured into a mixed solution of sat. Na₂S₂O₃/sat. NaHCO₃ (50 mL, 1:1). The resulting mixture was extracted with DCM (20 mL*2). The combined organic layers was washed with brine, dried over Na₂SO₄, and filtered. The filtrate was concentrated under reduce pressure and the residue was purified by silica gel chromatography (Petroleum ether/EtOAc=3/1) to give 5-5 (2.0 g, 80% yield) as a colourless oil.

Step 4. Synthesis of 5-7

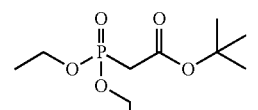

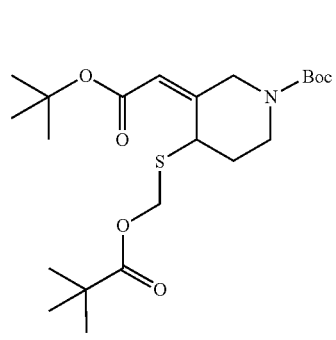

To a solution of 5-6 (1.2 g, 4.8 mmol) in THF (15 mL) was added LiHMDS (4.8 mL, 1M in THF, 4.8 mmol) at −60° C. under N₂, which was stirred at −60° C. for 30 min. 5-5 (1.5 g, 4.4 mmol) was added at −60° C. to the resulting mixture. After addition, the reaction mixture was stirred at 0~10° C. for 1 h. Then the reaction mixture was poured into a sat. NH₄Cl (20 mL) solution and the resulting mixture was extracted with EtOAc (20 mL*2). The combined organic layers were washed with brine, dried over Na₂SO₄ and filtered. The filtrate was concentrated under vacuum. The residues was purified by silica gel chromatography (Petroleum ether/EtOAc=20/1) to give 5-7 (310 mg, 16% yield) as a colourless oil.

¹H NMR (400 MHZ, CDCl₃) δ 5.75 (s, 1H), 5.58 (s, 1H), 5.29 (d, J=12.0 Hz, 1H), 5.18 (d, J=12.0 Hz, 1H), 4.39-4.10 (m, 1H), 4.00 (s, 2H), 3.18 (s, 1H), 2.08 (dd, J=16.1, 9.9 Hz, 1H), 1.91 (d, J=13.8 Hz, 1H), 1.49 (d, J=12.7 Hz, 18H), 1.21 (s, 9H).

Step 5. Synthesis of 5-8

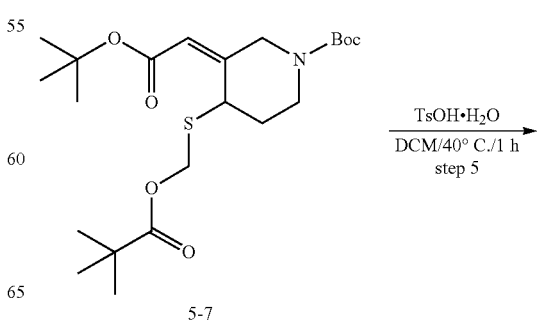

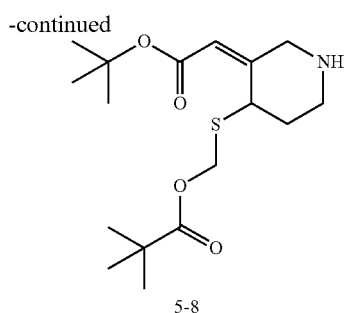

5-8

A mixture of 5-7 (450 mg, 1.01 mmol) and TsOH·H₂O (289 mg, 1.5 mmol) in DCM (10 mL) was stirred at 40° C. for 2 h. After completion, the reaction mixture was poured into a solution of sat. NaHCO₃ (20 mL) and the resulting mixture was extracted with DCM (20 mL*2). The combined organic layers were dried over Na₂SO₄, and filtered. The filtrate was concentrated under vacuum to give the crude 5-8 (450 mg, yield>100%) as a colourless oil.

LC-MS [M+1]⁺=344.3

Step 6. Synthesis of 5-10

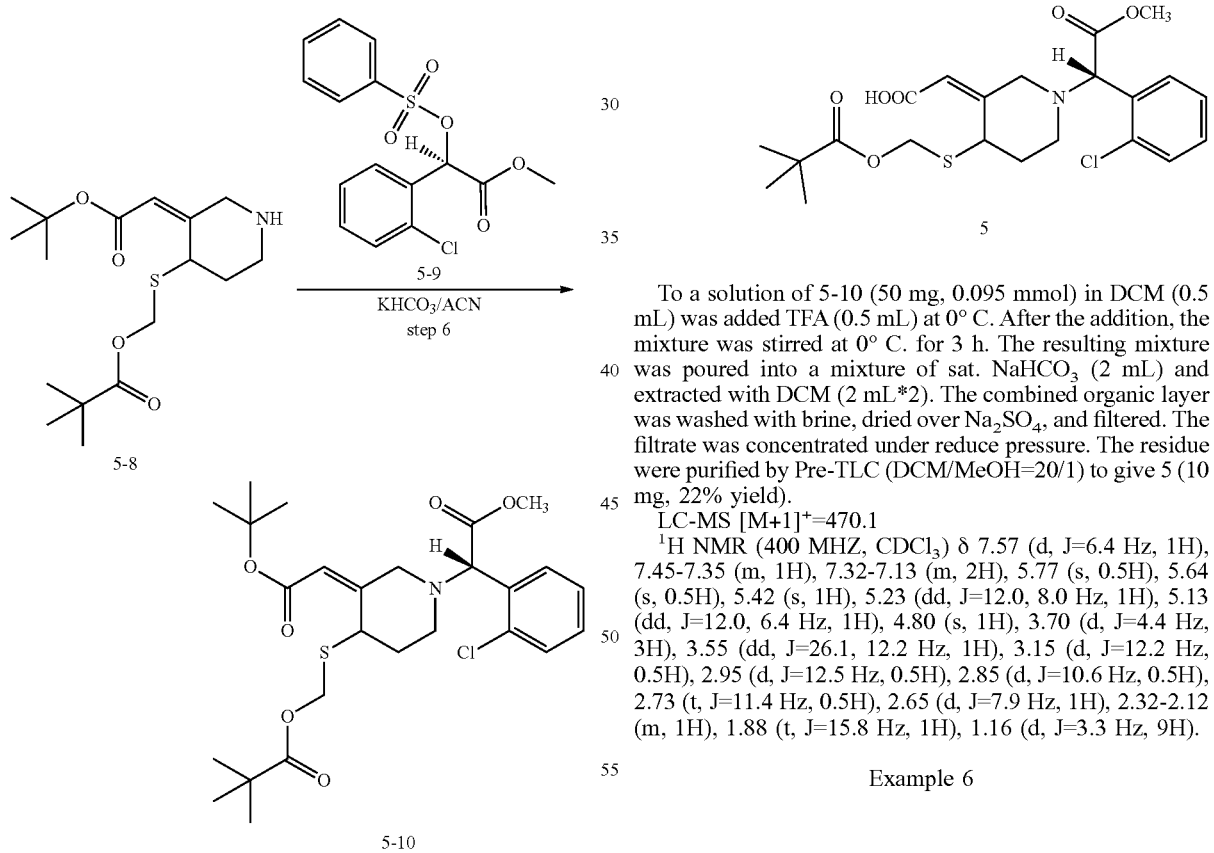

To a solution of 5-8 (crude, 1.01 mmol) in CH₃CN (5 mL) were added 5-9 (389 mg, 1.01 mmol) and KHCO₃ (400 mg, 4.04 mmol). The resulting mixture was stirred at 40° C. for 3 h and filtered. The filtrate was concentrated under reduce pressure, the residue was purified by silica gel chromatography (Petroleum ether/EtOAc=20/1) to give 5-10 (50 mg, 9% yield) as a light yellow oil.

LC-MS [M+1]⁺=526.3

¹H NMR (400 MHZ, CDCl₃) δ 7.60 (d, J=6.4 Hz, 1H), 7.39 (d, J=7.7 Hz, 1H), 7.25 (d, J=11.8 Hz, 2H), 5.68 (s, 1H), 5.51 (d, J=3.7 Hz, 1H), 5.26 (d, J=12.1 Hz, 1H), 5.14 (d, J=12.0 Hz, 1H), 4.77 (s, 1H), 3.70 (s, 3H), 3.52 (d, J=11.9 Hz, 1H), 3.10 (d, J=12.0 Hz, 1H), 2.59 (d, J=8.5 Hz, 2H), 2.28-2.09 (m, 1H), 1.84 (d, J=14.3 Hz, 1H), 1.47 (s, 9H), 1.18 (s, 9H).

Step 7. Synthesis of 5

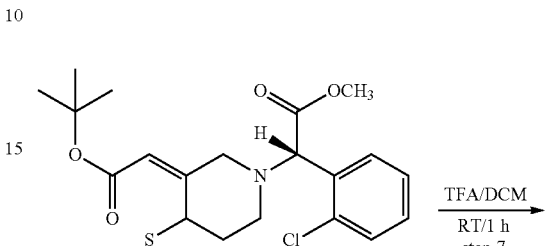

5-10

To a solution of 5-10 (50 mg, 0.095 mmol) in DCM (0.5 mL) was added TFA (0.5 mL) at 0° C. After the addition, the mixture was stirred at 0° C. for 3 h. The resulting mixture was poured into a mixture of sat. NaHCO₃ (2 mL) and extracted with DCM (2 mL*2). The combined organic layer was washed with brine, dried over Na₂SO₄, and filtered. The filtrate was concentrated under reduce pressure. The residue were purified by Pre-TLC (DCM/MeOH=20/1) to give 5 (10 mg, 22% yield).

LC-MS [M+1]⁺=470.1

¹H NMR (400 MHZ, CDCl₃) δ 7.57 (d, J=6.4 Hz, 1H), 7.45-7.35 (m, 1H), 7.32-7.13 (m, 2H), 5.77 (s, 0.5H), 5.64 (s, 0.5H), 5.42 (s, 1H), 5.23 (dd, J=12.0, 8.0 Hz, 1H), 5.13 (dd, J=12.0, 6.4 Hz, 1H), 4.80 (s, 1H), 3.70 (d, J=4.4 Hz, 3H), 3.55 (dd, J=26.1, 12.2 Hz, 1H), 3.15 (d, J=12.2 Hz, 0.5H), 2.95 (d, J=12.5 Hz, 0.5H), 2.85 (d, J=10.6 Hz, 0.5H), 2.73 (t, J=11.4 Hz, 0.5H), 2.65 (d, J=7.9 Hz, 1H), 2.32-2.12 (m, 1H), 1.88 (t, J=15.8 Hz, 1H), 1.16 (d, J=3.3 Hz, 9H).

Example 6

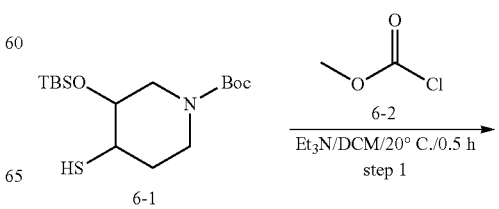

-continued

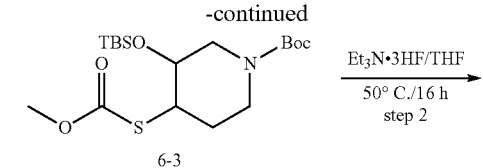
6-3

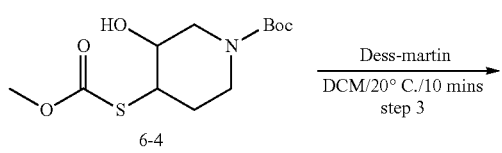
6-4

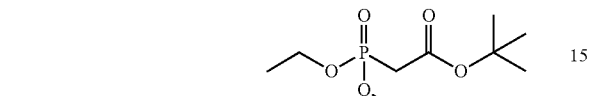

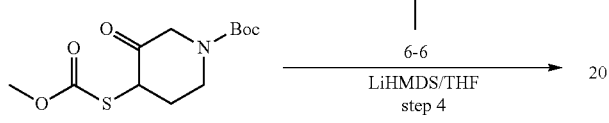
6-5

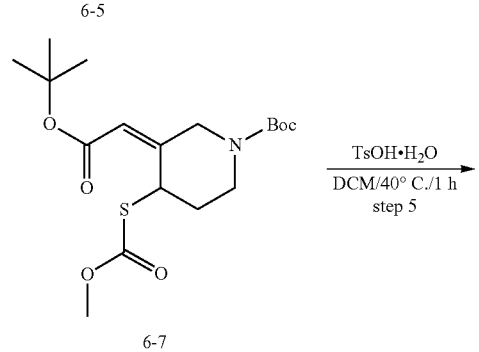
6-7

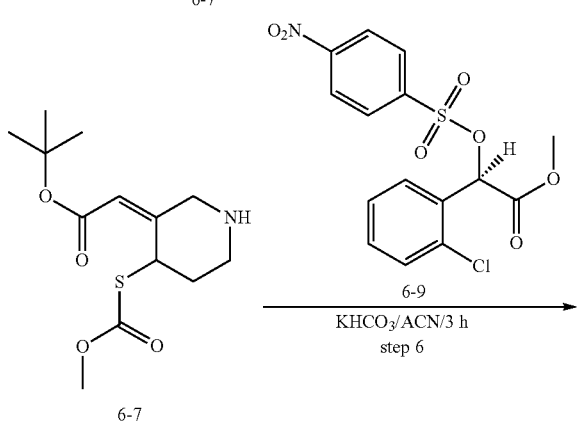
6-7

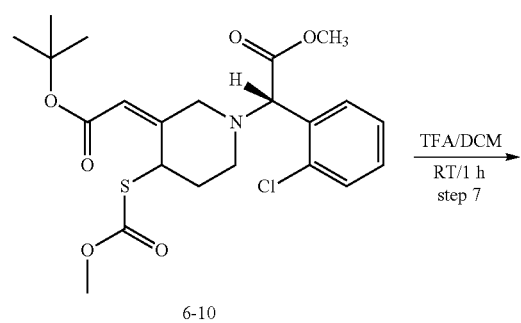
6-10

-continued

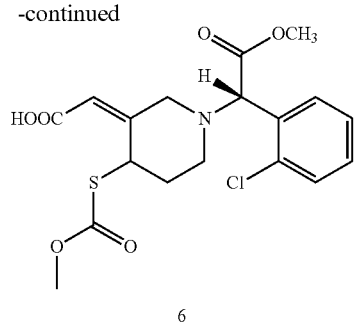
6

Step 1: Synthesis of 6-3

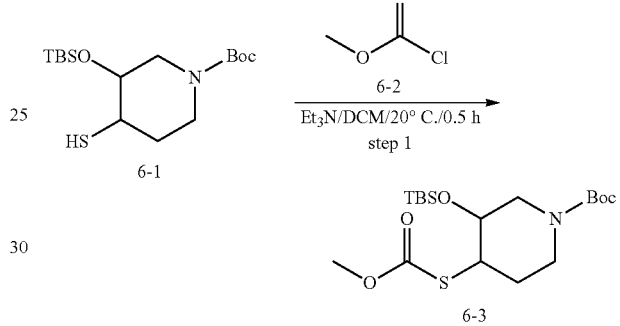

To a mixture of 6-1 (5.00 g, 14.4 mmol) and Et₃N (2.3 g, 20.0 mmol) in DCM (50 ml) was added 6-2 (1.76 g, 18.7 mmol) in portions at 20° C. After addition, the mixture was stirred at 20° C. for 0.5 h. The mixture was concentrated under vacuum. The residue was purified by silica gel chromatography (Petroleum ether/EtOAc=20/1) to give 63 (3.60 g, 62% yield) as a colourless oil.

Step 2: Synthesis of 6-4

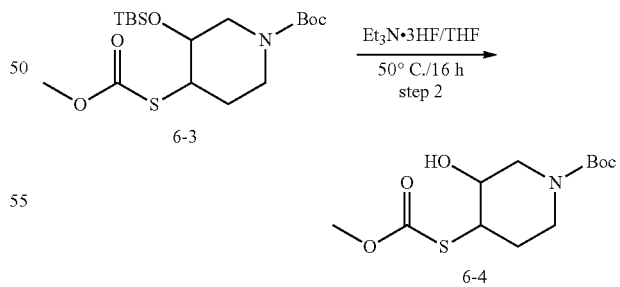

To a solution of 6-3 (3.5 g, 8.6 mmol) in THF (40 mL) was added Et₃N·3HF (4.12 g, 25.9 mmol) and the resulting mixture was stirred at 50° C. for 16 h. After completion, the reaction mixture was concentrated under reduce pressure. The residues purified by silica gel chromatography (Petroleum ether/EtOAc=3/1) to give 6-4 (2.2 g, 88% yield) as a colourless oil.

$^1$H NMR (400 MHZ, CDCl$_3$) δ 4.18 (dd, J=13.3, 4.3 Hz, 1H), 3.91 (s, 1H), 3.82 (s, 3H), 3.53 (s, 1H), 3.33 (td, J=11.0, 4.3 Hz, 1H), 2.91 (s, 1H), 2.87-2.59 (m, 2H), 2.19-2.03 (m, 1H), 1.45 (s, 9H).

Step 3. Synthesis of 6-5

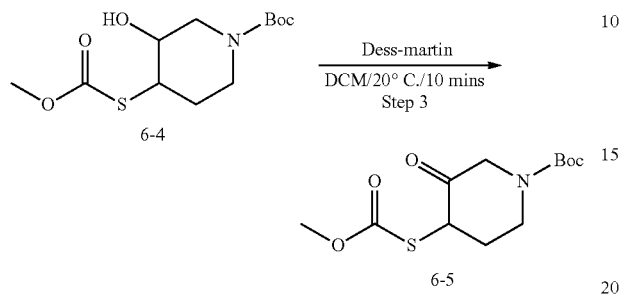

To a solution of 6-4 (2.2 g, 7.56 mmol) in DCM (20 mL) was added Dess-Martin Periodinane (4.1 g, 9.82 mmol), and the resulting mixture was stirred at 25° C. for 10 mins. After completion, the reaction mixture was poured into a mixed solution of sat. Na$_2$S$_2$O$_3$/sat. NaHCO$_3$ (40 mL, 1:1). The resulting mixture was extracted with DCM (20 mL*2). The combined organic layers were washed with brine, dried over Na$_2$SO$_4$, and filtered. The filtrate was concentrated under reduce pressure and the residue was purified by silica gel chromatography (Petroleum ether/EtOAc=5/1) to give 6-5 (1.9 g, 87% yield) as a colourless oil.

Step 4. Synthesis of 6-7

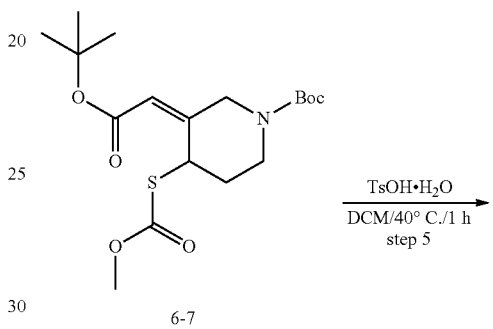

To a solution of 6-6 (1.0 g, 3.80 mmol) in THF (10 mL) was added LiHMDS (3.8 mL, 1M in THF, 3.8 mmol) at −60° C. under N$_2$, which was stirred at −60° C. for 30 min. 6-5 (1.0 g, 3.46 mmol) was added at −60° C. to the resulting mixture. After addition, the reaction mixture was stirred at 0~10° C. for 1 h. Then the reaction mixture was poured into a sat. NH$_4$Cl (20 mL) solution and the resulting mixture was extracted with EtOAc (20 mL*2). The combined organic layers were washed with brine, dried over Na$_2$SO$_4$ and filtered. The filtrate was concentrated under vacuum. The reaction was repeated five times and the residues were combined and purified by silica gel chromatography (Petroleum ether/EtOAc=20/1) to give 6-7 (50 mg, 3.7% yield) as a white solid.

$^1$H NMR (400 MHZ, CDCl$_3$) δ 5.74 (s, 2H), 4.36 (s, 1H), 3.98 (s, 1H), 3.92-3.78 (s, 3H), 3.77-3.48 (m, 1H), 3.21 (s, 1H), 2.24-1.88 (m, 2H), 1.59-1.38 (m, 18H).

Step 5. Synthesis of 6-8

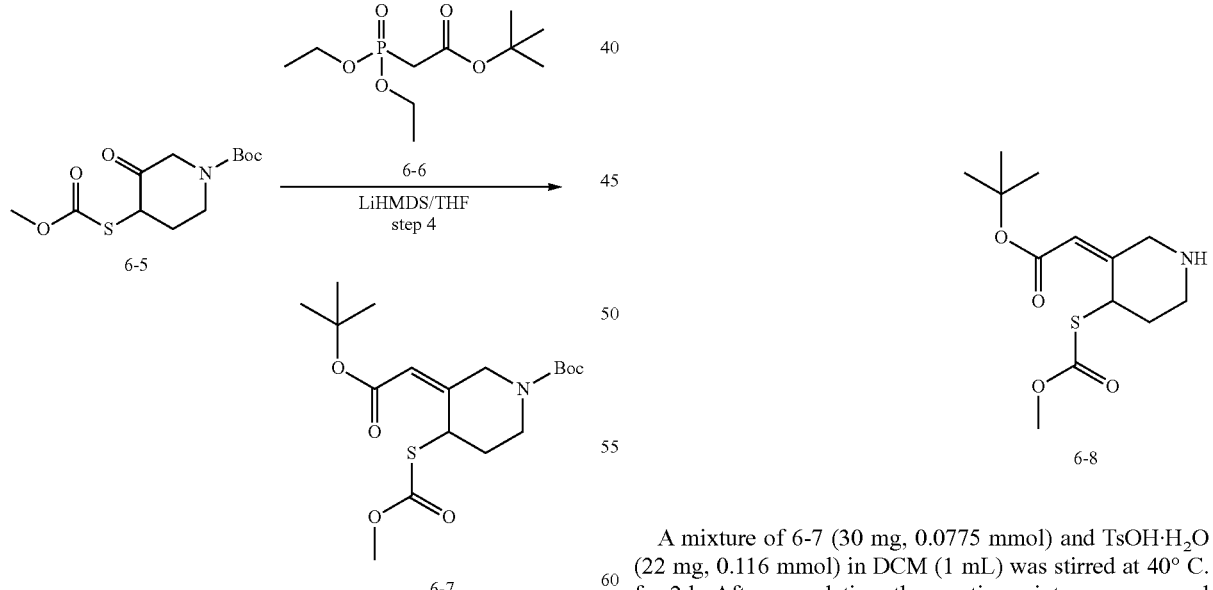

A mixture of 6-7 (30 mg, 0.0775 mmol) and TsOH·H$_2$O (22 mg, 0.116 mmol) in DCM (1 mL) was stirred at 40° C. for 2 h. After completion, the reaction mixture was poured into a solution of sat. NaHCO$_3$ (5 mL) and the resulting mixture was extracted with DCM (2 mL*2). The combined organic layers were dried over Na$_2$SO$_4$, and filtered. The filtrate was concentrated under vacuum to give the crude 6-8 (crude, yield>100%) as a light yellow oil.

LC-MS [M+1]$^+$=288.2

101

Step 6. Synthesis of 6-10

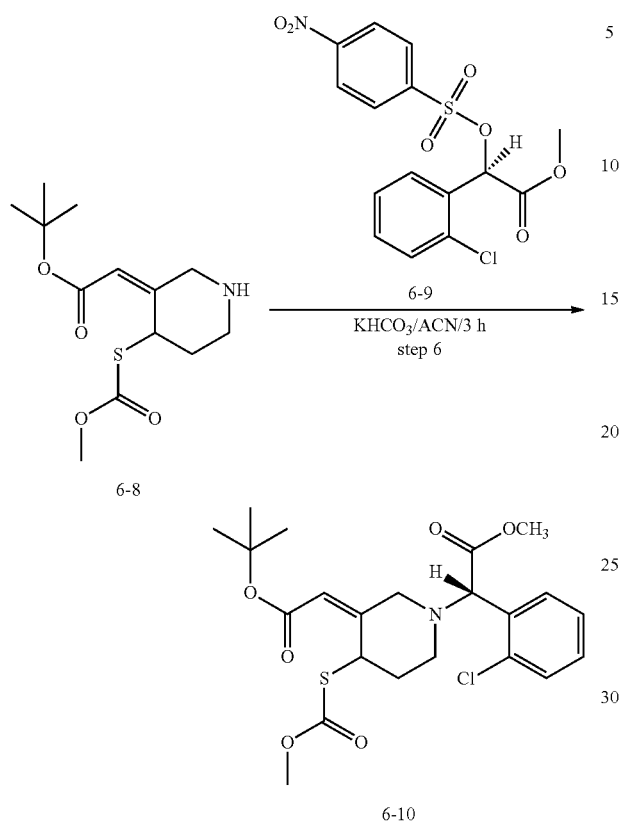

6-8

6-9

KHCO₃/ACN/3 h
step 6

6-10

To a solution of 6-8 (crude, 0.0775 mmol) in CH₃CN (1 mL) were added 6-9 (30 mg, 0.0775 mmol) and KHCO₃ (31 mg, 0.31 mmol). The resulting mixture was stirred at 40° C. for 3 h and filtered. The filtrate was concentrated under reduce pressure, the residue was purified by Prep-TLC (Petroleum ether/EtOAc=10/1) to give 6-10 (10 mg, 28% yield) as a colourless oil.

LC-MS [M+1]⁺=470.2

¹H NMR (400 MHZ, CDCl₃) δ 7.58 (dd, J=8.0, 5.3 Hz, 1H), 7.39 (d, J=8.2 Hz, 1H), 7.27 (d, J=4.9 Hz, 2H), 5.71 (s, 1H), 5.61 (d, J=54.0 Hz, 1H), 4.76 (s, 1H), 3.80 (s, 3H), 3.70 (s, 3H), 3.18 (q, J=12.6 Hz, 1H), 3.11-2.86 (m, 2H), 2.78-2.54 (m, 1H), 2.18 (dd, J=28.3, 12.9 Hz, 1H), 1.95 (dd, J=22.6, 14.5 Hz, 1H), 1.46 (t, J=11.9 Hz, 9H).

Step 7. Synthesis of 6

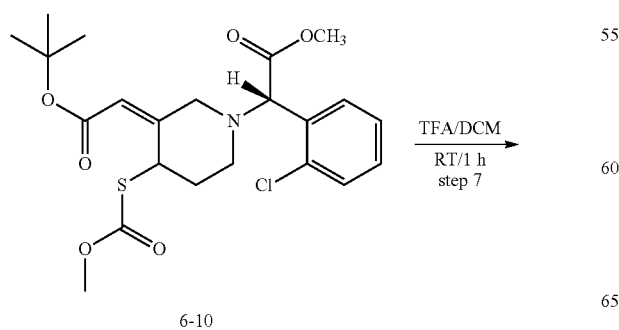

6-10

TFA/DCM
RT/1 h
step 7

102

-continued

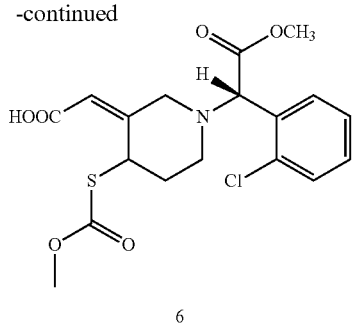

6

To a solution of 6-10 (10 mg, 0.032 mmol) in DCM (0.5 mL) was added TFA (0.5 mL) at 0° C. After the addition, the mixture was stirred at 0° C. for 3 h. The resulting mixture was poured into a mixture of a sat. NaHCO₃ (3 mL), extracted with DCM (2 mL*2). The combined organic layer was washed with brine, dried over Na₂SO₄, and filtered. The filtrate was concentrated under reduce pressure. The residue were purified by Prep-TLC (DCM/MeOH=20/1) to give 6 (5 mg, 38% yield).

LC-MS [M+1]⁺=414.1

¹H NMR (400 MHZ, CDCl₃) δ 7.56 (s, 1H), 7.40 (s, 1H), 7.27 (s, 2H), 5.70 (d, J=31.6 Hz, 2H), 4.79 (s, 1H), 3.79 (s, 3H), 3.71 (s, 3H), 3.25 (s, 1H), 3.12 (dd, J=48.2, 12.7 Hz, 1H), 2.91 (s, 0.5H), 2.84-2.56 (m, 1.5H), 2.23 (s, 1H), 1.97 (dd, J=34.1, 17.2 Hz, 1H).

Example 7

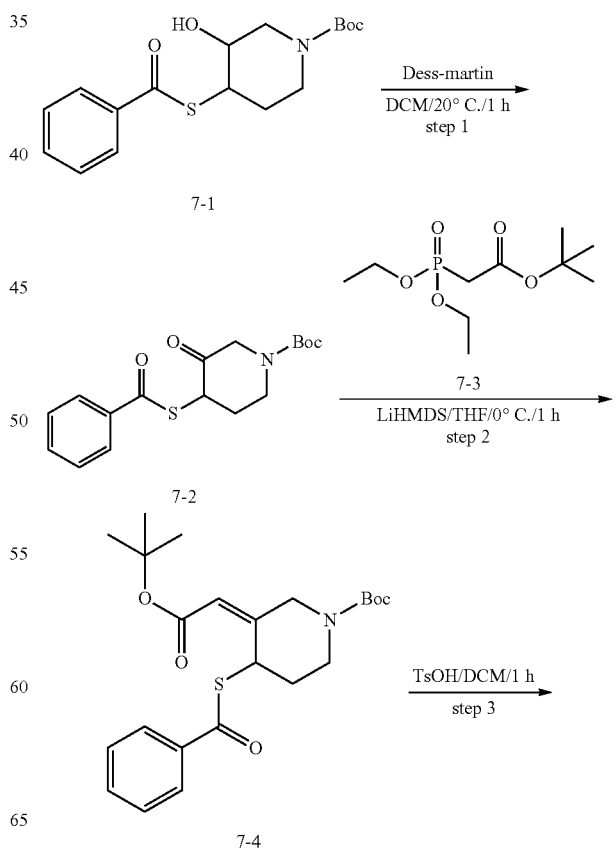

-continued

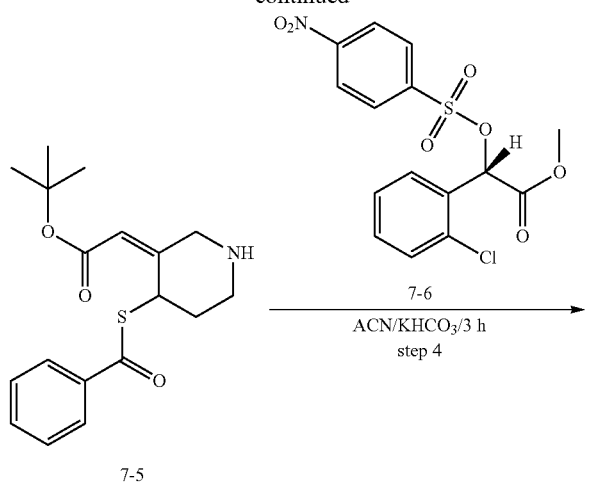

7-5

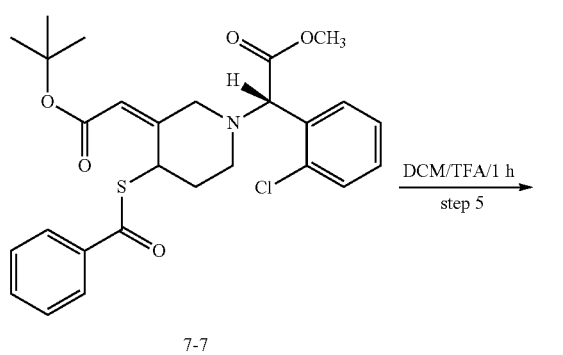

7-7

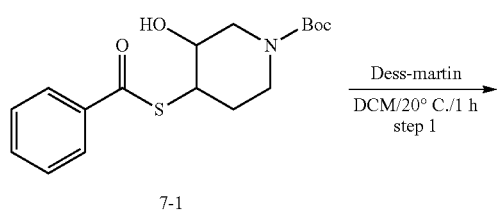

7

Step 1. Synthesis of 7-2

-continued

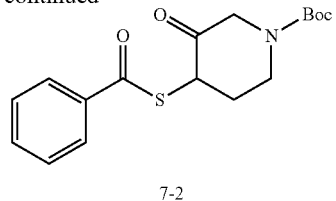

7-2

To a solution of 7-1 (2 g, 5.97 mmol) in DCM (20 mL) was added Dess-Martin Periodinane (3.03 g, 7.16 mol), and the resulting mixture was stirred at 25° C. for 1 h. After completion, the reaction mixture was poured into a mixed solution of sat. Na$_2$S$_2$O$_3$/sat. NaHCO$_3$ (40 mL, 1:1). The resulting mixture was extracted with DCM (20 mL*2). The combined organic layers were washed with brine, dried over Na$_2$SO$_4$, and filtered. The filtrate was concentrated under reduce pressure and the residue was purified by silica gel chromatography (Petroleum ether/EtOAc=5/1) to give 7-2 (1.3 g, 65% yield) as a light yellow oil.

$^1$H NMR (400 MHZ, cdcl$_3$) δ 7.95 (d, J=7.3 Hz, 2H), 7.59 (t, J=7.4 Hz, 1H), 7.45 (t, J=7.7 Hz, 2H), 4.49-4.29 (m, 2H), 4.05 (d, J=17.6 Hz, 2H), 3.48 (s, 1H), 2.58-2.33 (m, 1H), 2.25-2.11 (m, 1H), 1.57-1.44 (s, 9H).

Step 2. Synthesis of 7-4

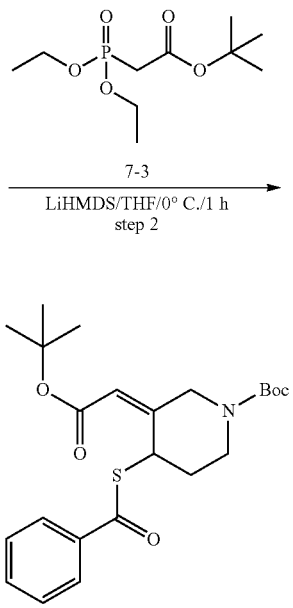

To a solution of 7-3 (1.1 g, 4.3 mmol) in THF (15 mL) was added LiHMDS (4.3 mL, 1M in THF, 4.3 mmol) at −60° C. under N$_2$ and the resulting mixture was stirred at −60° C. for 30 min. 7-2 (1.3 g, 3.9 mmol) was added dropwise at −60° C. to the mixture above. After addition, the reaction mixture was stirred at 0~10° C. for 1 h. Then the reaction mixture was poured into a sat. NH$_4$Cl (30 mL) solution and the resulting mixture was extracted with EtOAc (20 mL*2). The combined organic layers were washed with brine, dried over Na$_2$SO$_4$ and filtered. The filtrate was concentrated under vacuum. The residue was purified by silica gel chromatography (Petroleum ether/EtOAc=20/1) to give 7-4 (65 mg, 3.8% yield) as a white solid.

¹H NMR (400 MHZ, CDCl₃) δ 7.98 (d, J=7.4 Hz, 2H), 7.59 (d, J=6.6 Hz, 1H), 7.47 (t, J=7.1 Hz, 2H), 5.99 (s, 1H), 5.79 (s, 1H), 4.55-4.35 (m, 1H), 4.20-3.91 (m, 1H), 3.83-3.64 (m, 1H), 3.35-3.12 (m, 1H), 2.17 (s, 1H), 2.03 (d, J=14.0 Hz, 1H), 1.62-1.36 (m, 18H).

Step 3. Synthesis of 7-5

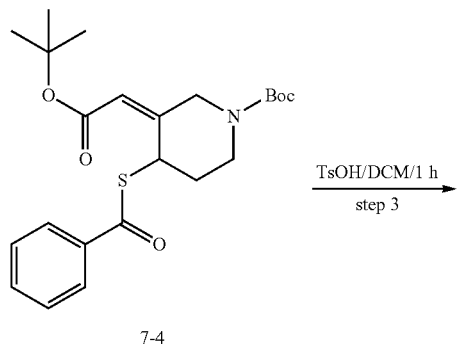

7-4

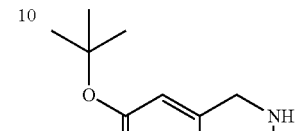

TsOH/DCM/1 h
step 3

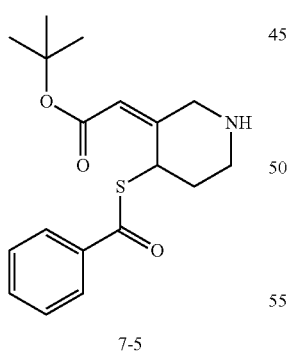

7-5

A mixture of 7-4 (60 mg, 0.138 mmol) and TsOH·H₂O (39 mg, 0.207 mmol) in DCM (2 mL) was stirred at 40° C. for 2 h. After completion, the reaction mixture was poured into a solution of sat. NaHCO₃ (4 mL) and the resulting mixture was extracted with DCM (2 mL*2). The combined organic layers were dried over Na₂SO₄, and filtered. The filtrate was concentrated under vacuum to give the crude 7-5 (50 mg, yield>100%) as a light yellow oil.

Step 4. Synthesis of 7-7

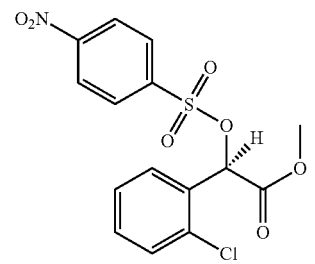

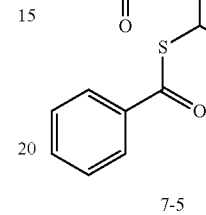

7-5

ACN/KHCO₃/3 h
step 4

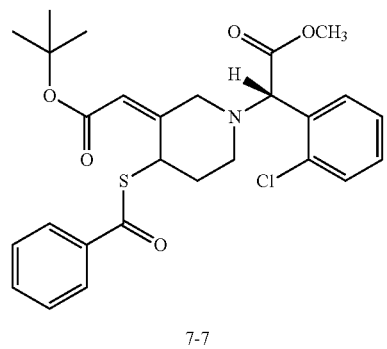

7-7

To a solution of 7-5 (crude, 0.138 mmol) in CH₃CN (2 mL) were added 7-6 (53 mg, 0.138 mmol) and KHCO₃ (55 mg, 0.552 mmol). The resulting mixture was stirred at 40° C. for 3 h. After cooled down to room temperature, the mixture was filtered. The filtrate was concentrated under reduce pressure, the residue was purified by silica gel chromatography (Petroleum ether/EtOAc=10/1) to give 7-7 (20 mg, 28% yield) as a white solid.

LC-MS [M+1]⁺=516.3

Step 5. Synthesis of 7

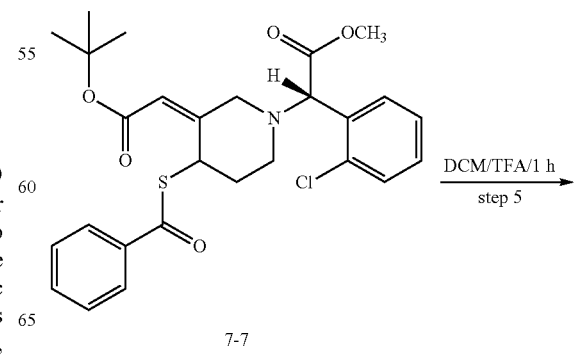

7-7

DCM/TFA/1 h
step 5

107

-continued

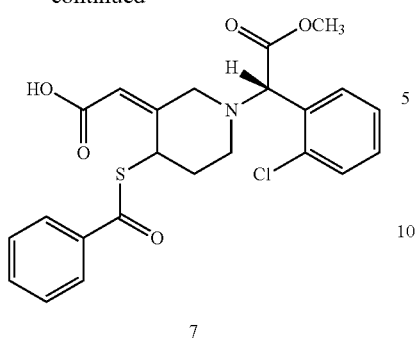

7

To a solution of 7-7 (20 mg, 0.039 mmol) in DCM (1 mL) was added TFA (1 mL) at 0° C. After the addition, the mixture was stirred at 0° C. for 3 h. The resulting mixture was poured into a mixture of sat. NaHCO$_3$ (4 mL) and extracted with DCM (2 mL*2). The combined organic layers were washed with brine, dried over Na$_2$SO$_4$, and filtered. The filtrate was concentrated under reduce pressure. The residue was purified by Prep-TLC (DCM/MeOH=20/1) to give 7 (10 mg, 45% yield).

LC-MS [M+1]$^+$=460.1

$^1$H NMR (400 MHZ, CDCl$_3$) δ 7.89 (d, J=8.2 Hz, 2H), 7.58 (dd, J=7.3, 2.1 Hz, 1H), 7.51 (dd, J=8.9, 5.9 Hz, 1H), 7.42-7.35 (m, 3H), 7.29-7.25 (m, 2H), 6.01 (s, 1H), 5.75 (s, 0.5H), 5.64 (s, 0.5H), 4.77 (d, J=4.5 Hz, 1H), 3.70 (d, J=4.2 Hz, 3H), 3.28 (d, J=12.8 Hz, 1H), 3.12 (dd, J=34.1, 12.4 Hz, 1H), 2.93 (d, J=12.3 Hz, 1H), 2.73 (d, J=9.2 Hz, 0.5H), 2.68-2.57 (m, 1H), 2.33-2.14 (m, 0.5H), 1.88 (t, J=17.4 Hz, 1H).

Example 8

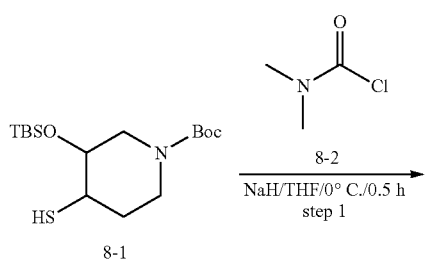

8-1

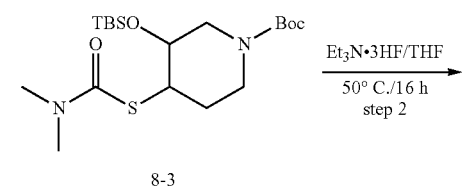

8-3

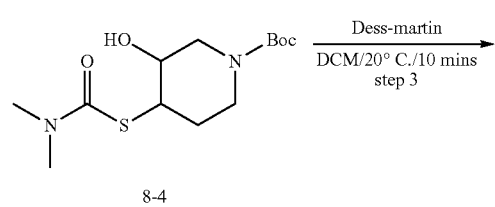

8-4

108

-continued

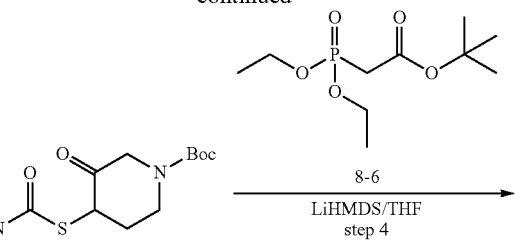

8-5

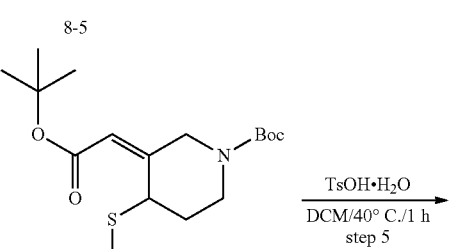

8-7

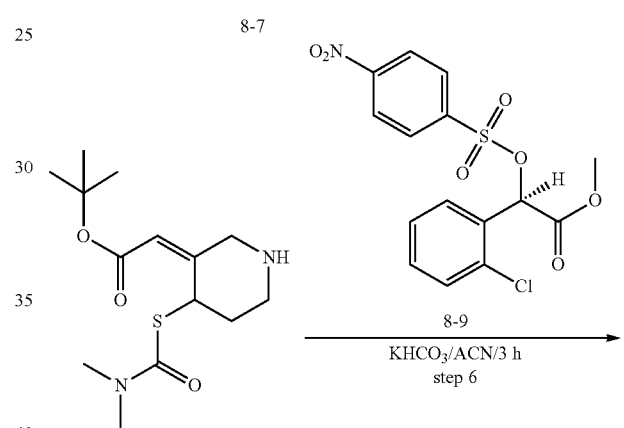

8-8

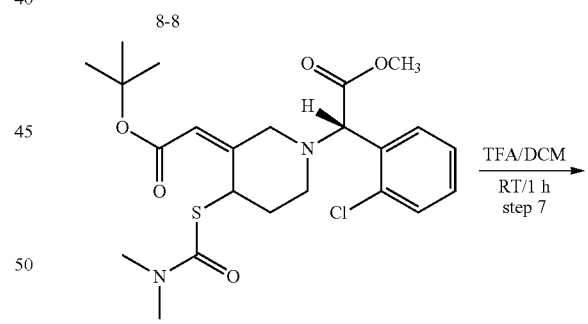

8-10

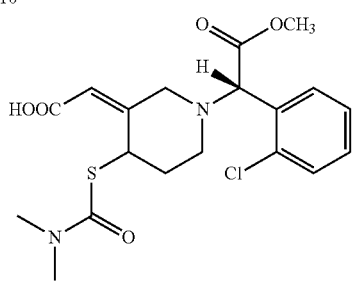

8

Step 1: Synthesis of 8-3

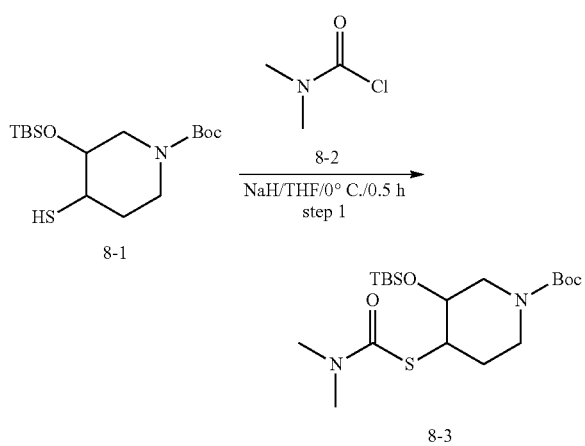

To a solution of 8-1 (5.00 g, 14.4 mmol) in THF (50 ml) was added NaH (0.688 g, 17.2 mmol, 60%, dispersion in Paraffin Liquid) portions at 0° C. After addition, the mixture was stirred at 0° C. for 1 h. 8-2 (1.86 g, 17.2 mmol) was added at 0° C. and stirred at 0° C. for 0.5 h. The reaction mixture was poured into a solution of sat·NH$_4$Cl (100 ml), extracted with EA (50 ml), the organic layer was washed with brine, dried over Na$_2$SO$_4$, and filtered. The filtrate was concentrated under reduce pressure and the residue was purified by silica gel chromatography (Petroleum ether/EtOAc=10/1) to give 8-3 (3.9 g, 65% yield) as a colourless oil.

$^1$H NMR (400 MHz, CDCl$_3$) δ 3.88-3.66 (m, 1H), 3.64-3.42 (m, 3H), 3.18 (d, J=33.4 Hz, 1H), 3.15-3.02 (m, 1H), 3.03-2.90 (m, 6H), 2.28-2.13 (m, 1H), 1.99 (d, J=9.4 Hz, 1H), 1.41 (d, J=14.9 Hz, 9H), 0.91-0.77 (m, 9H), 0.14-0.02 (m, 6H).

LC-MS [M+1-100]$^+$=319.2

Step 2: Synthesis of 8-4

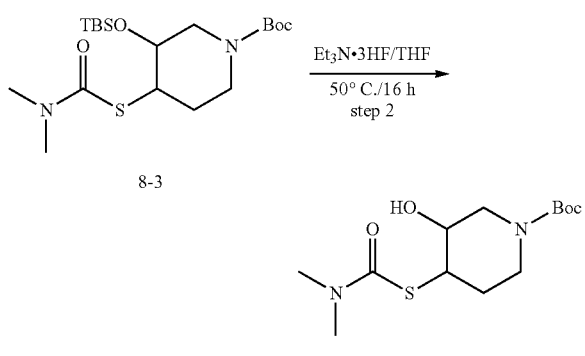

To a solution of 8-3 (3.9 g, 9.3 mmol) in THF (40 mL) was added Et$_3$N·3HF (4.5 g, 28.0 mmol) and the resulting mixture was stirred at 50° C. for 16 h. After completion, the reaction mixture was concentrated under reduce pressure. The residues purified by silica gel chromatography (Petroleum ether/EtOAc=3/1) to give 8-4 (2.4 g, 85% yield) as a white solid.

$^1$H NMR (400 MHZ, CDCl$_3$) δ 4.29 (dd, J=8.2, 5.2 Hz, 1H), 4.10 (m, 1H), 3.50-3.31 (m, 2H), 2.99 (s, 6H), 2.75 (s, 1H), 2.64 (dd, J=13.2, 9.7 Hz, 1H), 1.96 (ddd, J=13.2, 6.6, 2.9 Hz, 1H), 1.67-1.54 (m, 1H), 1.46-1.37 (s, 9H).

LC-MS [M+1-100]$^+$=205.1

Step 3. Synthesis of 8-5

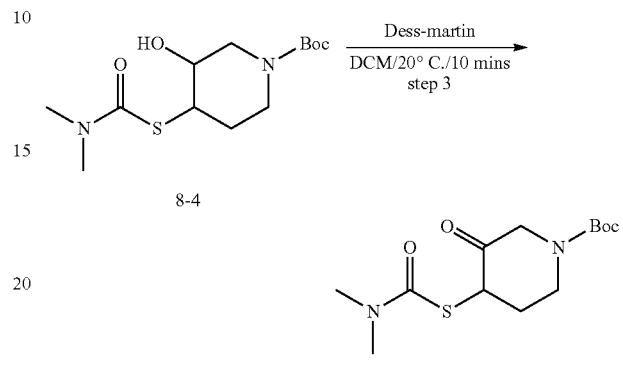

To a solution of 8-4 (2.4 g, 7.9 mmol) in DCM (30 mL) was added Dess-Martin Periodinane (8.3 g, 19.7 mmol), and the resulting mixture was stirred at 25° C. for 3 h. After completion, the reaction mixture was poured into a mixed solution of sat. Na$_2$S$_2$O$_3$/sat. NaHCO$_3$ (40 mL, 1:1). The resulting mixture was extracted with DCM (20 mL*2). The combined organic layers were washed with brine, dried over Na$_2$SO$_4$, and filtered. The filtrate was concentrated under reduce pressure and the residue was purified by silica gel chromatography (Petroleum ether/EtOAc=5/1) to give 8-5 (1.6 g, 67% yield) as a white solid.

LC-MS [M+1-56]$^+$=247.1

Step 4. Synthesis of 8-7

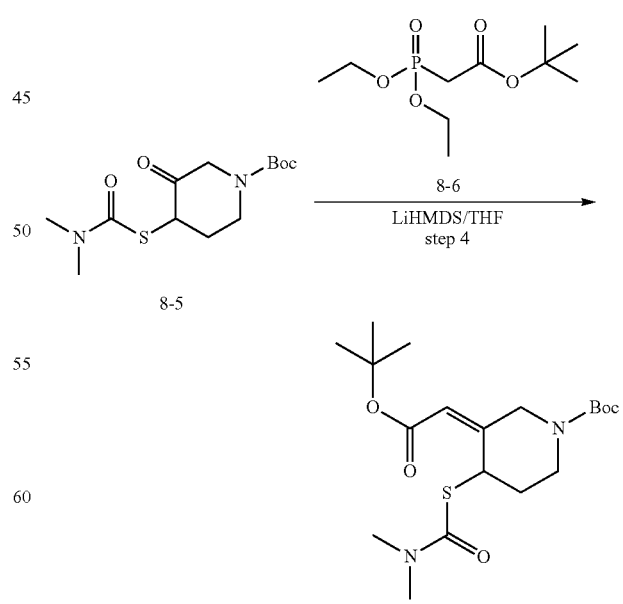

To a solution of 8-6 (1.5 g, 5.8 mmol) in THF (20 mL) was added LiHMDS (5.8 mL, 1M in THF, 5.8 mmol) at −60° C. under N₂, which was stirred at −60° C. for 30 min. 8-5 (1.6 g, 5.3 mmol) was added dropwise at −60° C. to the resulting mixture. After addition, the reaction mixture was stirred at 0~10° C. for 1 h. Then the reaction mixture was poured into a sat. NH₄Cl (20 mL) solution and the resulting mixture was extracted with EtOAc (20 mL*2). The combined organic layers were washed with brine, dried over Na₂SO₄ and filtered. The filtrate was concentrated under vacuum. The reaction was repeated five times and the residues were combined, purified by silica gel chromatography (Petroleum ether/EtOAc=20/1) to give 8-7 (100 mg, 4.7% yield) as a white solid.

LC-MS [M+Na]⁺=423.3

¹H NMR (400 MHZ, CDCl₃) δ 5.90 (s, 1H), 5.18 (d, J=14.0 Hz, 1H), 4.41 (s, 1H), 4.19 (d, J=16.1 Hz, 1H), 3.77 (s, 1H), 3.33 (s, 1H), 2.98 (s, 6H), 2.13 (s, 1H), 2.01-1.80 (m, 1H), 1.44 (d, J=10.3 Hz, 18H).

Step 5. Synthesis of 8-8

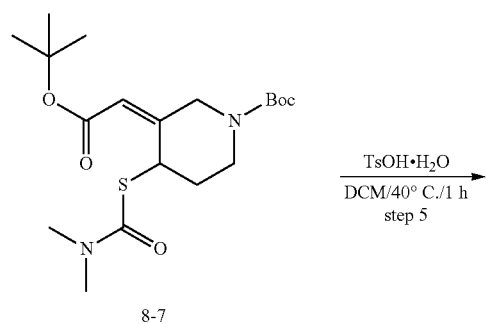

A mixture of 8-7 (50 mg, 0.125 mmol) and TsOH·H₂O (36 mg, 0.188 mmol) in DCM (1 mL) was stirred at 40° C. for 2 h. After completion, the reaction mixture was poured into a solution of sat. NaHCO₃ (2 mL) and the resulting mixture was extracted with DCM (2 mL*2). The combined organic layers were dried over Na₂SO₄, and filtered. The filtrate was concentrated under vacuum to give the crude 8-8 (crude, yield>100%) as a light yellow oil.

LC-MS [M+1]⁺=301.1

Step 6. Synthesis of 8-10

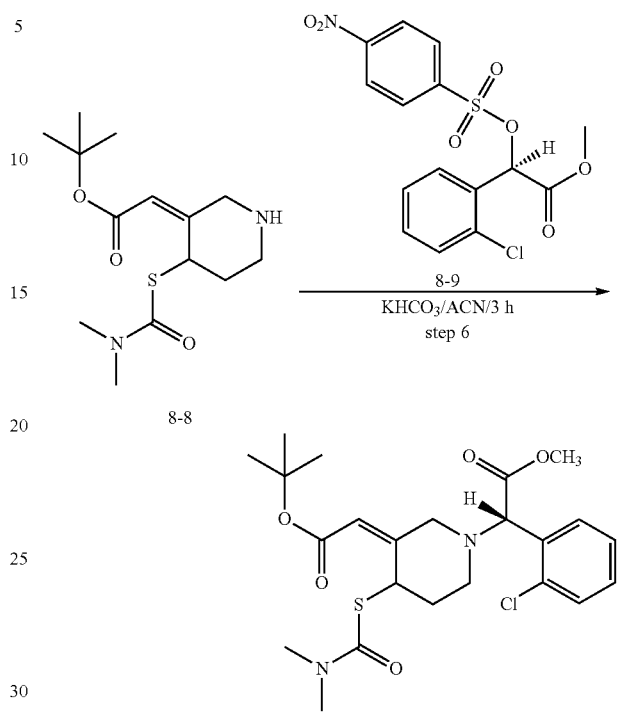

To a solution of 8-8 (crude, 0.125 mmol) in CH₃CN (1 mL) were added 8-9 (38.1 mg, 0.100 mmol) and KHCO₃ (50 mg, 0.500 mmol). The resulting mixture was stirred at 40° C. for 3 h and filtered. The filtrate was concentrated under reduce pressure, the residue was purified by Prep-TLC (Petroleum ether/EtOAc=10/1) to give 8-10 (10 mg, 16% yield) as a light yellow solid.

LC-MS [M+1]⁺=483.2

¹H NMR (400 MHZ, CDCl₃) δ 7.63-7.55 (m, 1H), 7.40-7.32 (m, 1H), 7.29-7.18 (m, 2H), 5.63 (s, 1.5H), 5.49 (s, 0.5H), 4.73 (d, J=5.0 Hz, 1H), 3.69 (d, J=1.1 Hz, 3H), 3.29-3.08 (m, 1H), 3.07-2.98 (m, 1H), 2.93 (d, J=19.1 Hz, 6H), 2.89 (d, J=11.8 Hz, 0.5H), 2.76 (td, J=12.0, 2.5 Hz, 0.5H), 2.70-2.57 (m, 1H), 2.29-2.04 (m, 1H), 2.04-1.83 (m, 1H), 1.50-1.41 (m, 9H).

Step 7. Synthesis of 8

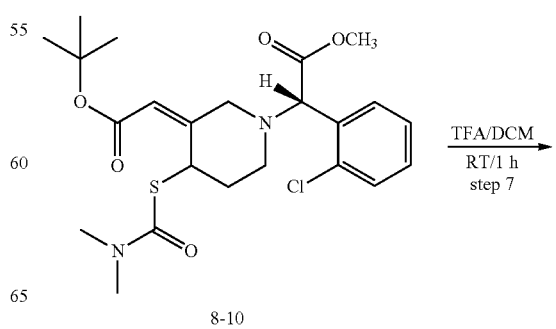

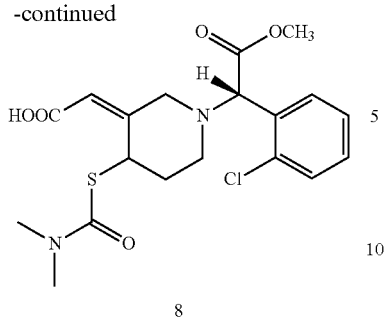

8

To a solution of 8-10 (10 mg, 0.021 mmol) in DCM (0.5 mL) was added TFA (0.5 mL) at 0° C. After the addition, the mixture was stirred at 0° C. for 3 h. The resulting mixture was poured into a solution of a sat. NaHCO$_3$ (3 mL), extracted with DCM (2 mL*2). The combined organic layers were washed with brine, dried over Na$_2$SO$_4$, and filtered. The filtrate was concentrated under reduce pressure. The residue was purified by Prep-TLC (DCM/MeOH=20/1) to give 8 (4 mg, yield 45%).

LC-MS [M+1]$^+$=427.1

$^1$H NMR (400 MHZ, CDCl$_3$) δ 7.64-7.52 (m, 1H), 7.41-7.35 (m, 1H), 7.32-7.18 (m, 2H), 5.71 (d, J=39.7 Hz, 1H), 5.42-5.31 (m, 1H), δ 4.76 (d, J=2.6 Hz, 1H). 3.69 (d, J=5.0 Hz, 3H), 3.36 (d, J=12.1 Hz, 0.5H), 3.27 (d, J=12.2 Hz, 0.5H), 3.18 (d, J=12.1 Hz, 0.5H), 2.98 (s, 6H), 2.89 (d, J=11.7 Hz, 0.5H), 2.79-2.62 (m, 2H), 2.33-2.11 (m, 1H), 1.91 (t, J=15.9 Hz, 1H).

Example 9

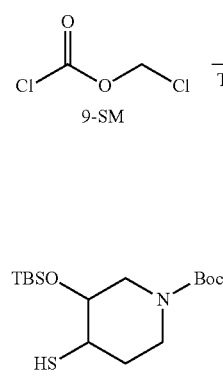

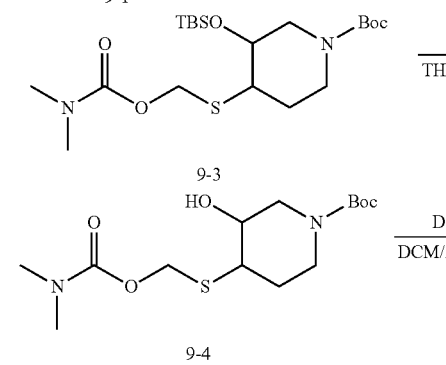

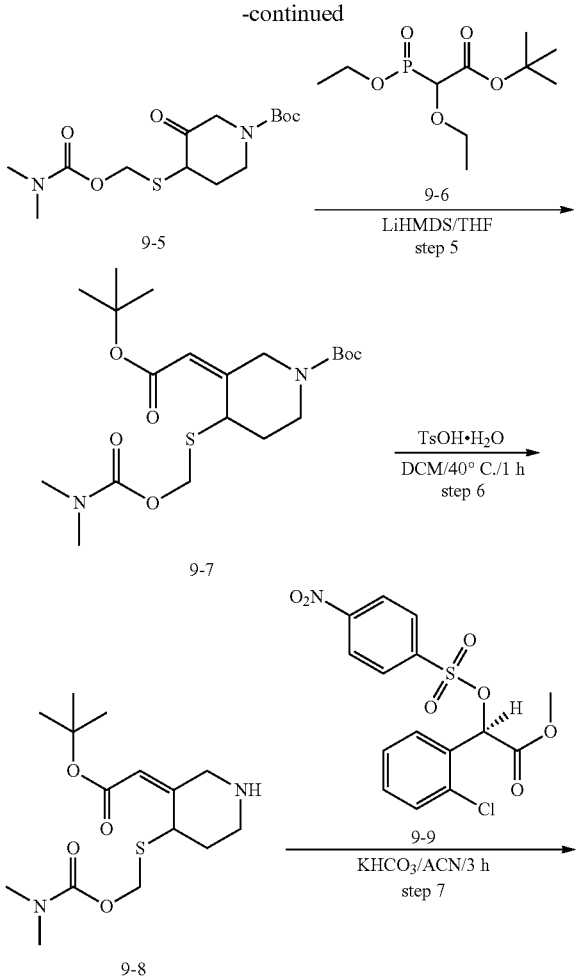

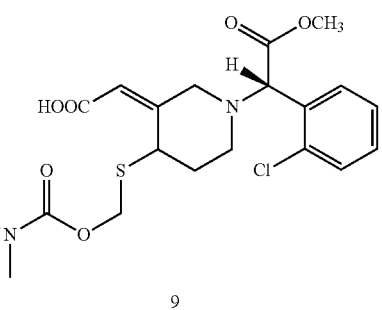

9

Step 1: Synthesis of 9-2

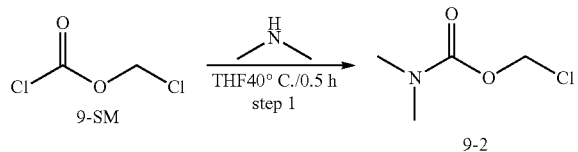

To a compound of 9-SM (11.0 g, 85.3 mmol) was added Dimethylamine (1.76 g, 18.7 mmol) in portions at 20° C. After addition, the mixture was stirred at 20° C. for 0.5 h. The mixture was concentrated under vacuum. The residue was purified by silica gel chromatography (Petroleum ether/EtOAc=20/1) to give 9-2 (7.8 g, yield 69%) as a colourless oil.

Step 2: Synthesis 9-3

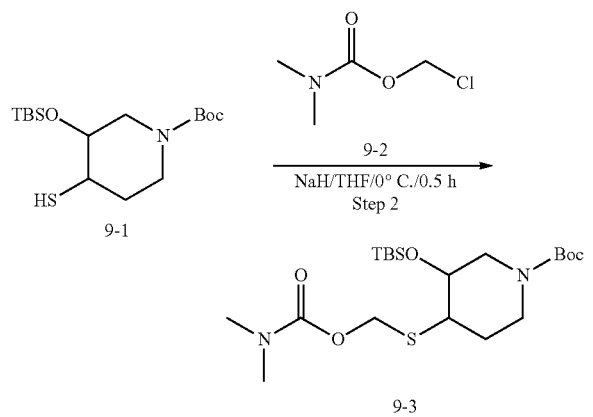

To a solution of 9-1 (5.00 g, 14.4 mmol) in THF (50 mL) was added NaH (0.700 g, 17.3 mmol) portions at 0° C., after addition, the mixture was stirred at 0° C. for 1 h. 9-2 (2.37 g, 17.3 mmol) was added at 0° C. and stirred at 0° C. for 0.5 h. The mixture was poured into a solution of sat. NH$_4$Cl (100 mL), extracted with EA (50 mL), the organic layers were washed with brine, dried over Na$_2$SO$_4$, and filtered. The filtrate was concentrated under reduce pressure and the residue was purified by silica gel chromatography (Petroleum ether/EtOAc=10/1) to give 9-3 (4.8 g, yield 65%) as a colourless oil.

$^1$H NMR (400 MHZ, CDCl$_3$) δ 5.25 (s, 2H), 3.90 (d, J=3.6 Hz, 1H), 3.75 (s, 1H), 3.48 (s, 1H), 3.09-2.94 (m, 2H), 2.94-2.79 (m, 8H), 2.19-2.06 (m, 1H), 1.43 (d, J=2.0 Hz, 9H), 0.97-0.73 (m, 9H), 0.14-0.02 (m, 6H).

Step 3: Synthesis of 9-4

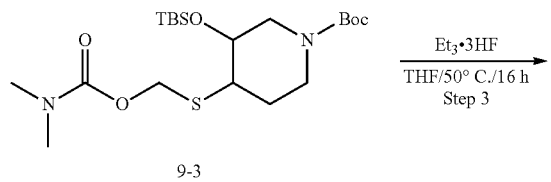

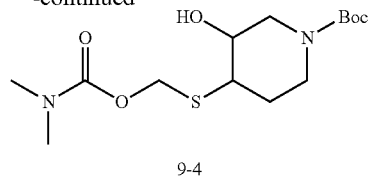

To a solution of 9-3 (4.7 g, 10.5 mmol) in THF (50 mL) was added Et$_3$N·3HF (5.0 g, 31.5 mmol) and the resulting mixture was stirred at 50° C. for 16 h. After completion, the reaction mixture was concentrated under reduce pressure. The residues purified by silica gel chromatography (Petroleum ether/EtOAc=3/1) to give 9-4 (3.2 g, yield 91%) as a colourless oil.

$^1$H NMR (400 MHZ, CDCl$_3$) δ 5.34 (d, J=12.1 Hz, 1H), 5.18 (d, J=12.1 Hz, 1H), 4.25 (d, J=10.8 Hz, 1H), 4.10-3.70 (m, 1H), 3.42 (s, 1H), 3.10 (s, 1H), 2.90 (d, J=7.7 Hz, 6H), 2.86-2.68 (m, 2H), 2.66 (dd, J=13.1, 9.7 Hz, 1H), 2.08-1.92 (m, 1H), 1.47-1.35 (m, 9H).

Step 4. Synthesis of 9-5

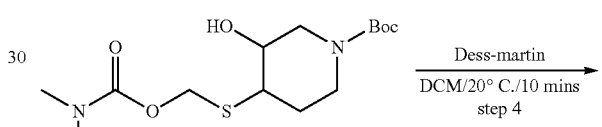

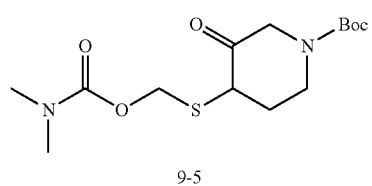

To a solution of 9-4 (3.0 g, 8.98 mmol) in DCM (30 mL) was added Dess-Martin Periodinane (5.7 g, 13.47 mmol), and the resulting mixture was stirred at 25° C. for 10 mins. After completion, the reaction mixture was poured into a mixed solution of sat·Na$_2$S$_2$O$_3$/sat. NaHCO$_3$ (100 mL, 1:1). The resulting mixture was extracted with DCM (50 mL*2). The combined organic layers was washed with brine, dried over Na$_2$SO$_4$, and filtered. The filtrate was concentrated under reduce pressure and the residue was purified by silica gel chromatography (Petroleum ether/EtOAc=5/1) to give 9-5 (2.2 g, yield 74%) as a light orange oil.

$^1$H NMR (400 MHz, CDCl$_3$) δ 5.22 (d, J=12.1 Hz, 1H), 5.12 (d, J=12.1 Hz, 1H), 4.24 (d, J=17.5 Hz, 1H), δ 4.16-4.06 (m, 1H), 3.72 (t, J=5.3 Hz, 2H), 3.48 (ddd, J=13.7, 9.5, 4.1 Hz, 1H), 2.90 (d, J=10.3 Hz, 6H), 2.34 (dd, J=9.5, 5.0 Hz, 1H), 2.15-1.96 (m, 1H), 1.44 (s, 9H).

Step 5. Synthesis of 9-7

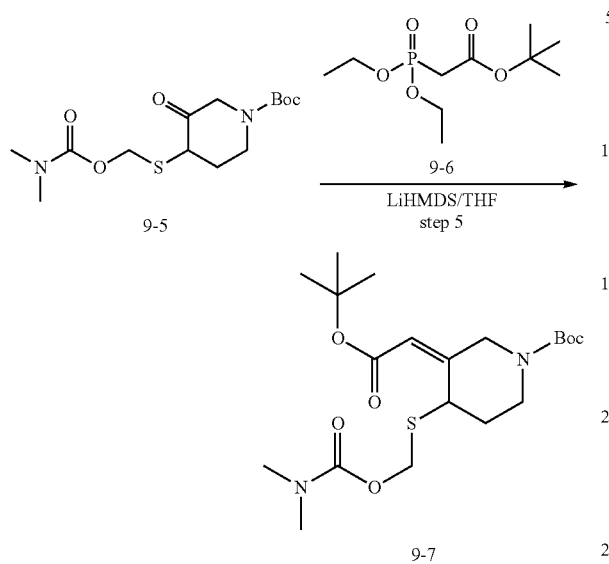

To a solution of 9-6 (1.7 g, 6.6 mmol) in THF (20 mL) was added LiHMDS (6.6 mL, 1M in THF, 6.6 mmol) at −60° C. under N₂, which was stirred at −60° C. for 30 min. 9-5 (2.0 g, 6.0 mmol) was added dropwise at −60° C. to the resulting mixture. After addition, the reaction mixture was stirred at 0~10° C. for 1 h. Then the reaction mixture was poured into a sat. NH₄Cl (50 mL) solution and the resulting mixture was extracted with EtOAc (30 mL*2). The combined organic layers were washed with brine, dried over Na₂SO₄ and filtered. The filtrate was concentrated under vacuum. The reaction was repeated five times and the residues were combined and purified by silica gel chromatography (Petroleum ether/EtOAc=20/1) to give 9-7 (1.0 g, 28.8% yield) as a yellow oil.

¹H NMR (400 MHZ, CDCl₃) δ 5.72 (s, 1H), 5.51 (s, 1H), 5.29 (s, 0.5H), 5.26 (s, 0.5H), 5.07 (d, J=12.0 Hz, 1H), 4.40-4.04 (m, 1H), 3.97 (d, J=20.3 Hz, 2H), 3.15 (s, 1H), 2.88 (d, J=5.3 Hz, 6H), 2.03 (dd, J=16.7, 10.0 Hz, 1H), 1.86 (d, J=13.9 Hz, 1H), 1.45 (dd, J=12.1, 5.8 Hz, 18H).

Step 6. Synthesis of 9-8

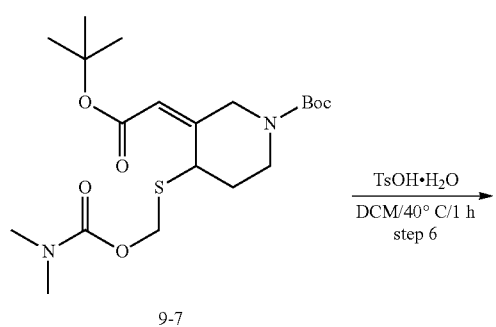

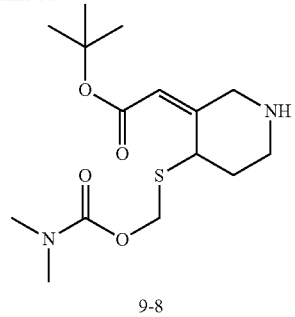

A mixture of 9-7 (800 mg, 1.8 mmol) and TsOH·H₂O (469 mg, 2.72 mmol) in DCM (8 mL) was stirred at 40° C. for 2 h. After completion, the reaction mixture was poured into a solution of sat. NaHCO₃ (30 mL) and the resulting mixture was extracted with DCM (10 mL*2). The combined organic layers were dried over Na₂SO₄, and filtered. The filtrate was concentrated and purified by silica gel (DCM/MeOH=20/1) to give 9-8 (185 mg, 31% yield) as a colourless oil.

LC-MS [M+1]⁺=331.2

Step 7. Synthesis of 9-10

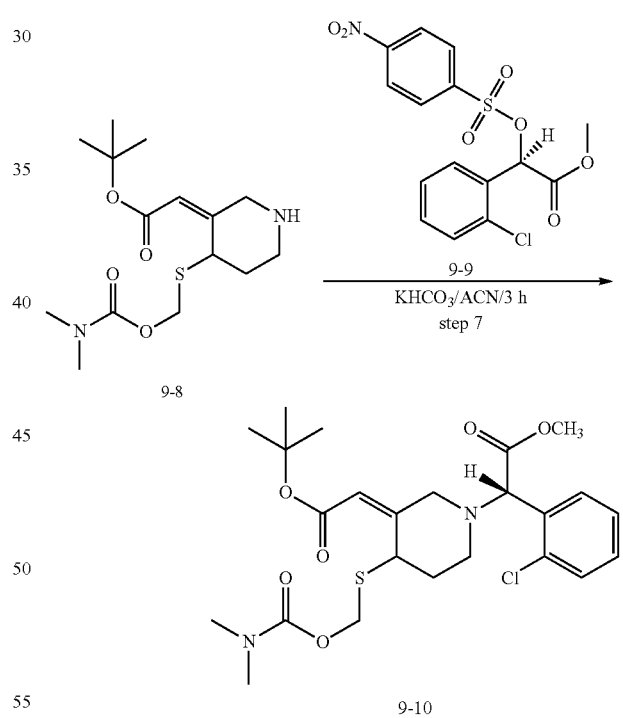

To a solution of 9-8 (185 mg, 0.56 mmol) in CH₃CN (2 mL) were added 9-9 (194 mg, 0.50 mmol) and KHCO₃ (224 mg, 2.24 mmol). The resulting mixture was stirred at 40° C. for 3 h and filtered. The filtrate was concentrated under reduce pressure, the residue was purified by Prep-TCL (Petroleum ether/EtOAc=10/1) to give 9-10 (200 mg, 69.8% yield) as a colourless oil.

LC-MS [M+1]⁺=513.2

¹H NMR (CDCl₃ (400 MHZ) δ 7.61-7.57 (m, 1H), 7.37 (m, 1H), 7.28-7.22 (m, 2H), 5.68 (s, 0.5H), 5.51 (s, 0.5H), 5.48 (t, J=4.4 Hz, 1H), 5.28-5.21 (m, 1H), 5.06 (dd, J=12.0, 7.8 Hz, 1H), 4.75 (s, 1H), 3.68 (d, J=3.8 Hz, 3H), 3.53-3.47 (m, 0.5H), 3.40 (d, J=11.4 Hz, 0.5H), 3.08 (d, J=12.1 Hz, 0.5H), 2.92-2.79 (m, 6.5H), 2.71 (dt, J=11.9, 6.0 Hz, 1H), 2.59 (dd, J=10.2, 2.5 Hz, 1H), 2.29-2.11 (m, 1H), 1.89 (dd, J=14.3, 2.2 Hz, 1H), 1.43 (d, J=6.6 Hz, 9H).

Step 8. Synthesis of 9

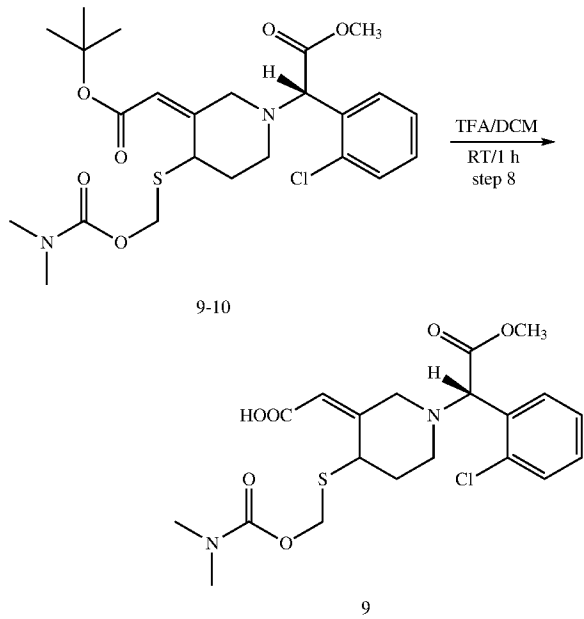

9-10

9

To a solution of 9-10 (200 mg, 0.39 mmol) in DCM (3 mL) was added TFA (3 mL) at 0° C. After the addition, the mixture was stirred at 0° C. for 3 h. The resulting mixture was poured into a mixture of a sat. NaHCO$_3$ (15 mL), extracted with DCM (5 mL*2). The combined organic layer was washed with brine, dried over Na$_2$SO$_4$, and filtered. The filtrate was concentrated under reduce pressure to give 9 (50 mg, 28% yield) as a white solid.

LC-MS [M+1]$^+$=457.2

$^1$H NMR (CDCl$_3$ 400 MHZ) δ 7.61-7.54 (m, 1H), 7.42-7.36 (m, 1H), 7.30-7.22 (m, 2H), 5.75 (s, 0.5H), 5.62 (s, 0.5H), 5.40 (s, 1H), 5.29-5.20 (m, 1H), 5.09 (dd, J=12.1, 7.2 Hz, 1H), 4.79 (d, J=2.7 Hz, 1H), 3.69 (dd, J=4.7, 2.6 Hz, 3H), 3.57 (d, J=11.8 Hz, 0.5H), 3.49 (d, J=12.1 Hz, 0.5H), 3.15 (d, J=12.4 Hz, 0.5H), 2.93 (d, J=12.4 Hz, 0.5H), 2.90-2.80 (m, 6H), 2.72 (m, 1H), 2.64 (d, J=7.1 Hz, 1H), 2.19 (m, 1H), 1.96-1.82 (m, 1H).

Example 10

Biochemical Assays

Assay 1: Pharmacokinetic in Rats

Male Sprague-Dawley rats were used to conduct pharmacokinetic experiment.

Test compounds (clopidogrel and exemplary compounds provided herein) was administrated orally or intravenously to rat under fast condition. Blood samples were collected via jugular vein at 5 min, 15 min, 30 min, 60 min and 120 min time points with EDTA-K$_2$ (anticoagulant), 3'-methoxyphenacyl bromide (MPBr, derivatization reagent) and phenylmethylsulfonyl fluoride (PMSF, stabilizer). Plasma samples were then harvested by centrifuging at 1500 g for 10 min under 2~8° C. and stored at −80° C. after separation. Plasma samples were loaded to a LC-MS/MS instrument after extraction to determine the concentration of the thiol active metabolite. The concentration results in rat plasma were demonstrated in FIGS. 1 and 2.

As shown in FIG. 1, at a dose level of 10 mg/kg, compounds 1a, 1b and 2a provided herein reached peak concentration of the thiol active metabolite in less than 20 minutes after administration, compared to clopidogrel that reached peak concentration at about 30 minutes after administration. Furthermore, the peak concentrations of the thiol active metabolite for compounds 1a, 1b and 2a are significantly higher than that for clopidogrel. These results indicate that compounds 1a, 1b and 2a provide faster and more efficient release of the active metabolite than clopidogrel.

Figure 2:
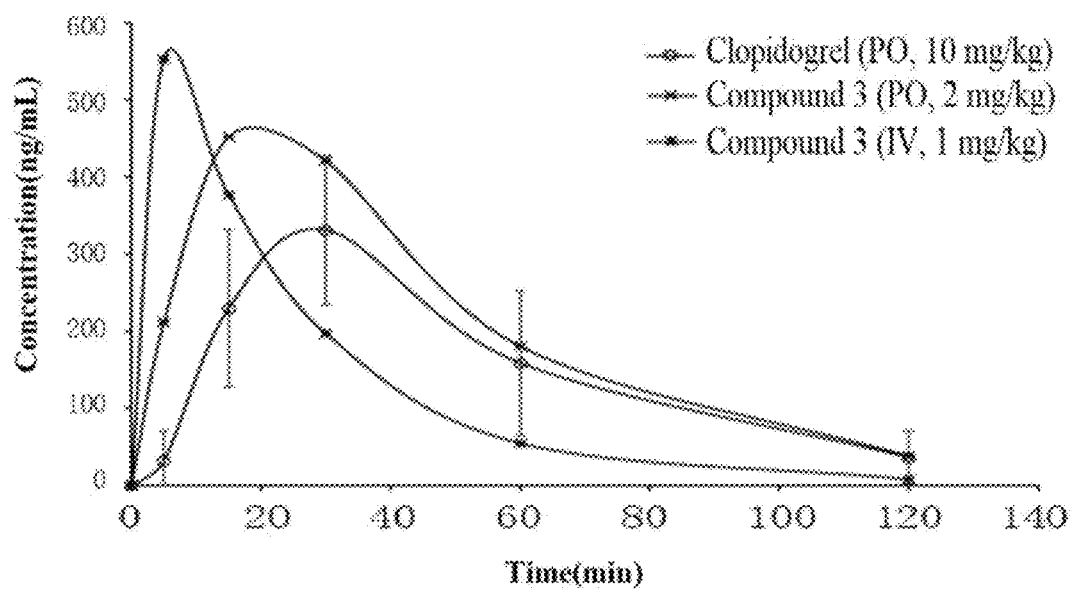
FIG. 2 shows the concentration of the active metabolite in rat plasma after oral administration of clopidogrel at a dose level of 10 mg/kg, oral administration of compound 3 at a dose level of 2 mg/kg, and intravenous administration of compound 3 at a dose level of 1 mg/kg.

As shown in FIG. 2, when administered orally, compound 3 provided herein at a dose level of 2 mg/kg reached peak concentration of the thiol active metabolite at about 20 minutes after administration, compared to clopidogrel at a much higher dose level of 10 mg/kg that reached peak concentration at about 30 minutes after administration. When administered intravenously, compound 3 provided herein at a dose level of only 1 mg/kg reached peak concentration of the thiol active metabolite at about 6 minutes after administration. These results indicate that compound 3 provides faster and more efficient release of the active metabolite than clopidogrel.

Other compounds provided herein show comparable, or even faster and more efficient release of the active metabolite than clopidogrel.

Assay 2: Antiaggregatory Action in Rats

Male Sprague-Dawley rats were used for ex vivo platelet aggregation experiments. After oral administrated with (clopidogrel, exemplary compounds provided herein and vehicle (control)) to rats, blood was collected via jugular vein at 0.5 hour, 1 hour and 2 hour time points, using 3.8% (w/v) sodium citrate solution as an anticoagulant (1/9 volume of whole blood). Blood samples with citrate were centrifuged at a low speed of 1000 rmp for 5 min to obtain platelet-rich plasma (PRP). After separation of PRP, the remained blood was further centrifuged at a high speed of 3000 rmp for 10 min to obtain platelet-poor plasma (PPP). The number of platelets in PRP was measured by hematology analyzer (Siemens, ADVIA2120), and adjusted to 4×10$^8$/mL with PPP.

Platelet aggregation was determined using turbidimetric aggregometry method by an automatic platelet aggregometer (PRECIL LBY-NJ4). The aggregometer was primarily warmed up to 37° C., and PRP (290 µL) sample was added to the cuvette and set in the automatic platelet aggregometer. After a 5 min pre-incubation, calibrated the aggregometer using PPP to representing 100% aggregation and PRP to representing 0% aggregation. Finally, a volume of 10 µL ADP solution (final concentration 10 µM) was added to PRP sample to initial platelet aggregation. Platelet aggregation was monitored for 5 min and maximum platelet aggregation (%) was reported within the duration. Antiaggregatory action of test compounds was expressed as inhibition (%) which determined by the relation:

Inhibition (%) = (maximum platelet aggregation (%) of control − maximum platelet aggregation (%) of test compound)/

(maximum platelet aggregation (%) of control) * 100

Figure 3:
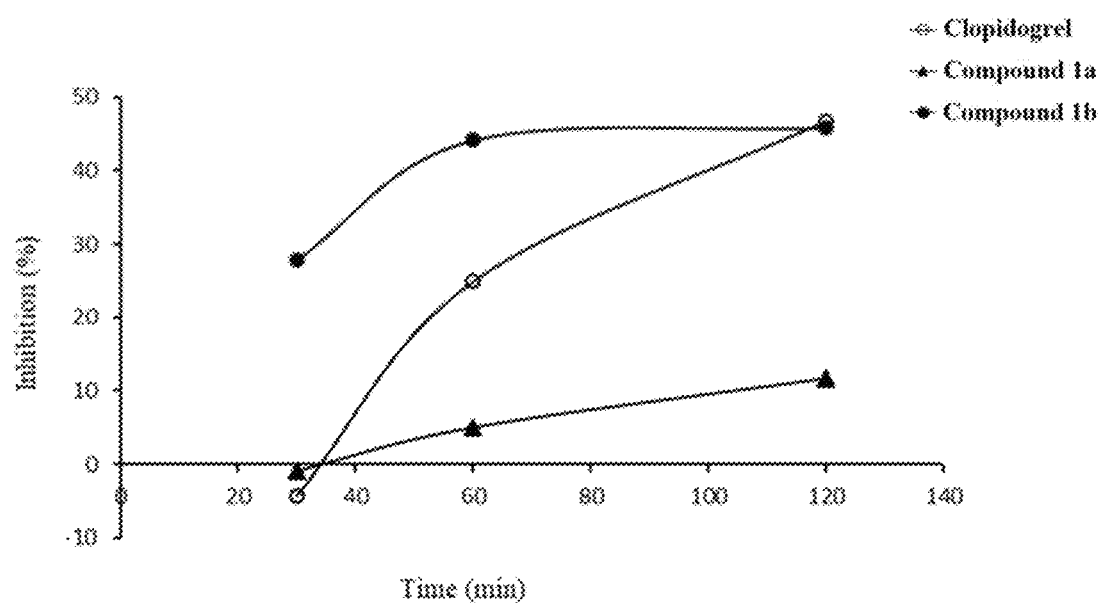
FIG. 3 shows the inhibition (%) of aggregation after oral administration of test compounds in rats at a dose level of 10 mg/kg (clopidogrel), 0.5 mg/kg (compound 1a) and 2 mg/kg (compound 1b).

The inhibition (%) results for the test compounds were demonstrated in FIG. 3. The dose levels were 10 mg/kg, 0.5 mg/kg and 2 mg/kg for clopidogrel, 1a and 1b respectively. As can be seen from FIG. 2, clopidogrel reaches maximum inhibition of platelet aggregation at about 45% in about 120 minutes after administration, whereas compound 1b shows the maximum inhibition at about 45% in 60 minutes after administration at a much lower dose level than clopidogrel, indicating a much faster onset of action and much higher potency than clopidogrel.

Other compounds provided herein could show faster onset of action and higher potency than clopidogrel.

The foregoing description is considered as illustrative only of the principles of the present disclosure. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

What is claimed is:

1. A compound having Formula (I):

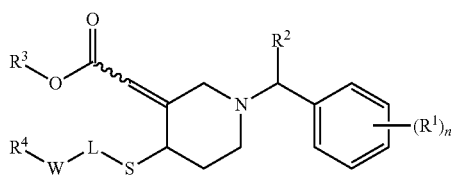

(I)

or a pharmaceutically acceptable salt thereof,
wherein represents a double bond in Z or E configuration;
$R^1$ is selected from the group consisting of hydrogen, halogen, nitro, cyano, hydroxyl, amino, alkyl, alkenyl, alkynyl, heteroalkyl, heteroalkenyl, and heteroalknyl, wherein each of alkyl, alkenyl, alkynyl, heteroalkyl, heteroalkenyl, and heteroalknyl is optionally substituted with one or more $R^a$;
$R^2$ is —C(O)$R^b$;
$R^3$ is selected from hydrogen or alkyl;
L is alkyl;
W is selected from:

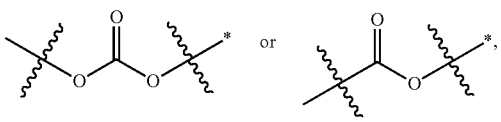

wherein the * end of W is connected to L;
$R^4$ is selected from hydrogen or alkyl;
each of $R^a$ is independently selected from the group consisting of hydrogen, halogen, hydroxyl, amino, cyano, nitro, or —N$R^c R^d$,
$R^b$ is —O$R^e$;
each of $R^c$ and $R^d$ is independently selected from hydrogen or alkyl;

$R^c$ is alkyl;
n is 0, 1 or 2.

2. The compound of claim 1, or a pharmaceutically acceptable salt thereof, wherein
    $R^1$ is selected from the group consisting of hydrogen, halogen, nitro, cyano, hydroxyl, amino, alkyl, and heteroalkyl, wherein each of alkyl and heteroalkyl is optionally substituted with one or more $R^a$.

3. The compound of claim 1, or a pharmaceutically acceptable salt thereof, wherein $R^1$ is fluoro, chloro, bromo, cyano, methyl or trifluoromethyl.

4. The compound of claim 1, or a pharmaceutically acceptable salt thereof, wherein $R^2$ is —C(O)OCH$_3$.

5. The compound of claim 1, or a pharmaceutically acceptable salt thereof, wherein L is a direct bond, —CH$_2$—, —CH(CH$_3$)—, or —C(CH$_3$)$_2$—.

6. The compound of claim 1, or a pharmaceutically acceptable salt thereof, wherein $R^4$ is hydrogen, —CH$_3$, —CH$_2$CH$_3$, —CH(CH$_3$)$_2$, or —C(CH$_3$)$_3$.

7. The compound of claim 1, or a pharmaceutically acceptable salt thereof, wherein n is 1.

8. The compound of claim 1, or a pharmaceutically acceptable salt thereof, having a formula selected from the group consisting of:

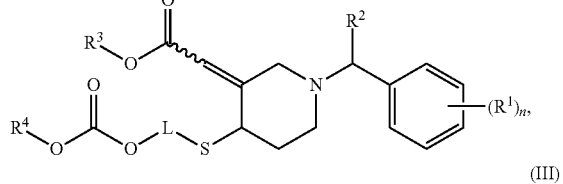

(II)

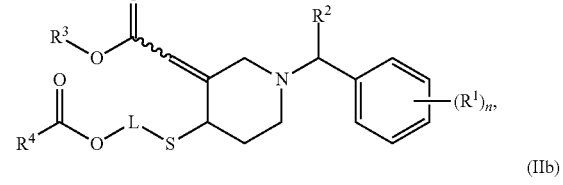

(III)

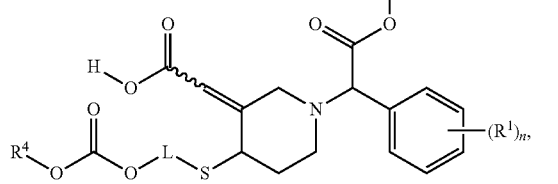

(IIb)

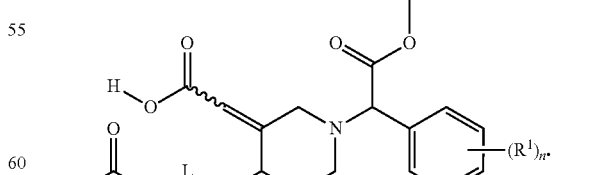

(IIIb)

9. The compound of claim 1, or a pharmaceutically acceptable salt thereof, wherein $R^1$ is halogen and n is 1.

10. A compound having a formula selected from the group consisting of:

123
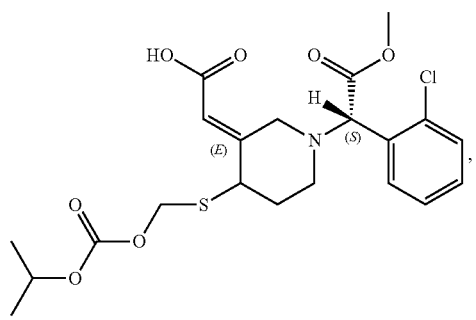
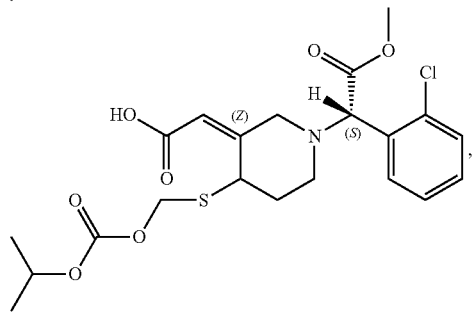
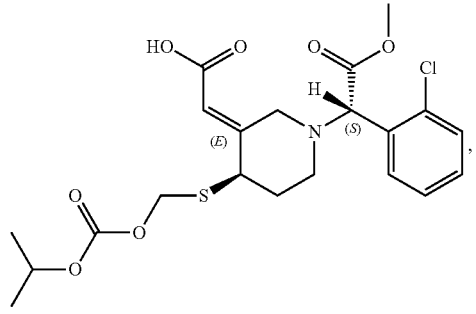
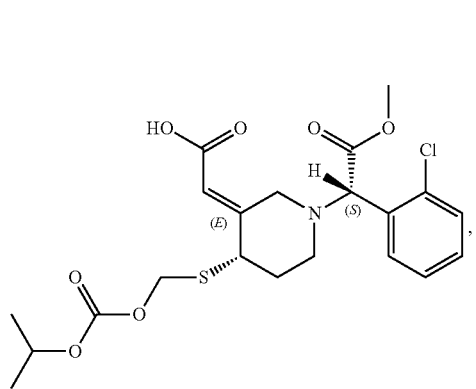
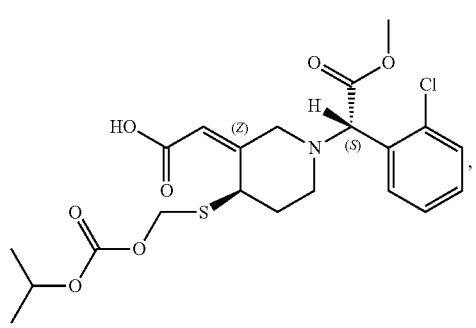
124
-continued
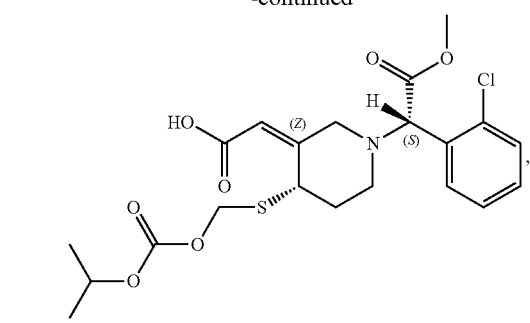
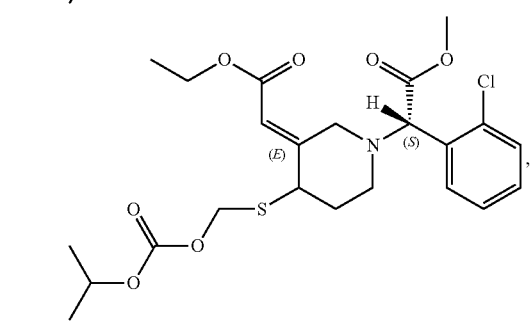
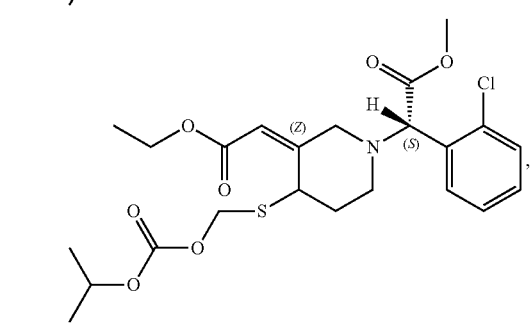
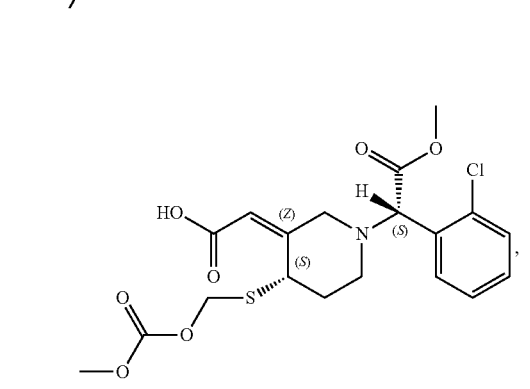
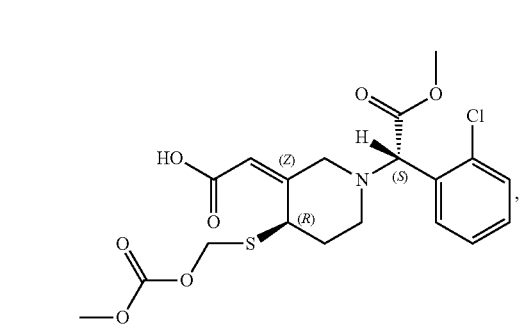

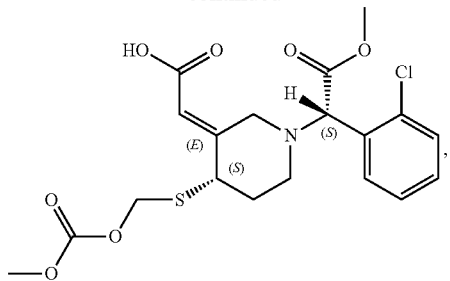

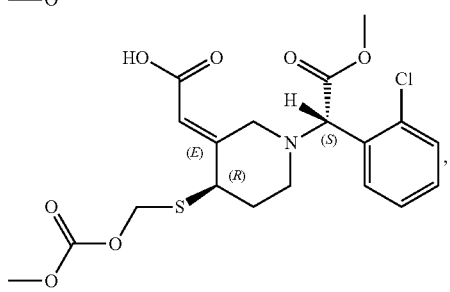

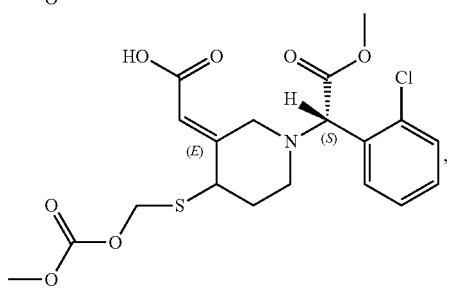

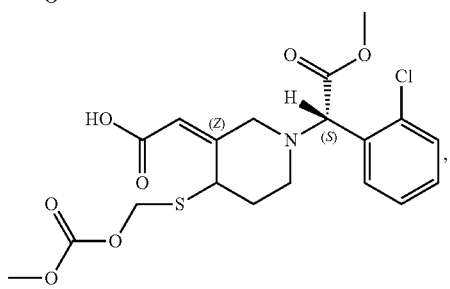

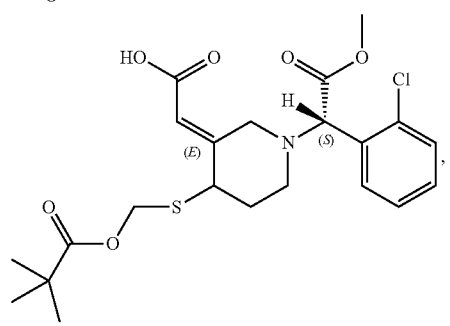

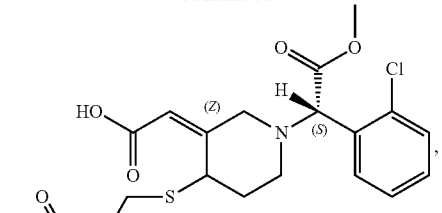

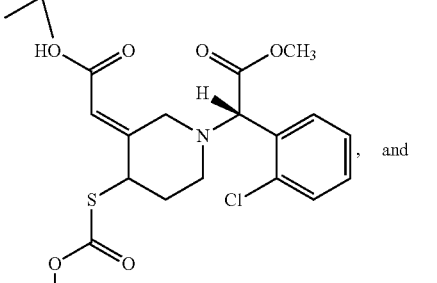

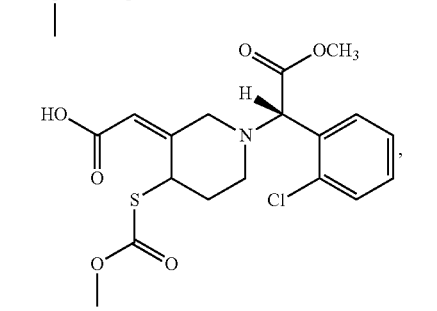

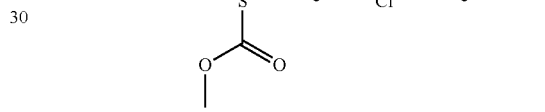

or a pharmaceutically acceptable salt thereof.

11. A pharmaceutical composition comprising the compound of claim 1 or a pharmaceutically acceptable salt thereof, and a pharmaceutically acceptable carrier.

12. The pharmaceutical composition of claim 11, which is formulated for oral administration or injection administration.

13. A method for treating a vascular diseases in a subject in need thereof, comprising administering an effective amount of a compound of claim 1 or a pharmaceutically acceptable salt thereof to the subject, wherein the vascular disease is selected from atherothrombosis, ischemia, stroke, cerebral thrombosis, arterial thrombosis, thrombotic cerebrovascular and blood clots.

14. A method for inhibiting platelet aggregation in a subject in need thereof, comprising administering an effective amount of a compound of claim 1 or a pharmaceutically acceptable salt thereof to the subject, wherein the subject has a vascular disease selected from atherothrombosis, ischemia, stroke, cerebral thrombosis, arterial thrombosis, thrombotic cerebrovascular and blood clots.

* * * * *